(12) United States Patent
Hayter et al.

(10) Patent No.: US 8,362,904 B2
(45) Date of Patent: *Jan. 29, 2013

(54) ANALYTE MONITORING SYSTEM AND METHODS

(75) Inventors: Gary Hayter, Oakland, CA (US);
Martin J. Fennell, Concord, CA (US);
Lei He, Moraga, CA (US); Mark K. Sloan, Redwood City, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/089,309

(22) Filed: Apr. 18, 2011

(65) Prior Publication Data

US 2011/0280132 A1 Nov. 17, 2011

Related U.S. Application Data

(63) Continuation of application No. 12/117,665, filed on May 8, 2008, now Pat. No. 7,928,850.

(60) Provisional application No. 60/916,677, filed on May 8, 2007.

(51) Int. Cl.
*G08B 23/00* (2006.01)
(52) U.S. Cl. ............ 340/573.1; 340/500; 340/540; 340/539.1; 600/310; 600/316; 600/345; 600/347
(58) Field of Classification Search ............ 340/500, 340/540, 539.1, 573.1; 600/310, 316, 345, 600/347, 551; 73/1.01
See application file for complete search history.

(56) References Cited

U.S. PATENT DOCUMENTS

| | | | |
|---|---|---|---|
| 2,755,036 A | 7/1956 | Mikko | |
| 3,260,656 A | 7/1966 | Ross, Jr. | |
| 3,304,413 A | 2/1967 | Lehmann et al. | |
| 3,581,062 A | 5/1971 | Aston | |
| 3,651,318 A | 3/1972 | Czekajewski | |
| 3,653,841 A | 4/1972 | Klein | |
| 3,698,386 A | 10/1972 | Fried | |
| 3,719,564 A | 3/1973 | Lilly, Jr. et al. | |
| 3,768,014 A | 10/1973 | Smith et al. | |
| 3,776,832 A | 12/1973 | Oswin et al. | |
| 3,837,339 A | 9/1974 | Aisenberg et al. | |
| 3,919,051 A | 11/1975 | Koch et al. | |
| 3,926,760 A | 12/1975 | Allen et al. | |
| 3,949,388 A | 4/1976 | Fuller | |
| 3,972,320 A | 8/1976 | Kalman | |
| 3,979,274 A | 9/1976 | Newman | |
| 4,003,379 A | 1/1977 | Ellinwood, Jr. | |
| 4,008,717 A | 2/1977 | Kowarski | |
| 4,016,866 A | 4/1977 | Lawton | |

(Continued)

FOREIGN PATENT DOCUMENTS

DE 4234553 1/1995
EP 0010375 4/1980
(Continued)

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.

(Continued)

*Primary Examiner* — George Bugg
*Assistant Examiner* — Sisay Yacob
(74) *Attorney, Agent, or Firm* — Jackson & Co., LLP

(57) ABSTRACT

Methods and systems for providing data communication in medical systems are disclosed.

18 Claims, 14 Drawing Sheets

U.S. PATENT DOCUMENTS

| | | | |
|---|---|---|---|
| 4,021,718 A | 5/1977 | Konrad | |
| 4,036,749 A | 7/1977 | Anderson | |
| 4,055,175 A | 10/1977 | Clemens et al. | |
| 4,059,406 A | 11/1977 | Fleet | |
| 4,076,596 A | 2/1978 | Connery et al. | |
| 4,098,574 A | 7/1978 | Dappen | |
| 4,100,048 A | 7/1978 | Pompei et al. | |
| 4,129,128 A | 12/1978 | McFarlane | |
| 4,151,845 A | 5/1979 | Clemens | |
| 4,154,231 A | 5/1979 | Russell | |
| 4,168,205 A | 9/1979 | Danninger et al. | |
| 4,172,770 A | 10/1979 | Semersky et al. | |
| 4,178,916 A | 12/1979 | McNamara | |
| 4,193,026 A | 3/1980 | Finger et al. | |
| 4,206,755 A | 6/1980 | Klein | |
| 4,224,125 A | 9/1980 | Nakamura et al. | |
| 4,240,438 A | 12/1980 | Updike et al. | |
| 4,240,889 A | 12/1980 | Yoda et al. | |
| 4,245,634 A | 1/1981 | Albisser et al. | |
| 4,247,297 A | 1/1981 | Berti et al. | |
| 4,271,449 A | 6/1981 | Grogan | |
| 4,318,784 A | 3/1982 | Higgins et al. | |
| 4,327,725 A | 5/1982 | Cortese et al. | |
| 4,331,869 A | 5/1982 | Rollo | |
| 4,340,458 A | 7/1982 | Lerner et al. | |
| 4,344,438 A | 8/1982 | Schultz | |
| 4,349,728 A | 9/1982 | Phillips et al. | |
| 4,352,960 A | 10/1982 | Dormer et al. | |
| 4,356,074 A | 10/1982 | Johnson | |
| 4,365,637 A | 12/1982 | Johnson | |
| 4,366,033 A | 12/1982 | Richter et al. | |
| 4,375,399 A | 3/1983 | Havas et al. | |
| 4,384,586 A | 5/1983 | Christiansen | |
| 4,390,621 A | 6/1983 | Bauer | |
| 4,392,933 A | 7/1983 | Nakamura et al. | |
| 4,401,122 A | 8/1983 | Clark, Jr. | |
| 4,404,066 A | 9/1983 | Johnson | |
| 4,407,959 A | 10/1983 | Tsuji et al. | |
| 4,417,588 A | 11/1983 | Houghton et al. | |
| 4,418,148 A | 11/1983 | Oberhardt | |
| 4,420,564 A | 12/1983 | Tsuji et al. | |
| 4,425,920 A | 1/1984 | Bourland et al. | |
| 4,427,004 A | 1/1984 | Miller et al. | |
| 4,427,770 A | 1/1984 | Chen et al. | |
| 4,431,004 A | 2/1984 | Bessman et al. | |
| 4,436,094 A | 3/1984 | Cerami | |
| 4,440,175 A | 4/1984 | Wilkins | |
| 4,441,968 A | 4/1984 | Emmer et al. | |
| 4,444,892 A | 4/1984 | Malmros | |
| 4,450,842 A | 5/1984 | Zick et al. | |
| 4,458,686 A | 7/1984 | Clark, Jr. | |
| 4,461,691 A | 7/1984 | Frank | |
| 4,467,811 A | 8/1984 | Clark, Jr. | |
| 4,469,110 A | 9/1984 | Slama | |
| 4,477,314 A | 10/1984 | Richter et al. | |
| 4,478,976 A | 10/1984 | Goertz et al. | |
| 4,483,924 A | 11/1984 | Tsuji et al. | |
| 4,484,987 A | 11/1984 | Gough | |
| 4,494,950 A | 1/1985 | Fischell | |
| 4,509,531 A | 4/1985 | Ward | |
| 4,512,348 A | 4/1985 | Uchigaki et al. | |
| 4,522,690 A | 6/1985 | Venkatasetty | |
| 4,524,114 A | 6/1985 | Samuels et al. | |
| 4,526,661 A | 7/1985 | Steckhan et al. | |
| 4,527,240 A | 7/1985 | Kvitash | |
| 4,534,356 A | 8/1985 | Papadakis | |
| 4,538,616 A | 9/1985 | Rogoff | |
| 4,543,955 A | 10/1985 | Schroeppel | |
| 4,545,382 A | 10/1985 | Higgins et al. | |
| 4,552,840 A | 11/1985 | Riffer | |
| 4,560,534 A | 12/1985 | Kung et al. | |
| 4,569,589 A | 2/1986 | Neufeld | |
| 4,571,292 A | 2/1986 | Liu et al. | |
| 4,573,994 A | 3/1986 | Fischell et al. | |
| 4,581,336 A | 4/1986 | Malloy et al. | |
| 4,595,011 A | 6/1986 | Phillips | |
| 4,595,479 A | 6/1986 | Kimura et al. | |
| 4,601,707 A | 7/1986 | Albisser et al. | |
| 4,619,754 A | 10/1986 | Niki et al. | |
| 4,619,793 A | 10/1986 | Lee | |
| 4,627,445 A | 12/1986 | Garcia et al. | |
| 4,627,908 A | 12/1986 | Miller | |
| 4,633,878 A | 1/1987 | Bombardien | |
| 4,633,881 A | 1/1987 | Moore et al. | |
| 4,637,403 A | 1/1987 | Garcia et al. | |
| 4,648,408 A | 3/1987 | Hutcheson et al. | |
| 4,650,547 A | 3/1987 | Gough | |
| 4,653,513 A | 3/1987 | Dombrowski | |
| 4,654,197 A | 3/1987 | Lilja et al. | |
| 4,655,880 A | 4/1987 | Liu | |
| 4,655,885 A | 4/1987 | Hill et al. | |
| 4,658,463 A | 4/1987 | Sugita et al. | |
| 4,671,288 A | 6/1987 | Gough | |
| 4,674,652 A | 6/1987 | Aten et al. | |
| 4,679,562 A | 7/1987 | Luksha | |
| 4,680,268 A | 7/1987 | Clark, Jr. | |
| 4,682,602 A | 7/1987 | Prohaska | |
| 4,684,537 A | 8/1987 | Graetzel et al. | |
| 4,685,463 A | 8/1987 | Williams | |
| 4,685,903 A | 8/1987 | Cable et al. | |
| 4,686,624 A | 8/1987 | Blum et al. | |
| 4,703,324 A | 10/1987 | White | |
| 4,703,756 A | 11/1987 | Gough et al. | |
| 4,711,245 A | 12/1987 | Higgins et al. | |
| 4,717,673 A | 1/1988 | Wrighton et al. | |
| 4,721,601 A | 1/1988 | Wrighton et al. | |
| 4,721,677 A | 1/1988 | Clark, Jr. | |
| 4,726,378 A | 2/1988 | Kaplan | |
| 4,726,716 A | 2/1988 | McGuire | |
| 4,731,726 A | 3/1988 | Allen, III | |
| 4,749,985 A | 6/1988 | Corsberg | |
| 4,750,496 A | 6/1988 | Reinhart | |
| 4,757,022 A | 7/1988 | Shults et al. | |
| 4,758,323 A | 7/1988 | Davis et al. | |
| 4,759,371 A | 7/1988 | Franetzki | |
| 4,759,828 A | 7/1988 | Young et al. | |
| 4,764,416 A | 8/1988 | Ueyama et al. | |
| 4,776,944 A | 10/1988 | Janata et al. | |
| 4,777,953 A | 10/1988 | Ash et al. | |
| 4,779,618 A | 10/1988 | Mund et al. | |
| 4,781,798 A | 11/1988 | Gough | |
| 4,784,736 A | 11/1988 | Lonsdale et al. | |
| 4,795,707 A | 1/1989 | Niiyama et al. | |
| 4,796,634 A | 1/1989 | Huntsman et al. | |
| 4,803,625 A | 2/1989 | Fu et al. | |
| 4,805,624 A | 2/1989 | Yao et al. | |
| 4,813,424 A | 3/1989 | Wilkins | |
| 4,815,469 A | 3/1989 | Cohen et al. | |
| 4,820,399 A | 4/1989 | Senda et al. | |
| 4,822,337 A | 4/1989 | Newhouse et al. | |
| 4,830,959 A | 5/1989 | McNeil et al. | |
| 4,832,797 A | 5/1989 | Vadgama et al. | |
| 4,835,372 A | 5/1989 | Gombrich et al. | |
| RE32,947 E | 6/1989 | Dormer et al. | |
| 4,837,049 A | 6/1989 | Byers et al. | |
| 4,840,893 A | 6/1989 | Hill et al. | |
| RE32,974 E | 7/1989 | Porat et al. | |
| 4,844,076 A | 7/1989 | Lesho et al. | |
| 4,845,035 A | 7/1989 | Fanta et al. | |
| 4,848,351 A | 7/1989 | Finch | |
| 4,854,322 A | 8/1989 | Ash et al. | |
| 4,856,340 A | 8/1989 | Garrison | |
| 4,857,713 A | 8/1989 | Brown | |
| 4,858,617 A | 8/1989 | Sanders | |
| 4,870,561 A | 9/1989 | Love et al. | |
| 4,871,351 A | 10/1989 | Feingold | |
| 4,871,440 A | 10/1989 | Nagata et al. | |
| 4,874,499 A | 10/1989 | Smith et al. | |
| 4,874,500 A | 10/1989 | Madou et al. | |
| 4,890,620 A | 1/1990 | Gough | |
| 4,890,621 A | 1/1990 | Hakky | |
| 4,894,137 A | 1/1990 | Takizawa et al. | |
| 4,897,162 A | 1/1990 | Lewandowski et al. | |
| 4,897,173 A | 1/1990 | Nankai et al. | |
| 4,899,839 A | 2/1990 | Dessertine et al. | |
| 4,909,908 A | 3/1990 | Ross et al. | |
| 4,911,794 A | 3/1990 | Parce et al. | |

| Patent No. | Date | Inventor |
|---|---|---|
| 4,917,800 A | 4/1990 | Lonsdale et al. |
| 4,919,141 A | 4/1990 | Zier et al. |
| 4,919,767 A | 4/1990 | Vadgama et al. |
| 4,920,969 A | 5/1990 | Suzuki |
| 4,920,977 A | 5/1990 | Haynes |
| 4,923,586 A | 5/1990 | Katayama et al. |
| 4,925,268 A | 5/1990 | Iyer et al. |
| 4,927,516 A | 5/1990 | Yamaguchi et al. |
| 4,931,795 A | 6/1990 | Gord |
| 4,934,369 A | 6/1990 | Maxwell |
| 4,935,105 A | 6/1990 | Churchouse |
| 4,935,345 A | 6/1990 | Guilbeau et al. |
| 4,936,956 A | 6/1990 | Wrighton |
| 4,938,860 A | 7/1990 | Wogoman |
| 4,942,127 A | 7/1990 | Wada et al. |
| 4,944,299 A | 7/1990 | Silvian |
| 4,945,045 A | 7/1990 | Forrest et al. |
| 4,950,378 A | 8/1990 | Nagata |
| 4,953,552 A | 9/1990 | DeMarzo |
| 4,954,129 A | 9/1990 | Giuliani et al. |
| 4,957,115 A | 9/1990 | Selker |
| 4,958,632 A | 9/1990 | Duggan |
| 4,968,400 A | 11/1990 | Shimomura et al. |
| 4,969,468 A | 11/1990 | Byers et al. |
| 4,970,145 A | 11/1990 | Bennetto et al. |
| 4,974,929 A | 12/1990 | Curry |
| 4,979,509 A | 12/1990 | Hakky |
| 4,986,271 A | 1/1991 | Wilkins |
| 4,990,845 A | 2/1991 | Gord |
| 4,991,582 A | 2/1991 | Byers et al. |
| 4,994,068 A | 2/1991 | Hufnagle |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,007,427 A | 4/1991 | Suzuki et al. |
| 5,016,172 A | 5/1991 | Dessertine |
| 5,016,201 A | 5/1991 | Bryan et al. |
| 5,019,974 A | 5/1991 | Beckers |
| 5,034,192 A | 7/1991 | Wrighton et al. |
| 5,035,860 A | 7/1991 | Kleingeld et al. |
| 5,036,860 A | 8/1991 | Leigh et al. |
| 5,036,861 A | 8/1991 | Sembrowich et al. |
| 5,037,527 A | 8/1991 | Hayashi et al. |
| 5,049,487 A | 9/1991 | Phillips et al. |
| 5,050,612 A | 9/1991 | Matsumura |
| 5,055,171 A | 10/1991 | Peck |
| 5,058,592 A | 10/1991 | Whisler |
| 5,063,081 A | 11/1991 | Cozzette et al. |
| 5,068,536 A | 11/1991 | Rosenthal |
| 5,070,535 A | 12/1991 | Hochmair et al. |
| 5,073,500 A | 12/1991 | Saito et al. |
| 5,077,476 A | 12/1991 | Rosenthal |
| 5,078,854 A | 1/1992 | Burgess et al. |
| 5,082,550 A | 1/1992 | Rishpon et al. |
| 5,082,786 A | 1/1992 | Nakamoto |
| 5,084,828 A | 1/1992 | Kaufman et al. |
| 5,089,112 A | 2/1992 | Skotheim et al. |
| 5,094,951 A | 3/1992 | Rosenberg |
| 5,095,904 A | 3/1992 | Seligman et al. |
| 5,096,560 A | 3/1992 | Takai et al. |
| 5,096,836 A | 3/1992 | Macho et al. |
| 5,097,834 A | 3/1992 | Skrabal |
| 5,101,814 A | 4/1992 | Palti |
| 5,106,365 A | 4/1992 | Hernandez |
| 5,108,564 A | 4/1992 | Szuminsky et al. |
| 5,109,850 A | 5/1992 | Blanco et al. |
| 5,111,539 A | 5/1992 | Hiruta et al. |
| 5,111,818 A | 5/1992 | Suzuki et al. |
| 5,114,678 A | 5/1992 | Crawford et al. |
| 5,120,420 A | 6/1992 | Nankai et al. |
| 5,120,421 A | 6/1992 | Glass et al. |
| 5,122,925 A | 6/1992 | Inpyn |
| 5,124,661 A | 6/1992 | Zelin et al. |
| 5,126,034 A | 6/1992 | Carter et al. |
| 5,126,247 A | 6/1992 | Palmer et al. |
| 5,130,009 A | 7/1992 | Marsoner et al. |
| 5,133,856 A | 7/1992 | Yamaguchi et al. |
| 5,134,391 A | 7/1992 | Okada |
| 5,135,003 A | 8/1992 | Souma |
| 5,139,023 A | 8/1992 | Stanley et al. |
| 5,140,393 A | 8/1992 | Hijikihigawa et al. |
| 5,141,868 A | 8/1992 | Shanks et al. |
| 5,161,532 A | 11/1992 | Joseph |
| 5,165,407 A | 11/1992 | Wilson et al. |
| 5,168,046 A | 12/1992 | Hamamoto et al. |
| 5,174,291 A | 12/1992 | Schoonen et al. |
| 5,176,644 A | 1/1993 | Srisathapat et al. |
| 5,176,662 A | 1/1993 | Bartholomew et al. |
| 5,182,707 A | 1/1993 | Cooper et al. |
| 5,184,359 A | 2/1993 | Tsukamura et al. |
| 5,185,256 A | 2/1993 | Nankai et al. |
| 5,190,041 A | 3/1993 | Palti |
| 5,192,415 A | 3/1993 | Yoshioka et al. |
| 5,192,416 A | 3/1993 | Wang et al. |
| 5,193,539 A | 3/1993 | Schulman et al. |
| 5,193,540 A | 3/1993 | Schulman et al. |
| 5,197,322 A | 3/1993 | Indravudh |
| 5,198,367 A | 3/1993 | Aizawa et al. |
| 5,200,051 A | 4/1993 | Cozzette et al. |
| 5,202,261 A | 4/1993 | Musho et al. |
| 5,205,920 A | 4/1993 | Oyama et al. |
| 5,206,145 A | 4/1993 | Cattell |
| 5,208,154 A | 5/1993 | Weaver et al. |
| 5,209,229 A | 5/1993 | Gilli |
| 5,215,887 A | 6/1993 | Saito |
| 5,216,597 A | 6/1993 | Beckers |
| 5,217,442 A | 6/1993 | Davis |
| 5,217,595 A | 6/1993 | Smith et al. |
| 5,227,042 A | 7/1993 | Zawodzinski et al. |
| 5,229,282 A | 7/1993 | Yoshioka et al. |
| 5,236,143 A | 8/1993 | Dragon |
| 5,237,993 A | 8/1993 | Skrabal |
| 5,245,314 A | 9/1993 | Kah et al. |
| 5,246,867 A | 9/1993 | Lakowicz et al. |
| 5,250,439 A | 10/1993 | Musho et al. |
| 5,251,126 A | 10/1993 | Kahn et al. |
| 5,257,971 A | 11/1993 | Lord et al. |
| 5,257,980 A | 11/1993 | Van Antwerp et al. |
| 5,261,401 A | 11/1993 | Baker et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,265,888 A | 11/1993 | Yamamoto et al. |
| 5,266,179 A | 11/1993 | Nankai et al. |
| 5,269,212 A | 12/1993 | Peters et al. |
| 5,271,815 A | 12/1993 | Wong |
| 5,272,060 A | 12/1993 | Hamamoto et al. |
| 5,275,159 A | 1/1994 | Griebel |
| 5,278,079 A | 1/1994 | Gubinski et al. |
| 5,279,294 A | 1/1994 | Anderson et al. |
| 5,282,950 A | 2/1994 | Dietze et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jacobson et al. |
| 5,291,887 A | 3/1994 | Stanley et al. |
| 5,293,546 A | 3/1994 | Tadros et al. |
| 5,293,877 A | 3/1994 | O'Hara et al. |
| 5,299,571 A | 4/1994 | Mastrototaro |
| 5,304,468 A | 4/1994 | Phillips et al. |
| 5,307,263 A | 4/1994 | Brown |
| 5,309,919 A | 5/1994 | Snell et al. |
| 5,310,885 A | 5/1994 | Maier et al. |
| 5,320,098 A | 6/1994 | Davidson |
| 5,320,725 A | 6/1994 | Gregg et al. |
| 5,322,063 A | 6/1994 | Allen et al. |
| 5,324,303 A | 6/1994 | Strong et al. |
| 5,324,316 A | 6/1994 | Schulman et al. |
| 5,326,449 A | 7/1994 | Cunningham |
| 5,333,615 A | 8/1994 | Craelius et al. |
| 5,337,258 A | 8/1994 | Dennis |

| | | |
|---|---|---|
| 5,337,747 A | 8/1994 | Neftel |
| 5,340,722 A | 8/1994 | Wolfbeis et al. |
| 5,342,408 A | 8/1994 | deCoriolis et al. |
| 5,342,789 A | 8/1994 | Chick et al. |
| 5,352,348 A | 10/1994 | Young et al. |
| 5,356,348 A | 10/1994 | Bellio et al. |
| 5,356,786 A | 10/1994 | Heller et al. |
| 5,358,135 A | 10/1994 | Robbins et al. |
| 5,358,514 A | 10/1994 | Schulman et al. |
| 5,360,404 A | 11/1994 | Novacek et al. |
| 5,364,797 A | 11/1994 | Olson et al. |
| 5,366,609 A | 11/1994 | White et al. |
| 5,368,028 A | 11/1994 | Palti |
| 5,370,622 A | 12/1994 | Livingston et al. |
| 5,371,687 A | 12/1994 | Holmes, II et al. |
| 5,371,734 A | 12/1994 | Fischer |
| 5,372,133 A | 12/1994 | Hogen Esch |
| 5,372,427 A | 12/1994 | Padovani et al. |
| 5,376,070 A | 12/1994 | Purvis et al. |
| 5,376,251 A | 12/1994 | Kaneko et al. |
| 5,377,258 A | 12/1994 | Bro |
| 5,378,628 A | 1/1995 | Gratzel et al. |
| 5,379,238 A | 1/1995 | Stark |
| 5,379,764 A | 1/1995 | Barnes et al. |
| 5,380,422 A | 1/1995 | Negishi et al. |
| 5,382,346 A | 1/1995 | Uenoyama et al. |
| 5,387,327 A | 2/1995 | Khan |
| 5,390,671 A | 2/1995 | Lord et al. |
| 5,391,250 A | 2/1995 | Cheney, II et al. |
| 5,393,903 A | 2/1995 | Gratzel et al. |
| 5,395,504 A | 3/1995 | Saurer et al. |
| 5,399,823 A | 3/1995 | McCusker |
| 5,400,782 A | 3/1995 | Beaubiah |
| 5,400,794 A | 3/1995 | Gorman |
| 5,408,999 A | 4/1995 | Singh et al. |
| 5,410,326 A | 4/1995 | Goldstein |
| 5,410,471 A | 4/1995 | Alyfuku et al. |
| 5,410,474 A | 4/1995 | Fox |
| 5,411,647 A | 5/1995 | Johnson et al. |
| 5,413,690 A | 5/1995 | Kost et al. |
| 5,422,246 A | 6/1995 | Koopal et al. |
| 5,425,868 A | 6/1995 | Pedersen |
| 5,431,160 A | 7/1995 | Wilkins |
| 5,431,691 A | 7/1995 | Snell et al. |
| 5,431,921 A | 7/1995 | Thombre |
| 5,433,710 A | 7/1995 | Van Antwerp et al. |
| 5,437,973 A | 8/1995 | Vadgama et al. |
| 5,437,999 A | 8/1995 | Diebold et al. |
| 5,438,271 A | 8/1995 | White et al. |
| 5,445,611 A | 8/1995 | Eppstein et al. |
| 5,445,920 A | 8/1995 | Saito |
| 5,456,692 A | 10/1995 | Smith, Jr. et al. |
| 5,456,940 A | 10/1995 | Funderburk |
| 5,458,140 A | 10/1995 | Eppstein et al. |
| 5,460,618 A | 10/1995 | Harreld |
| 5,462,525 A | 10/1995 | Srisathapat et al. |
| 5,462,645 A | 10/1995 | Albery et al. |
| 5,466,218 A | 11/1995 | Srisathapat et al. |
| 5,467,778 A | 11/1995 | Catt et al. |
| 5,469,846 A | 11/1995 | Khan |
| 5,472,317 A | 12/1995 | Field et al. |
| 5,476,460 A | 12/1995 | Montalvo |
| 5,477,855 A | 12/1995 | Schindler et al. |
| 5,482,473 A | 1/1996 | Lord et al. |
| 5,484,404 A | 1/1996 | Schulman et al. |
| 5,487,751 A | 1/1996 | Radons et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,501,956 A | 3/1996 | Wada et al. |
| 5,505,709 A | 4/1996 | Funderburk |
| 5,505,713 A | 4/1996 | Van Antwerp et al. |
| 5,507,288 A | 4/1996 | Bocker et al. |
| 5,508,171 A | 4/1996 | Walling et al. |
| 5,509,410 A | 4/1996 | Hill et al. |
| 5,514,103 A | 5/1996 | Srisathapat et al. |
| 5,514,253 A | 5/1996 | Davis et al. |
| 5,514,718 A | 5/1996 | Lewis et al. |
| 5,518,006 A | 5/1996 | Mawhirt et al. |
| 5,520,787 A | 5/1996 | Hanagan et al. |
| 5,522,865 A | 6/1996 | Schulman et al. |
| 5,525,511 A | 6/1996 | D'Costa |
| 5,526,120 A | 6/1996 | Jina et al. |
| 5,527,307 A | 6/1996 | Srisathapat et al. |
| 5,529,676 A | 6/1996 | Maley et al. |
| 5,531,878 A | 7/1996 | Vadgama et al. |
| 5,538,511 A | 7/1996 | Van Antwerp |
| 5,544,196 A | 8/1996 | Tiedemann, Jr. et al. |
| 5,545,152 A | 8/1996 | Funderburk et al. |
| 5,545,191 A | 8/1996 | Mann et al. |
| 5,549,113 A | 8/1996 | Halleck et al. |
| 5,549,115 A | 8/1996 | Morgan et al. |
| 5,552,027 A | 9/1996 | Birkle et al. |
| 5,554,166 A | 9/1996 | Lange et al. |
| 5,556,524 A | 9/1996 | Albers |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,569,212 A | 10/1996 | Brown |
| 5,573,647 A | 11/1996 | Maley et al. |
| 5,575,895 A | 11/1996 | Ikeda et al. |
| 5,580,527 A | 12/1996 | Bell et al. |
| 5,580,794 A | 12/1996 | Allen |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,594,906 A | 1/1997 | Holmes, II et al. |
| 5,596,150 A | 1/1997 | Arndt et al. |
| 5,596,994 A | 1/1997 | Bro |
| 5,600,301 A | 2/1997 | Robinson, III |
| 5,601,435 A | 2/1997 | Quy |
| 5,601,694 A | 2/1997 | Maley et al. |
| 5,605,152 A | 2/1997 | Slate et al. |
| 5,609,575 A | 3/1997 | Larson et al. |
| 5,611,900 A | 3/1997 | Worden et al. |
| 5,615,135 A | 3/1997 | Waclawsky et al. |
| 5,615,671 A | 4/1997 | Schoonen et al. |
| 5,616,222 A | 4/1997 | Maley et al. |
| 5,617,851 A | 4/1997 | Lipkovker |
| 5,623,925 A | 4/1997 | Swenson et al. |
| 5,623,933 A | 4/1997 | Amano et al. |
| 5,628,309 A | 5/1997 | Brown |
| 5,628,310 A | 5/1997 | Rao et al. |
| 5,628,890 A | 5/1997 | Carter et al. |
| 5,629,981 A | 5/1997 | Nerlikar |
| 5,637,095 A | 6/1997 | Nason et al. |
| 5,640,764 A | 6/1997 | Strojnik |
| 5,640,954 A | 6/1997 | Pfeiffer et al. |
| 5,643,212 A | 7/1997 | Coutre et al. |
| 5,647,853 A | 7/1997 | Feldmann et al. |
| 5,650,062 A | 7/1997 | Ikeda et al. |
| 5,651,767 A | 7/1997 | Schulman et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,065 A | 9/1997 | Colman et al. |
| 5,665,222 A | 9/1997 | Heller et al. |
| 5,667,983 A | 9/1997 | Abel et al. |
| 5,670,031 A | 9/1997 | Hintsche et al. |
| 5,678,571 A | 10/1997 | Brown |
| 5,679,690 A | 10/1997 | Andre et al. |
| 5,680,858 A | 10/1997 | Hansen et al. |
| 5,682,233 A | 10/1997 | Brinda |
| 5,686,717 A | 11/1997 | Knowles et al. |
| 5,695,623 A | 12/1997 | Michel et al. |
| 5,695,949 A | 12/1997 | Galen et al. |
| 5,701,894 A | 12/1997 | Cherry et al. |

| | | | | | | |
|---|---|---|---|---|---|---|
| 5,704,922 A | 1/1998 | Brown | | 5,887,133 A | 3/1999 | Brown et al. |
| 5,707,502 A | 1/1998 | McCaffrey et al. | | 5,897,493 A | 4/1999 | Brown |
| 5,708,247 A | 1/1998 | McAleer et al. | | 5,898,025 A | 4/1999 | Burg et al. |
| 5,710,630 A | 1/1998 | Essenpreis et al. | | 5,899,855 A | 5/1999 | Brown |
| 5,711,001 A | 1/1998 | Bussan et al. | | 5,913,310 A | 6/1999 | Brown |
| 5,711,297 A | 1/1998 | Iliff et al. | | 5,917,346 A | 6/1999 | Gord |
| 5,711,861 A | 1/1998 | Ward et al. | | 5,918,603 A | 7/1999 | Brown |
| 5,711,862 A | 1/1998 | Sakoda et al. | | 5,925,021 A | 7/1999 | Castellano et al. |
| 5,711,868 A | 1/1998 | Maley et al. | | 5,931,791 A | 8/1999 | Saltzstein et al. |
| 5,718,234 A | 2/1998 | Warden et al. | | 5,933,136 A | 8/1999 | Brown |
| 5,720,733 A | 2/1998 | Brown | | 5,935,224 A | 8/1999 | Svancarek et al. |
| 5,720,862 A | 2/1998 | Hamamoto et al. | | 5,939,609 A | 8/1999 | Knapp et al. |
| 5,721,783 A | 2/1998 | Anderson | | 5,940,801 A | 8/1999 | Brown |
| 5,722,397 A | 3/1998 | Eppstein | | 5,942,979 A | 8/1999 | Luppino |
| 5,727,548 A | 3/1998 | Hill et al. | | 5,945,345 A | 8/1999 | Blatt et al. |
| 5,730,124 A | 3/1998 | Yamauchi | | 5,947,921 A | 9/1999 | Johnson et al. |
| 5,730,654 A | 3/1998 | Brown | | 5,948,512 A | 9/1999 | Kubota et al. |
| 5,735,273 A | 4/1998 | Kurnik et al. | | 5,950,632 A | 9/1999 | Reber et al. |
| 5,735,285 A | 4/1998 | Albert et al. | | 5,951,300 A | 9/1999 | Brown |
| 5,741,211 A | 4/1998 | Renirie et al. | | 5,951,492 A | 9/1999 | Douglas et al. |
| 5,741,688 A | 4/1998 | Oxenboll et al. | | 5,951,521 A | 9/1999 | Mastrototaro et al. |
| 5,746,217 A | 5/1998 | Erickson et al. | | 5,951,836 A | 9/1999 | McAleer et al. |
| 5,748,103 A | 5/1998 | Flach et al. | | 5,954,643 A | 9/1999 | Van Antwerp |
| 5,750,926 A | 5/1998 | Schulman et al. | | 5,954,685 A | 9/1999 | Tierney |
| 5,758,290 A | 5/1998 | Nealon et al. | | 5,954,700 A | 9/1999 | Kovelman |
| 5,770,028 A | 6/1998 | Maley et al. | | 5,956,501 A | 9/1999 | Brown |
| 5,771,001 A | 6/1998 | Cobb | | 5,957,854 A | 9/1999 | Besson et al. |
| 5,771,890 A | 6/1998 | Tamada | | 5,957,890 A | 9/1999 | Mann et al. |
| 5,772,586 A | 6/1998 | Heinonen et al. | | 5,957,958 A | 9/1999 | Schulman et al. |
| 5,777,060 A | 7/1998 | Van Antwerp | | 5,960,403 A | 9/1999 | Brown |
| 5,779,665 A | 7/1998 | Mastrototaro et al. | | 5,961,451 A | 10/1999 | Reber et al. |
| 5,781,024 A | 7/1998 | Blomberg et al. | | 5,964,993 A | 10/1999 | Blubaugh, Jr. et al. |
| 5,782,814 A | 7/1998 | Brown et al. | | 5,965,380 A | 10/1999 | Heller et al. |
| 5,785,681 A | 7/1998 | Indravudh | | 5,968,839 A | 10/1999 | Blatt et al. |
| 5,786,439 A | 7/1998 | Van Antwerp et al. | | 5,971,922 A | 10/1999 | Arita et al. |
| 5,786,584 A | 7/1998 | Button et al. | | 5,971,941 A | 10/1999 | Simons et al. |
| 5,788,678 A | 8/1998 | Van Antwerp | | 5,974,124 A | 10/1999 | Schlueter, Jr. et al. |
| 5,791,344 A | 8/1998 | Schulman et al. | | 5,977,476 A | 11/1999 | Guha et al. |
| 5,792,117 A | 8/1998 | Brown | | 5,981,294 A | 11/1999 | Blatt et al. |
| 5,793,292 A | 8/1998 | Ivey | | 5,989,409 A | 11/1999 | Kurnik et al. |
| 5,800,420 A | 9/1998 | Gross et al. | | 5,994,476 A | 11/1999 | Shin et al. |
| 5,804,048 A | 9/1998 | Wong et al. | | 5,995,860 A | 11/1999 | Sun et al. |
| 5,807,315 A | 9/1998 | Van Antwerp et al. | | 5,997,476 A | 12/1999 | Brown |
| 5,807,375 A | 9/1998 | Gross et al. | | 5,999,848 A | 12/1999 | Gord et al. |
| 5,814,599 A | 9/1998 | Mitragotri et al. | | 5,999,849 A | 12/1999 | Gord et al. |
| 5,820,551 A | 10/1998 | Hill et al. | | 6,001,067 A | 12/1999 | Shults et al. |
| 5,820,570 A | 10/1998 | Erickson et al. | | 6,002,954 A | 12/1999 | Van Antwerp et al. |
| 5,820,622 A | 10/1998 | Gross et al. | | 6,002,961 A | 12/1999 | Mitragotri et al. |
| 5,822,715 A | 10/1998 | Worthington et al. | | 6,004,441 A | 12/1999 | Fujiwara et al. |
| 5,825,488 A | 10/1998 | Kohl et al. | | 6,011,984 A | 1/2000 | Van Antwerp et al. |
| 5,827,179 A | 10/1998 | Lichter et al. | | 6,014,577 A | 1/2000 | Henning et al. |
| 5,827,183 A | 10/1998 | Kurnik et al. | | 6,018,678 A | 1/2000 | Mitragotri et al. |
| 5,827,184 A | 10/1998 | Netherly et al. | | 6,023,629 A | 2/2000 | Tamada |
| 5,828,943 A | 10/1998 | Brown | | 6,024,699 A | 2/2000 | Surwit et al. |
| 5,830,064 A | 11/1998 | Bradish et al. | | 6,026,320 A | 2/2000 | Carlson et al. |
| 5,830,341 A | 11/1998 | Gilmartin | | 6,027,459 A | 2/2000 | Shain et al. |
| 5,832,448 A | 11/1998 | Brown | | 6,027,692 A | 2/2000 | Galen et al. |
| 5,834,224 A | 11/1998 | Ruger et al. | | 6,032,059 A | 2/2000 | Henning et al. |
| 5,837,454 A | 11/1998 | Cozzette et al. | | 6,032,199 A | 2/2000 | Lim et al. |
| 5,837,546 A | 11/1998 | Allen et al. | | 6,033,866 A | 3/2000 | Guo et al. |
| 5,840,020 A | 11/1998 | Heinonen et al. | | 6,035,237 A | 3/2000 | Schulman et al. |
| 5,842,983 A | 12/1998 | Abel et al. | | 6,040,194 A | 3/2000 | Chick et al. |
| 5,843,140 A | 12/1998 | Strojnik | | 6,041,253 A | 3/2000 | Kost et al. |
| 5,846,702 A | 12/1998 | Deng et al. | | 6,043,437 A | 3/2000 | Schulman et al. |
| 5,846,744 A | 12/1998 | Athey et al. | | 6,049,727 A | 4/2000 | Crothall |
| 5,851,197 A | 12/1998 | Marano et al. | | 6,052,565 A | 4/2000 | Ishikura et al. |
| 5,854,078 A | 12/1998 | Asher et al. | | D424,696 S | 5/2000 | Ray et al. |
| 5,854,189 A | 12/1998 | Kruse et al. | | 6,056,718 A | 5/2000 | Funderburk et al. |
| 5,856,758 A | 1/1999 | Joffe et al. | | 6,063,459 A | 5/2000 | Velte |
| 5,857,967 A | 1/1999 | Frid et al. | | 6,066,243 A | 5/2000 | Anderson et al. |
| 5,857,983 A | 1/1999 | Douglas et al. | | 6,067,474 A | 5/2000 | Schulman et al. |
| 5,860,917 A | 1/1999 | Comanor et al. | | 6,068,615 A | 5/2000 | Brown et al. |
| 5,872,713 A | 2/1999 | Douglas et al. | | D426,638 S | 6/2000 | Ray et al. |
| 5,876,484 A | 3/1999 | Raskin et al. | | D427,312 S | 6/2000 | Douglas |
| 5,879,163 A | 3/1999 | Brown et al. | | 6,071,249 A | 6/2000 | Cunningham et al. |
| 5,879,311 A | 3/1999 | Duchon et al. | | 6,071,251 A | 6/2000 | Cunningham et al. |
| 5,880,829 A | 3/1999 | Kauhaniemi et al. | | 6,071,294 A | 6/2000 | Simons et al. |
| 5,882,494 A | 3/1999 | Van Antwerp | | 6,071,391 A | 6/2000 | Gotoh et al. |
| 5,885,211 A | 3/1999 | Eppstein et al. | | 6,073,031 A | 6/2000 | Helstab et al. |

| | | | |
|---|---|---|---|
| 6,081,736 A | 6/2000 | Colvin et al. | |
| 6,083,710 A | 7/2000 | Heller et al. | |
| 6,088,608 A | 7/2000 | Schulman et al. | |
| 6,091,975 A | 7/2000 | Daddona et al. | |
| 6,091,976 A | 7/2000 | Pfeiffer et al. | |
| 6,093,156 A | 7/2000 | Cunningham et al. | |
| 6,093,167 A | 7/2000 | Houben et al. | |
| 6,093,172 A | 7/2000 | Funderburk et al. | |
| 6,097,480 A | 8/2000 | Kaplan | |
| 6,097,831 A | 8/2000 | Wieck et al. | |
| 6,099,484 A | 8/2000 | Douglas et al. | |
| 6,101,478 A | 8/2000 | Brown | |
| 6,103,033 A | 8/2000 | Say et al. | |
| 6,106,780 A | 8/2000 | Douglas et al. | |
| 6,110,148 A | 8/2000 | Brown et al. | |
| 6,110,152 A | 8/2000 | Kovelman | |
| 6,113,578 A | 9/2000 | Brown | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,125,978 A | 10/2000 | Ando et al. | |
| 6,134,461 A | 10/2000 | Say et al. | |
| 6,134,504 A | 10/2000 | Douglas et al. | |
| 6,139,718 A | 10/2000 | Kurnik et al. | |
| 6,141,573 A | 10/2000 | Kurnik et al. | |
| 6,142,939 A | 11/2000 | Eppstein et al. | |
| 6,143,164 A | 11/2000 | Heller et al. | |
| 6,144,837 A | 11/2000 | Quy | |
| 6,144,869 A | 11/2000 | Berner et al. | |
| 6,144,922 A | 11/2000 | Douglas et al. | |
| 6,148,094 A | 11/2000 | Kinsella | |
| 6,150,128 A | 11/2000 | Uretsky | |
| 6,151,586 A | 11/2000 | Brown | |
| 6,153,062 A | 11/2000 | Saito et al. | |
| 6,153,069 A | 11/2000 | Pottgen et al. | |
| 6,159,147 A | 12/2000 | Lichter et al. | |
| 6,161,095 A | 12/2000 | Brown | |
| 6,162,611 A | 12/2000 | Heller et al. | |
| 6,162,639 A | 12/2000 | Douglas | |
| 6,164,284 A | 12/2000 | Schulman et al. | |
| 6,167,362 A | 12/2000 | Brown et al. | |
| 6,168,563 B1 | 1/2001 | Brown | |
| 6,170,318 B1 | 1/2001 | Lewis | |
| 6,175,752 B1 | 1/2001 | Say et al. | |
| 6,180,416 B1 | 1/2001 | Kurnik et al. | |
| 6,186,145 B1 | 2/2001 | Brown | |
| 6,192,891 B1 | 2/2001 | Gravel et al. | |
| 6,193,873 B1 | 2/2001 | Ohara et al. | |
| D439,242 S | 3/2001 | Brown et al. | |
| 6,196,970 B1 | 3/2001 | Brown | |
| 6,198,957 B1 | 3/2001 | Green | |
| 6,200,265 B1 | 3/2001 | Walsh et al. | |
| 6,201,979 B1 | 3/2001 | Kurnik et al. | |
| 6,201,980 B1 | 3/2001 | Darrow et al. | |
| 6,203,495 B1 | 3/2001 | Bardy | |
| 6,206,841 B1 | 3/2001 | Cunningham et al. | |
| 6,207,400 B1 | 3/2001 | Kwon | |
| 6,208,894 B1 | 3/2001 | Schulman et al. | |
| 6,210,272 B1 | 4/2001 | Brown | |
| 6,210,976 B1 | 4/2001 | Sabbadini | |
| 6,212,416 B1 | 4/2001 | Ward et al. | |
| 6,219,565 B1 | 4/2001 | Cupp et al. | |
| 6,219,574 B1 | 4/2001 | Cormier et al. | |
| 6,224,745 B1 | 5/2001 | Baltruschat | |
| 6,232,130 B1 | 5/2001 | Wolf | |
| 6,232,370 B1 | 5/2001 | Kubota et al. | |
| 6,233,471 B1 | 5/2001 | Berner et al. | |
| 6,233,539 B1 | 5/2001 | Brown | |
| 6,239,925 B1 | 5/2001 | Ardrey et al. | |
| 6,241,862 B1 | 6/2001 | McAleer et al. | |
| 6,246,330 B1 | 6/2001 | Nielsen | |
| 6,246,992 B1 | 6/2001 | Brown | |
| 6,248,065 B1 | 6/2001 | Brown | |
| 6,248,067 B1 | 6/2001 | Causey, III et al. | |
| 6,248,093 B1 | 6/2001 | Moberg | |
| 6,251,260 B1 | 6/2001 | Heller et al. | |
| 6,252,032 B1 | 6/2001 | Van Antwerp et al. | |
| 6,253,804 B1 | 7/2001 | Safabash | |
| 6,254,586 B1 | 7/2001 | Mann et al. | |
| 6,256,643 B1 | 7/2001 | Cork et al. | |
| 6,259,587 B1 | 7/2001 | Sheldon et al. | |
| 6,259,937 B1 | 7/2001 | Schulman et al. | |
| 6,260,022 B1 | 7/2001 | Brown | |
| 6,266,645 B1 | 7/2001 | Simpson | |
| 6,267,724 B1 | 7/2001 | Taylor | |
| 6,268,161 B1 | 7/2001 | Han et al. | |
| 6,270,445 B1 | 8/2001 | Dean, Jr. et al. | |
| 6,272,364 B1 | 8/2001 | Kurnik | |
| 6,275,717 B1 | 8/2001 | Gross et al. | |
| 6,280,416 B1 | 8/2001 | Van Antwerp et al. | |
| 6,280,587 B1 | 8/2001 | Matsumoto | |
| 6,281,006 B1 | 8/2001 | Heller et al. | |
| 6,283,943 B1 | 9/2001 | Dy et al. | |
| 6,284,126 B1 | 9/2001 | Kurnik et al. | |
| 6,284,478 B1 | 9/2001 | Heller et al. | |
| 6,293,925 B1 | 9/2001 | Safabash et al. | |
| 6,294,281 B1 | 9/2001 | Heller | |
| 6,295,463 B1 | 9/2001 | Stenzler | |
| 6,295,506 B1 | 9/2001 | Heinonen et al. | |
| 6,298,254 B2 | 10/2001 | Tamada | |
| 6,299,578 B1 | 10/2001 | Kurnik et al. | |
| 6,299,757 B1 | 10/2001 | Feldman et al. | |
| 6,301,499 B1 | 10/2001 | Carlson et al. | |
| 6,304,766 B1 | 10/2001 | Colvin, Jr. | |
| 6,306,104 B1 | 10/2001 | Cunningham et al. | |
| 6,307,867 B1 | 10/2001 | Roobol et al. | |
| 6,309,351 B1 | 10/2001 | Kurnik et al. | |
| 6,309,884 B1 | 10/2001 | Cooper et al. | |
| 6,313,749 B1 | 11/2001 | Horne et al. | |
| 6,315,721 B2 | 11/2001 | Schulman et al. | |
| 6,319,540 B1 | 11/2001 | Van Antwerp et al. | |
| 6,326,160 B1 | 12/2001 | Dunn et al. | |
| 6,329,161 B1 | 12/2001 | Heller et al. | |
| 6,329,929 B1 | 12/2001 | Weijand et al. | |
| 6,330,426 B2 | 12/2001 | Brown et al. | |
| 6,330,464 B1 | 12/2001 | Colvin, Jr. et al. | |
| 6,331,518 B2 | 12/2001 | Hemm et al. | |
| 6,334,778 B1 | 1/2002 | Brown | |
| 6,336,900 B1 | 1/2002 | Alleckson et al. | |
| 6,338,790 B1 | 1/2002 | Feldman et al. | |
| 6,340,421 B1 | 1/2002 | Vachon et al. | |
| 6,341,232 B1 | 1/2002 | Conn et al. | |
| 6,356,776 B1 | 3/2002 | Berner et al. | |
| 6,360,888 B1 | 3/2002 | McIvor et al. | |
| 6,366,793 B1 | 4/2002 | Bell et al. | |
| 6,366,794 B1 | 4/2002 | Moussy et al. | |
| 6,368,141 B1 | 4/2002 | VanAntwerp et al. | |
| 6,368,274 B1 | 4/2002 | Van Antwerp et al. | |
| 6,370,410 B2 | 4/2002 | Kurnik et al. | |
| 6,377,828 B1 | 4/2002 | Chaiken et al. | |
| 6,379,301 B1 | 4/2002 | Worthington et al. | |
| 6,383,767 B1 | 5/2002 | Polak | |
| 6,387,048 B1 | 5/2002 | Schulman et al. | |
| 6,391,643 B1 | 5/2002 | Chen et al. | |
| 6,393,318 B1 | 5/2002 | Conn et al. | |
| 6,398,562 B1 | 6/2002 | Butler et al. | |
| 6,405,066 B1 | 6/2002 | Essenpreis et al. | |
| 6,413,393 B1 | 7/2002 | Van Antwerp et al. | |
| 6,416,471 B1 | 7/2002 | Kumar et al. | |
| 6,418,332 B1 | 7/2002 | Mastrototaro et al. | |
| 6,424,847 B1 | 7/2002 | Mastrototaro et al. | |
| 6,427,088 B1 | 7/2002 | Bowman, IV et al. | |
| 6,434,409 B1 | 8/2002 | Pfeiffer et al. | |
| 6,438,414 B1 | 8/2002 | Conn et al. | |
| 6,440,068 B1 | 8/2002 | Brown et al. | |
| 6,442,637 B1 | 8/2002 | Hawkins et al. | |
| 6,443,942 B2 | 9/2002 | Van Antwerp et al. | |
| 6,449,255 B1 | 9/2002 | Waclawsky et al. | |
| 6,454,710 B1 | 9/2002 | Ballerstadt et al. | |
| 6,462,162 B2 | 10/2002 | Van Antwerp et al. | |
| 6,464,848 B1 | 10/2002 | Matsumoto | |
| 6,466,810 B1 | 10/2002 | Ward et al. | |
| 6,468,222 B1 | 10/2002 | Mault et al. | |
| 6,472,122 B1 | 10/2002 | Schulman et al. | |
| 6,475,750 B1 | 11/2002 | Han et al. | |

| Patent No. | Date | Inventor |
|---|---|---|
| 6,477,395 B2 | 11/2002 | Schulman et al. |
| 6,478,736 B1 | 11/2002 | Mault |
| 6,480,730 B2 | 11/2002 | Darrow et al. |
| 6,482,156 B2 | 11/2002 | Iliff |
| 6,482,158 B2 | 11/2002 | Mault |
| 6,482,604 B2 | 11/2002 | Kwon |
| 6,484,045 B1 | 11/2002 | Holker et al. |
| 6,484,046 B1 | 11/2002 | Say et al. |
| 6,485,138 B1 | 11/2002 | Kubota et al. |
| 6,494,830 B1 | 12/2002 | Wessel |
| 6,496,728 B2 | 12/2002 | Li et al. |
| 6,505,059 B1 | 1/2003 | Kollias et al. |
| 6,505,121 B1 | 1/2003 | Russell |
| 6,512,939 B1 | 1/2003 | Colvin et al. |
| 6,513,532 B2 | 2/2003 | Mault et al. |
| 6,514,718 B2 | 2/2003 | Heller et al. |
| 6,515,593 B1 | 2/2003 | Stark et al. |
| 6,520,326 B2 | 2/2003 | McIvor et al. |
| 6,529,755 B2 | 3/2003 | Kurnik et al. |
| 6,529,772 B2 | 3/2003 | Carlson et al. |
| 6,530,915 B2 | 3/2003 | Eppstein et al. |
| 6,534,322 B1 | 3/2003 | Sabbadini |
| 6,534,323 B1 | 3/2003 | Sabbadini |
| 6,535,753 B1 | 3/2003 | Raskas |
| 6,537,243 B1 | 3/2003 | Henning et al. |
| 6,540,675 B2 | 4/2003 | Aceti et al. |
| 6,541,266 B2 | 4/2003 | Modzelewski et al. |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,551,494 B1 | 4/2003 | Heller et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,571,128 B2 | 5/2003 | Lebel et al. |
| 6,571,200 B1 | 5/2003 | Mault |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,587,705 B1 | 7/2003 | Kim et al. |
| 6,591,125 B1 | 7/2003 | Buse et al. |
| 6,591,126 B2 | 7/2003 | Roeper et al. |
| 6,594,514 B2 | 7/2003 | Berner et al. |
| 6,595,919 B2 | 7/2003 | Berner et al. |
| 6,595,929 B2 | 7/2003 | Stivoric et al. |
| 6,602,678 B2 | 8/2003 | Kwon et al. |
| 6,602,909 B1 | 8/2003 | Jarowski |
| 6,605,200 B1 | 8/2003 | Mao et al. |
| 6,605,201 B1 | 8/2003 | Mao et al. |
| 6,607,509 B2 | 8/2003 | Bobroff et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,612,306 B1 | 9/2003 | Mault |
| 6,615,078 B1 | 9/2003 | Burson et al. |
| 6,616,613 B1 | 9/2003 | Goodman |
| 6,618,603 B2 | 9/2003 | Varalli et al. |
| 6,620,106 B2 | 9/2003 | Mault |
| 6,627,058 B1 | 9/2003 | Chan |
| 6,627,154 B1 | 9/2003 | Goodman et al. |
| 6,629,934 B2 | 10/2003 | Mault et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,642,015 B2 | 11/2003 | Vachon et al. |
| 6,645,142 B2 | 11/2003 | Braig et al. |
| 6,645,368 B1 | 11/2003 | Beaty et al. |
| 6,648,821 B2 | 11/2003 | Lebel et al. |
| 6,653,091 B1 | 11/2003 | Dunn et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,671,554 B2 | 12/2003 | Gibson et al. |
| 6,673,625 B2 | 1/2004 | Satcher, Jr. et al. |
| 6,682,938 B1 | 1/2004 | Satcher, Jr. et al. |
| 6,683,040 B2 | 1/2004 | Bragulla et al. |
| 6,687,522 B2 | 2/2004 | Tamada |
| 6,687,546 B2 | 2/2004 | Lebel et al. |
| 6,689,056 B1 | 2/2004 | Kilcoyne et al. |
| 6,690,276 B1 | 2/2004 | Marino |
| 6,693,069 B2 | 2/2004 | Korber et al. |
| 6,694,158 B2 | 2/2004 | Polak |
| 6,694,191 B2 | 2/2004 | Starkweather et al. |
| 6,695,860 B1 | 2/2004 | Ward et al. |
| 6,698,269 B2 | 3/2004 | Barber et al. |
| 6,701,270 B1 | 3/2004 | Miller et al. |
| 6,702,857 B2 | 3/2004 | Brauker et al. |
| 6,704,587 B1 | 3/2004 | Kumar et al. |
| 6,708,057 B2 | 3/2004 | Morganroth |
| 6,711,423 B2 | 3/2004 | Colvin, Jr. |
| 6,723,046 B2 | 4/2004 | Lichtenstein et al. |
| 6,728,560 B2 | 4/2004 | Kollias et al. |
| 6,731,976 B2 | 5/2004 | Penn et al. |
| 6,733,446 B2 | 5/2004 | Lebel et al. |
| 6,734,162 B2 | 5/2004 | Van Antwerp et al. |
| 6,735,479 B2 | 5/2004 | Fabian et al. |
| 6,736,777 B2 | 5/2004 | Kim et al. |
| 6,736,797 B1 | 5/2004 | Larsen et al. |
| 6,737,401 B2 | 5/2004 | Kim et al. |
| 6,738,654 B2 | 5/2004 | Sohrab |
| 6,740,075 B2 | 5/2004 | Lebel et al. |
| 6,741,163 B1 | 5/2004 | Roberts |
| 6,741,876 B1 | 5/2004 | Scecina et al. |
| 6,741,877 B1 | 5/2004 | Shults et al. |
| 6,746,582 B2 | 6/2004 | Heller et al. |
| 6,748,445 B1 | 6/2004 | Darcy et al. |
| 6,749,587 B2 | 6/2004 | Flaherty |
| 6,750,311 B1 | 6/2004 | Van Antwerp et al. |
| 6,758,810 B2 | 7/2004 | Lebel et al. |
| 6,766,183 B2 | 7/2004 | Walsh et al. |
| 6,766,201 B2 | 7/2004 | Von Arx et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,771,995 B2 | 8/2004 | Kurnik et al. |
| 6,773,563 B2 | 8/2004 | Matsumoto |
| 6,780,156 B2 | 8/2004 | Haueter et al. |
| 6,780,297 B2 | 8/2004 | Matsumoto et al. |
| 6,780,871 B2 | 8/2004 | Glick et al. |
| 6,784,274 B2 | 8/2004 | Van Antwerp et al. |
| 6,790,178 B1 | 9/2004 | Mault et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| 6,809,507 B2 | 10/2004 | Morgan et al. |
| 6,809,653 B1 | 10/2004 | Mann et al. |
| 6,810,290 B2 | 10/2004 | Lebel et al. |
| 6,810,309 B2 | 10/2004 | Sadler et al. |
| 6,811,533 B2 | 11/2004 | Lebel et al. |
| 6,811,534 B2 | 11/2004 | Bowman, IV et al. |
| 6,811,659 B2 | 11/2004 | Vachon |
| 6,812,031 B1 | 11/2004 | Carlsson |
| 6,813,519 B2 | 11/2004 | Lebel et al. |
| 6,816,742 B2 | 11/2004 | Kim et al. |
| 6,835,553 B2 | 12/2004 | Han et al. |
| RE38,681 E | 1/2005 | Kurnik et al. |
| 6,840,912 B2 | 1/2005 | Kloepfer et al. |
| 6,844,023 B2 | 1/2005 | Schulman et al. |
| 6,849,237 B2 | 2/2005 | Housefield et al. |
| 6,850,790 B2 | 2/2005 | Berner et al. |
| 6,852,104 B2 | 2/2005 | Blomquist |
| 6,852,500 B1 | 2/2005 | Hoss et al. |
| 6,852,694 B2 | 2/2005 | Van Antwerp et al. |
| 6,853,854 B1 | 2/2005 | Proniewicz et al. |
| 6,856,928 B2 | 2/2005 | Harmon |

| Patent No. | Date | Inventor |
|---|---|---|
| 6,858,403 B2 | 2/2005 | Han et al. |
| 6,862,465 B2 | 3/2005 | Shults et al. |
| 6,862,466 B2 | 3/2005 | Ackerman |
| 6,872,200 B2 | 3/2005 | Mann et al. |
| 6,873,268 B2 | 3/2005 | Lebel et al. |
| 6,881,551 B2 | 4/2005 | Heller et al. |
| 6,882,940 B2 | 4/2005 | Potts et al. |
| 6,885,883 B2 | 4/2005 | Parris et al. |
| 6,892,085 B2 | 5/2005 | McIvor et al. |
| 6,895,263 B2 | 5/2005 | Shin et al. |
| 6,895,265 B2 | 5/2005 | Silver |
| 6,899,683 B2 | 5/2005 | Mault et al. |
| 6,899,684 B2 | 5/2005 | Mault et al. |
| 6,902,207 B2 | 6/2005 | Lickliter |
| 6,902,905 B2 | 6/2005 | Burson et al. |
| 6,904,301 B2 | 6/2005 | Raskas |
| 6,907,127 B1 | 6/2005 | Kravitz et al. |
| 6,915,147 B2 | 7/2005 | Lebel et al. |
| 6,918,874 B1 | 7/2005 | Hatch et al. |
| 6,922,578 B2 | 7/2005 | Eppstein et al. |
| RE38,775 E | 8/2005 | Kurnik et al. |
| 6,923,764 B2 | 8/2005 | Aceti et al. |
| 6,923,936 B2 | 8/2005 | Swanson et al. |
| 6,927,246 B2 | 8/2005 | Noronha et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,936,029 B2 | 8/2005 | Mann et al. |
| 6,937,222 B2 | 8/2005 | Numao |
| 6,940,590 B2 | 9/2005 | Colvin, Jr. et al. |
| 6,941,163 B2 | 9/2005 | Ford et al. |
| 6,950,708 B2 | 9/2005 | Bowman, IV et al. |
| 6,952,603 B2 | 10/2005 | Gerber et al. |
| 6,954,673 B2 | 10/2005 | Von Arx et al. |
| 6,955,650 B2 | 10/2005 | Mault et al. |
| 6,957,102 B2 | 10/2005 | Silver et al. |
| 6,957,107 B2 | 10/2005 | Rogers et al. |
| 6,958,705 B2 | 10/2005 | Lebel et al. |
| 6,968,294 B2 | 11/2005 | Gutta et al. |
| 6,968,375 B1 | 11/2005 | Brown |
| 6,971,274 B2 | 12/2005 | Olin |
| 6,974,437 B2 | 12/2005 | Lebel et al. |
| 6,978,182 B2 | 12/2005 | Mazar et al. |
| 6,979,326 B2 | 12/2005 | Mann et al. |
| 6,985,870 B2 | 1/2006 | Martucci et al. |
| 6,990,366 B2 | 1/2006 | Say et al. |
| 6,991,096 B2 | 1/2006 | Gottlieb et al. |
| 6,997,907 B2 | 2/2006 | Safabash et al. |
| 6,997,920 B2 | 2/2006 | Mann et al. |
| 6,998,247 B2 | 2/2006 | Monfre et al. |
| 6,999,810 B2 | 2/2006 | Berner et al. |
| 7,003,336 B2 | 2/2006 | Holker et al. |
| 7,003,340 B2 | 2/2006 | Say et al. |
| 7,003,341 B2 | 2/2006 | Say et al. |
| 7,004,901 B2 | 2/2006 | Fish |
| 7,005,857 B2 | 2/2006 | Stiene et al. |
| 7,011,630 B2 | 3/2006 | Desai et al. |
| 7,018,366 B2 | 3/2006 | Easter |
| 7,018,568 B2 | 3/2006 | Tierney |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,743 B2 | 4/2006 | Mann et al. |
| 7,029,444 B2 | 4/2006 | Shin et al. |
| 7,039,810 B1 | 5/2006 | Nichols |
| 7,041,068 B2 | 5/2006 | Freeman et al. |
| 7,041,468 B2 | 5/2006 | Drucker et al. |
| 7,049,277 B2 | 5/2006 | Bragulla et al. |
| 7,052,251 B2 | 5/2006 | Nason et al. |
| 7,052,472 B1 | 5/2006 | Miller et al. |
| 7,052,483 B2 | 5/2006 | Wojcik |
| 7,056,302 B2 | 6/2006 | Douglas |
| 7,060,030 B2 | 6/2006 | Von Arx et al. |
| 7,074,307 B2 | 7/2006 | Simpson et al. |
| 7,081,195 B2 | 7/2006 | Simpson et al. |
| 7,089,780 B2 | 8/2006 | Sunshine et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,114,502 B2 | 10/2006 | Schulman et al. |
| 7,124,027 B1 | 10/2006 | Ernst et al. |
| 7,125,382 B2 | 10/2006 | Zhou et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,150,975 B2 | 12/2006 | Tamada et al. |
| 7,154,398 B2 | 12/2006 | Chen et al. |
| 7,155,112 B2 | 12/2006 | Uno et al. |
| 7,155,290 B2 | 12/2006 | Von Arx et al. |
| 7,163,511 B2 | 1/2007 | Conn et al. |
| 7,171,274 B2 | 1/2007 | Starkweather et al. |
| 7,183,068 B2 | 2/2007 | Burson et al. |
| 7,183,102 B2 | 2/2007 | Monfre et al. |
| 7,189,341 B2 | 3/2007 | Li et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,221,977 B1 | 5/2007 | Weaver et al. |
| 7,226,442 B2 | 6/2007 | Sheppard et al. |
| 7,226,978 B2 | 6/2007 | Tapsak et al. |
| 7,228,162 B2 | 6/2007 | Ward et al. |
| 7,228,163 B2 | 6/2007 | Ackerman |
| 7,233,817 B2 | 6/2007 | Yen |
| 7,241,266 B2 | 7/2007 | Zhou et al. |
| 7,261,691 B1 | 8/2007 | Asomani |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,291,107 B2 | 11/2007 | Hellwig et al. |
| 7,295,867 B2 | 11/2007 | Berner et al. |
| 7,297,112 B2 | 11/2007 | Zhou et al. |
| 7,299,082 B2 | 11/2007 | Feldman et al. |
| 7,310,544 B2 | 12/2007 | Brister et al. |
| 7,324,012 B2 | 1/2008 | Mann et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,398,183 B2 | 7/2008 | Holland et al. |
| 7,402,153 B2 | 7/2008 | Steil et al. |
| 7,408,132 B2 | 8/2008 | Wambsganss et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,768,387 B2 | 8/2010 | Fennell |
| 7,813,809 B2 | 10/2010 | Strother et al. |
| 7,948,369 B2 | 5/2011 | Fennell |
| 2001/0011224 A1 | 8/2001 | Brown |
| 2001/0016310 A1 | 8/2001 | Brown et al. |
| 2001/0016682 A1 | 8/2001 | Berner et al. |
| 2001/0016683 A1 | 8/2001 | Darrow et al. |
| 2001/0020124 A1 | 9/2001 | Tamada |
| 2001/0029340 A1 | 10/2001 | Mault et al. |
| 2001/0032278 A1 | 10/2001 | Brown et al. |

| | | |
|---|---|---|
| 2001/0037060 A1 | 11/2001 | Thompson et al. |
| 2001/0037069 A1 | 11/2001 | Carlson et al. |
| 2001/0037366 A1 | 11/2001 | Webb et al. |
| 2001/0039504 A1 | 11/2001 | Linberg et al. |
| 2001/0041830 A1 | 11/2001 | Varalli et al. |
| 2001/0041831 A1 | 11/2001 | Starkweather et al. |
| 2001/0044581 A1 | 11/2001 | Mault |
| 2001/0044588 A1 | 11/2001 | Mault |
| 2001/0047125 A1 | 11/2001 | Quy |
| 2001/0047127 A1 | 11/2001 | New et al. |
| 2001/0049096 A1 | 12/2001 | Brown |
| 2001/0049470 A1 | 12/2001 | Mault et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0013522 A1 | 1/2002 | Lav et al. |
| 2002/0013538 A1 | 1/2002 | Teller |
| 2002/0016530 A1 | 2/2002 | Brown |
| 2002/0016719 A1 | 2/2002 | Nemeth et al. |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019748 A1 | 2/2002 | Brown |
| 2002/0026937 A1 | 3/2002 | Mault |
| 2002/0027164 A1 | 3/2002 | Mault et al. |
| 2002/0028995 A1 | 3/2002 | Mault |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0049482 A1 | 4/2002 | Fabian et al. |
| 2002/0053637 A1 | 5/2002 | Conn et al. |
| 2002/0062069 A1 | 5/2002 | Mault |
| 2002/0063060 A1 | 5/2002 | Gascoyne et al. |
| 2002/0068858 A1 | 6/2002 | Braig et al. |
| 2002/0072784 A1 | 6/2002 | Sheppard et al. |
| 2002/0072858 A1 | 6/2002 | Cheng |
| 2002/0074162 A1 | 6/2002 | Su et al. |
| 2002/0077765 A1 | 6/2002 | Mault |
| 2002/0077766 A1 | 6/2002 | Mault |
| 2002/0081559 A1 | 6/2002 | Brown et al. |
| 2002/0083461 A1 | 6/2002 | Hutcheson et al. |
| 2002/0084196 A1 | 7/2002 | Liamos et al. |
| 2002/0087056 A1 | 7/2002 | Aceti et al. |
| 2002/0091312 A1 | 7/2002 | Berner et al. |
| 2002/0091796 A1 | 7/2002 | Higginson et al. |
| 2002/0103425 A1 | 8/2002 | Mault |
| 2002/0103499 A1 | 8/2002 | Perez et al. |
| 2002/0106709 A1 | 8/2002 | Potts et al. |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118528 A1 | 8/2002 | Su et al. |
| 2002/0119711 A1 | 8/2002 | Van Antwerp et al. |
| 2002/0124017 A1 | 9/2002 | Mault |
| 2002/0126036 A1 | 9/2002 | Flaherty et al. |
| 2002/0128594 A1 | 9/2002 | Das et al. |
| 2002/0130042 A1 | 9/2002 | Moerman et al. |
| 2002/0133378 A1 | 9/2002 | Mault et al. |
| 2002/0147135 A1 | 10/2002 | Schnell |
| 2002/0161286 A1 | 10/2002 | Gerber et al. |
| 2002/0161288 A1 | 10/2002 | Shin et al. |
| 2002/0169394 A1 | 11/2002 | Eppstein et al. |
| 2002/0169635 A1 | 11/2002 | Shillingburg |
| 2002/0177764 A1 | 11/2002 | Sohrab |
| 2002/0193679 A1 | 12/2002 | Malave et al. |
| 2003/0004403 A1 | 1/2003 | Drinan et al. |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032077 A1 | 2/2003 | Itoh et al. |
| 2003/0032867 A1 | 2/2003 | Crothall et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0042137 A1 | 3/2003 | Mao et al. |
| 2003/0050537 A1 | 3/2003 | Wessel |
| 2003/0050546 A1 | 3/2003 | Desai et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0076792 A1 | 4/2003 | Theimer |
| 2003/0081370 A1 | 5/2003 | Haskell et al. |
| 2003/0100040 A1 | 5/2003 | Bonnecaze et al. |
| 2003/0100821 A1 | 5/2003 | Heller et al. |
| 2003/0105407 A1 | 6/2003 | Pearce et al. |
| 2003/0108976 A1 | 6/2003 | Braig et al. |
| 2003/0114897 A1 | 6/2003 | Von Arx et al. |
| 2003/0122021 A1 | 7/2003 | McConnell et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0144579 A1 | 7/2003 | Buss |
| 2003/0146841 A1 | 8/2003 | Koenig |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0168338 A1 | 9/2003 | Gao et al. |
| 2003/0175806 A1 | 9/2003 | Rule et al. |
| 2003/0176183 A1 | 9/2003 | Drucker et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0199790 A1 | 10/2003 | Boecker et al. |
| 2003/0199791 A1 | 10/2003 | Boecker et al. |
| 2003/0199903 A1 | 10/2003 | Boecker et al. |
| 2003/0203498 A1 | 10/2003 | Neel et al. |
| 2003/0204290 A1 | 10/2003 | Sadler et al. |
| 2003/0208110 A1 | 11/2003 | Mault et al. |
| 2003/0208113 A1 | 11/2003 | Mault et al. |
| 2003/0208114 A1 | 11/2003 | Ackerman |
| 2003/0208133 A1 | 11/2003 | Mault |
| 2003/0208409 A1 | 11/2003 | Mault |
| 2003/0212317 A1 | 11/2003 | Kovatchev et al. |
| 2003/0212364 A1 | 11/2003 | Mann et al. |
| 2003/0212379 A1 | 11/2003 | Bylund et al. |
| 2003/0212579 A1 | 11/2003 | Brown et al. |
| 2003/0216630 A1 | 11/2003 | Jersey-Willuhn et al. |
| 2003/0217966 A1 | 11/2003 | Tapsak et al. |
| 2003/0226695 A1 | 12/2003 | Mault |
| 2003/0229514 A2 | 12/2003 | Brown |
| 2003/0232370 A1 | 12/2003 | Trifiro |
| 2003/0235817 A1 | 12/2003 | Bartkowiak et al. |
| 2004/0010207 A1 | 1/2004 | Flaherty et al. |
| 2004/0011671 A1 | 1/2004 | Shults et al. |
| 2004/0017300 A1 | 1/2004 | Kotzin et al. |
| 2004/0018486 A1 | 1/2004 | Dunn et al. |
| 2004/0030226 A1 | 2/2004 | Quy |
| 2004/0030531 A1 | 2/2004 | Miller et al. |
| 2004/0039256 A1 | 2/2004 | Kawatahara et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064068 A1 | 4/2004 | DeNuzzio et al. |
| 2004/0069164 A1 | 4/2004 | Nakamura et al. |
| 2004/0072357 A1 | 4/2004 | Stiene et al. |
| 2004/0073095 A1 | 4/2004 | Causey, III et al. |
| 2004/0096959 A1 | 5/2004 | Stiene et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0108226 A1 | 6/2004 | Polychronakos et al. |
| 2004/0122353 A1 | 6/2004 | Shahmirian et al. |
| 2004/0122489 A1 | 6/2004 | Mazar et al. |

| | | | | | | |
|---|---|---|---|---|---|---|
| 2004/0122530 A1 | 6/2004 | Hansen et al. | | 2005/0148003 A1 | 7/2005 | Keith et al. |
| 2004/0133164 A1 | 7/2004 | Funderburk et al. | | 2005/0154271 A1 | 7/2005 | Rasdal et al. |
| 2004/0138588 A1 | 7/2004 | Saikley et al. | | 2005/0161346 A1 | 7/2005 | Simpson et al. |
| 2004/0146909 A1 | 7/2004 | Duong et al. | | 2005/0171503 A1 | 8/2005 | Van Den Berghe et al. |
| 2004/0152622 A1 | 8/2004 | Keith et al. | | 2005/0171513 A1 | 8/2005 | Mann et al. |
| 2004/0152961 A1 | 8/2004 | Carlson et al. | | 2005/0173245 A1 | 8/2005 | Feldman et al. |
| 2004/0153585 A1 | 8/2004 | Kawatahara et al. | | 2005/0176136 A1 | 8/2005 | Burd et al. |
| 2004/0162473 A1 | 8/2004 | Sohrab | | 2005/0177036 A1 | 8/2005 | Shults et al. |
| 2004/0164961 A1 | 8/2004 | Bal et al. | | 2005/0177398 A1 | 8/2005 | Watanabe et al. |
| 2004/0167383 A1 | 8/2004 | Kim et al. | | 2005/0181012 A1 | 8/2005 | Saint et al. |
| 2004/0167464 A1 | 8/2004 | Ireland et al. | | 2005/0182306 A1 | 8/2005 | Sloan |
| 2004/0167801 A1 | 8/2004 | Say et al. | | 2005/0182451 A1 | 8/2005 | Griffin et al. |
| 2004/0171921 A1 | 9/2004 | Say et al. | | 2005/0187720 A1 | 8/2005 | Goode, Jr. et al. |
| 2004/0172284 A1 | 9/2004 | Sullivan et al. | | 2005/0192494 A1 | 9/2005 | Ginsberg |
| 2004/0176672 A1 | 9/2004 | Silver et al. | | 2005/0192557 A1 | 9/2005 | Brauker et al. |
| 2004/0176913 A1 | 9/2004 | Kawatahara et al. | | 2005/0195930 A1 | 9/2005 | Spital et al. |
| 2004/0186362 A1 | 9/2004 | Brauker et al. | | 2005/0199494 A1 | 9/2005 | Say et al. |
| 2004/0186365 A1 | 9/2004 | Jin et al. | | 2005/0203360 A1 | 9/2005 | Brauker et al. |
| 2004/0193025 A1 | 9/2004 | Steil et al. | | 2005/0203707 A1 | 9/2005 | Tsutsui et al. |
| 2004/0193090 A1 | 9/2004 | Lebel et al. | | 2005/0204134 A1 | 9/2005 | Von Arx et al. |
| 2004/0197846 A1 | 10/2004 | Hockersmith et al. | | 2005/0214892 A1 | 9/2005 | Kovatchev et al. |
| 2004/0199059 A1 | 10/2004 | Brauker et al. | | 2005/0215871 A1 | 9/2005 | Feldman et al. |
| 2004/0202576 A1 | 10/2004 | Aceti et al. | | 2005/0215872 A1 | 9/2005 | Berner et al. |
| 2004/0204687 A1 | 10/2004 | Mogensen et al. | | 2005/0239154 A1 | 10/2005 | Feldman et al. |
| 2004/0208780 A1 | 10/2004 | Faries, Jr. et al. | | 2005/0239156 A1 | 10/2005 | Drucker et al. |
| 2004/0221057 A1 | 11/2004 | Darcey et al. | | 2005/0241957 A1 | 11/2005 | Mao et al. |
| 2004/0225338 A1 | 11/2004 | Lebel et al. | | 2005/0245795 A1 | 11/2005 | Goode, Jr. et al. |
| 2004/0235446 A1 | 11/2004 | Flaherty et al. | | 2005/0245799 A1 | 11/2005 | Brauker et al. |
| 2004/0236200 A1 | 11/2004 | Say et al. | | 2005/0245839 A1 | 11/2005 | Stivoric et al. |
| 2004/0248204 A1 | 12/2004 | Moerman | | 2005/0245904 A1 | 11/2005 | Estes et al. |
| 2004/0249250 A1 | 12/2004 | McGee et al. | | 2005/0251033 A1 | 11/2005 | Scarantino et al. |
| 2004/0249253 A1 | 12/2004 | Racchini et al. | | 2005/0251083 A1 | 11/2005 | Carr-Brendel et al. |
| 2004/0249254 A1 | 12/2004 | Racchini et al. | | 2005/0261660 A1 | 11/2005 | Choi |
| 2004/0249999 A1 | 12/2004 | Connolly et al. | | 2005/0267780 A1 | 12/2005 | Ray et al. |
| 2004/0253736 A1 | 12/2004 | Stout et al. | | 2005/0271546 A1 | 12/2005 | Gerber et al. |
| 2004/0254429 A1 | 12/2004 | Yang | | 2005/0271547 A1 | 12/2005 | Gerber et al. |
| 2004/0254433 A1 | 12/2004 | Bandis et al. | | 2005/0272640 A1 | 12/2005 | Doyle et al. |
| 2004/0254434 A1 | 12/2004 | Goodnow et al. | | 2005/0272985 A1 | 12/2005 | Kotulla et al. |
| 2004/0260363 A1 | 12/2004 | Von Arx et al. | | 2005/0277164 A1 | 12/2005 | Drucker et al. |
| 2004/0263354 A1 | 12/2004 | Mann et al. | | 2005/0287620 A1 | 12/2005 | Heller et al. |
| 2004/0267300 A1 | 12/2004 | Mace | | 2006/0001538 A1 | 1/2006 | Kraft et al. |
| 2005/0003470 A1 | 1/2005 | Nelson et al. | | 2006/0001550 A1 | 1/2006 | Mann et al. |
| 2005/0004439 A1 | 1/2005 | Shin et al. | | 2006/0001551 A1 | 1/2006 | Kraft et al. |
| 2005/0004494 A1 | 1/2005 | Perez et al. | | 2006/0003398 A1 | 1/2006 | Heller et al. |
| 2005/0010087 A1 | 1/2005 | Banet et al. | | 2006/0004270 A1 | 1/2006 | Bedard et al. |
| 2005/0010269 A1 | 1/2005 | Lebel et al. | | 2006/0004271 A1 | 1/2006 | Peyser et al. |
| 2005/0016276 A1 | 1/2005 | Guan et al. | | 2006/0007017 A1 | 1/2006 | Mann et al. |
| 2005/0027177 A1 | 2/2005 | Shin et al. | | 2006/0015020 A1 | 1/2006 | Neale et al. |
| 2005/0027179 A1 | 2/2005 | Berner et al. | | 2006/0015024 A1 | 1/2006 | Brister et al. |
| 2005/0027180 A1 | 2/2005 | Goode, Jr. et al. | | 2006/0016700 A1 | 1/2006 | Brister et al. |
| 2005/0027181 A1 | 2/2005 | Goode, Jr. et al. | | 2006/0019327 A1 | 1/2006 | Brister et al. |
| 2005/0027462 A1 | 2/2005 | Goode, Jr. et al. | | 2006/0020186 A1 | 1/2006 | Brister et al. |
| 2005/0027463 A1 | 2/2005 | Goode, Jr. et al. | | 2006/0020187 A1 | 1/2006 | Brister et al. |
| 2005/0031689 A1 | 2/2005 | Shults et al. | | 2006/0020188 A1 | 1/2006 | Kamath et al. |
| 2005/0033132 A1 | 2/2005 | Shults et al. | | 2006/0020189 A1 | 1/2006 | Brister et al. |
| 2005/0038332 A1 | 2/2005 | Saidara et al. | | 2006/0020190 A1 | 1/2006 | Kamath et al. |
| 2005/0038680 A1 | 2/2005 | McMahon | | 2006/0020191 A1 | 1/2006 | Brister et al. |
| 2005/0043598 A1 | 2/2005 | Goode, Jr. et al. | | 2006/0020192 A1 | 1/2006 | Brister et al. |
| 2005/0043894 A1 | 2/2005 | Fernandez | | 2006/0025663 A1 | 2/2006 | Talbot et al. |
| 2005/0049473 A1 | 3/2005 | Desai et al. | | 2006/0029177 A1 | 2/2006 | Cranford, Jr. et al. |
| 2005/0054909 A1 | 3/2005 | Petisce et al. | | 2006/0031094 A1 | 2/2006 | Cohen et al. |
| 2005/0065464 A1 | 3/2005 | Talbot et al. | | 2006/0036139 A1 | 2/2006 | Brister et al. |
| 2005/0090607 A1 | 4/2005 | Tapsak et al. | | 2006/0036140 A1 | 2/2006 | Brister et al. |
| 2005/0096511 A1 | 5/2005 | Fox et al. | | 2006/0036141 A1 | 2/2006 | Kamath et al. |
| 2005/0096512 A1 | 5/2005 | Fox et al. | | 2006/0036142 A1 | 2/2006 | Brister et al. |
| 2005/0112169 A1 | 5/2005 | Brauker et al. | | 2006/0036143 A1 | 2/2006 | Brister et al. |
| 2005/0112544 A1 | 5/2005 | Xu et al. | | 2006/0036144 A1 | 2/2006 | Brister et al. |
| 2005/0113653 A1 | 5/2005 | Fox et al. | | 2006/0036145 A1 | 2/2006 | Brister et al. |
| 2005/0113657 A1 | 5/2005 | Alarcon et al. | | 2006/0036187 A1 | 2/2006 | Vos et al. |
| 2005/0113658 A1 | 5/2005 | Jacobson et al. | | 2006/0040402 A1 | 2/2006 | Brauker et al. |
| 2005/0113886 A1 | 5/2005 | Fischell et al. | | 2006/0052679 A1 | 3/2006 | Kotulla et al. |
| 2005/0114068 A1 | 5/2005 | Chey et al. | | 2006/0058602 A1 | 3/2006 | Kwiatkowski et al. |
| 2005/0118726 A1 | 6/2005 | Schultz et al. | | 2006/0063218 A1 | 3/2006 | Bartkowiak et al. |
| 2005/0121322 A1 | 6/2005 | Say et al. | | 2006/0074564 A1 | 4/2006 | Bartkowiak et al. |
| 2005/0124873 A1 | 6/2005 | Shults et al. | | 2006/0129733 A1 | 6/2006 | Solbelman |
| 2005/0131346 A1 | 6/2005 | Douglas | | 2006/0142651 A1 | 6/2006 | Brister et al. |
| 2005/0137471 A1 | 6/2005 | Haar et al. | | 2006/0155180 A1 | 7/2006 | Brister et al. |
| 2005/0143635 A1 | 6/2005 | Kamath et al. | | 2006/0166629 A1 | 7/2006 | Reggiardo |
| 2005/0143636 A1 | 6/2005 | Zhang et al. | | 2006/0173260 A1 | 8/2006 | Gaoni et al. |

| | | | | | |
|---|---|---|---|---|---|
| 2006/0173406 A1 | 8/2006 | Hayes et al. | 2008/0071156 A1 | 3/2008 | Brister et al. |
| 2006/0173444 A1 | 8/2006 | Choy et al. | 2008/0071157 A1 | 3/2008 | McGarraugh et al. |
| 2006/0183985 A1 | 8/2006 | Brister et al. | 2008/0071158 A1 | 3/2008 | McGarraugh et al. |
| 2006/0189863 A1 | 8/2006 | Peyser et al. | 2008/0081977 A1 | 4/2008 | Hayter et al. |
| 2006/0195029 A1 | 8/2006 | Shults et al. | 2008/0083617 A1 | 4/2008 | Simpson et al. |
| 2006/0200112 A1 | 9/2006 | Paul | 2008/0086042 A1 | 4/2008 | Brister et al. |
| 2006/0202859 A1 | 9/2006 | Mastrototaro et al. | 2008/0086044 A1 | 4/2008 | Brister et al. |
| 2006/0222566 A1 | 10/2006 | Brauker et al. | 2008/0086273 A1 | 4/2008 | Shults et al. |
| 2006/0224109 A1 | 10/2006 | Steil et al. | 2008/0097289 A1 | 4/2008 | Steil et al. |
| 2006/0224141 A1 | 10/2006 | Rush et al. | 2008/0108942 A1 | 5/2008 | Brister et al. |
| 2006/0226985 A1 | 10/2006 | Goodnow et al. | 2008/0154513 A1 | 6/2008 | Kovatchev et al. |
| 2006/0229512 A1 | 10/2006 | Petisce et al. | 2008/0167543 A1 | 7/2008 | Say et al. |
| 2006/0247508 A1 | 11/2006 | Fennell | 2008/0172205 A1 | 7/2008 | Breton et al. |
| 2006/0247985 A1 | 11/2006 | Liamos et al. | 2008/0183060 A1 | 7/2008 | Steil et al. |
| 2006/0258918 A1 | 11/2006 | Burd et al. | 2008/0183061 A1 | 7/2008 | Goode et al. |
| 2006/0258929 A1 | 11/2006 | Goode, Jr. et al. | 2008/0183399 A1 | 7/2008 | Goode et al. |
| 2006/0263763 A1 | 11/2006 | Simpson et al. | 2008/0188731 A1 | 8/2008 | Brister et al. |
| 2006/0272652 A1 | 12/2006 | Stocker et al. | 2008/0188796 A1 | 8/2008 | Steil et al. |
| 2006/0290496 A1 | 12/2006 | Peeters | 2008/0189051 A1 | 8/2008 | Goode et al. |
| 2007/0016381 A1 | 1/2007 | Kamath et al. | 2008/0194935 A1 | 8/2008 | Brister et al. |
| 2007/0027381 A1 | 2/2007 | Stafford | 2008/0194936 A1 | 8/2008 | Goode et al. |
| 2007/0033074 A1 | 2/2007 | Nitzan et al. | 2008/0194937 A1 | 8/2008 | Goode et al. |
| 2007/0060814 A1 | 3/2007 | Stafford | 2008/0194938 A1 | 8/2008 | Brister et al. |
| 2007/0066873 A1 | 3/2007 | Kamath et al. | 2008/0195232 A1 | 8/2008 | Carr-Brendel et al. |
| 2007/0071681 A1 | 3/2007 | Gadkar et al. | 2008/0195967 A1 | 8/2008 | Goode et al. |
| 2007/0073129 A1 | 3/2007 | Shah et al. | 2008/0197024 A1 | 8/2008 | Simpson et al. |
| 2007/0078320 A1 | 4/2007 | Stafford | 2008/0200788 A1 | 8/2008 | Brister et al. |
| 2007/0078321 A1 | 4/2007 | Mazza et al. | 2008/0200789 A1 | 8/2008 | Brister et al. |
| 2007/0078322 A1 | 4/2007 | Stafford | 2008/0200791 A1 | 8/2008 | Simpson et al. |
| 2007/0078323 A1 | 4/2007 | Reggiardo et al. | 2008/0208025 A1 | 8/2008 | Shults et al. |
| 2007/0090511 A1 | 4/2007 | Borland et al. | 2008/0208113 A1 | 8/2008 | Damiano et al. |
| 2007/0106135 A1 | 5/2007 | Sloan et al. | 2008/0214915 A1 | 9/2008 | Brister et al. |
| 2007/0124002 A1 | 5/2007 | Estes et al. | 2008/0214918 A1 | 9/2008 | Brister et al. |
| 2007/0149873 A1 | 6/2007 | Say et al. | 2008/0228051 A1 | 9/2008 | Shults et al. |
| 2007/0149874 A1 | 6/2007 | Say et al. | 2008/0228054 A1 | 9/2008 | Shults et al. |
| 2007/0149875 A1 | 6/2007 | Ouyang et al. | 2008/0242961 A1 | 10/2008 | Brister et al. |
| 2007/0151869 A1 | 7/2007 | Heller et al. | 2008/0255434 A1 | 10/2008 | Hayter et al. |
| 2007/0161879 A1 | 7/2007 | Say et al. | 2008/0255437 A1 | 10/2008 | Hayter |
| 2007/0161880 A1 | 7/2007 | Say et al. | 2008/0255808 A1 | 10/2008 | Hayter |
| 2007/0163880 A1 | 7/2007 | Woo et al. | 2008/0256048 A1 | 10/2008 | Hayter |
| 2007/0168224 A1 | 7/2007 | Letzt et al. | 2008/0262469 A1 | 10/2008 | Brister et al. |
| 2007/0173706 A1 | 7/2007 | Neinast et al. | 2008/0275313 A1 | 11/2008 | Brister et al. |
| 2007/0173761 A1 | 7/2007 | Kanderian et al. | 2008/0278331 A1 | 11/2008 | Hayter et al. |
| 2007/0179349 A1 | 8/2007 | Hoyme et al. | 2008/0278332 A1 | 11/2008 | Fennell et al. |
| 2007/0179352 A1 | 8/2007 | Randlov et al. | 2008/0278333 A1 | 11/2008 | Fennell et al. |
| 2007/0179370 A1 | 8/2007 | Say et al. | 2008/0281171 A1 | 11/2008 | Fennell et al. |
| 2007/0179372 A1 | 8/2007 | Say et al. | 2008/0281179 A1 | 11/2008 | Fennell et al. |
| 2007/0191699 A1 | 8/2007 | Say et al. | 2008/0281840 A1 | 11/2008 | Fennell et al. |
| 2007/0191700 A1 | 8/2007 | Say et al. | 2008/0287761 A1 | 11/2008 | Hayter |
| 2007/0191701 A1 | 8/2007 | Feldman et al. | 2008/0287762 A1 | 11/2008 | Hayter |
| 2007/0203407 A1 | 8/2007 | Hoss et al. | 2008/0287763 A1 | 11/2008 | Hayter |
| 2007/0203408 A1 | 8/2007 | Say et al. | 2008/0287764 A1 | 11/2008 | Rasdal et al. |
| 2007/0203410 A1 | 8/2007 | Say et al. | 2008/0287765 A1 | 11/2008 | Rasdal et al. |
| 2007/0203411 A1 | 8/2007 | Say et al. | 2008/0287766 A1 | 11/2008 | Rasdal et al. |
| 2007/0203966 A1 | 8/2007 | Brauker et al. | 2008/0288180 A1 | 11/2008 | Hayter |
| 2007/0208247 A1 | 9/2007 | Say et al. | 2008/0288204 A1 | 11/2008 | Hayter et al. |
| 2007/0213610 A1 | 9/2007 | Say et al. | 2008/0296155 A1 | 12/2008 | Shults et al. |
| 2007/0213657 A1 | 9/2007 | Jennewine et al. | 2008/0300919 A1 | 12/2008 | Charlton et al. |
| 2007/0215491 A1 | 9/2007 | Heller et al. | 2008/0300920 A1 | 12/2008 | Brown et al. |
| 2007/0218097 A1 | 9/2007 | Heller et al. | 2008/0301158 A1 | 12/2008 | Brown et al. |
| 2007/0232877 A1 | 10/2007 | He | 2008/0301665 A1 | 12/2008 | Charlton et al. |
| 2007/0235331 A1 | 10/2007 | Simpson et al. | 2008/0306368 A1 | 12/2008 | Goode et al. |
| 2007/0244380 A1 | 10/2007 | Say et al. | 2008/0306434 A1 | 12/2008 | Dobbles et al. |
| 2007/0249919 A1 | 10/2007 | Say et al. | 2008/0306435 A1 | 12/2008 | Kamath et al. |
| 2007/0249920 A1 | 10/2007 | Say et al. | 2008/0306444 A1 | 12/2008 | Brister et al. |
| 2007/0249922 A1 | 10/2007 | Peyser et al. | 2008/0312841 A1 | 12/2008 | Hayter |
| 2007/0299617 A1 | 12/2007 | Willis | 2008/0312842 A1 | 12/2008 | Hayter |
| 2008/0004515 A1 | 1/2008 | Jennewine et al. | 2008/0312844 A1 | 12/2008 | Hayter et al. |
| 2008/0004601 A1 | 1/2008 | Jennewine et al. | 2008/0312845 A1 | 12/2008 | Hayter et al. |
| 2008/0009304 A1 | 1/2008 | Fry | 2009/0005665 A1 | 1/2009 | Hayter et al. |
| 2008/0009692 A1 | 1/2008 | Stafford | 2009/0006034 A1 | 1/2009 | Hayter et al. |
| 2008/0017522 A1 | 1/2008 | Heller et al. | 2009/0012379 A1 | 1/2009 | Goode et al. |
| 2008/0021666 A1 | 1/2008 | Goode, Jr. et al. | 2009/0018424 A1 | 1/2009 | Kamath et al. |
| 2008/0029391 A1 | 2/2008 | Mao et al. | 2009/0030294 A1 | 1/2009 | Petisce et al. |
| 2008/0033254 A1 | 2/2008 | Kamath et al. | 2009/0033482 A1 | 2/2009 | Hayter et al. |
| 2008/0039702 A1 | 2/2008 | Hayter et al. | 2009/0036747 A1 | 2/2009 | Hayter et al. |
| 2008/0045824 A1 | 2/2008 | Tapsak et al. | 2009/0036758 A1 | 2/2009 | Brauker et al. |
| 2008/0058625 A1 | 3/2008 | McGarraugh et al. | 2009/0036760 A1 | 2/2009 | Hayter |
| 2008/0064937 A1 | 3/2008 | McGarraugh et al. | 2009/0036763 A1 | 2/2009 | Brauker et al. |

| | | | |
|---|---|---|---|
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0105636 A1 | 4/2009 | Hayter et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149717 A1 | 6/2009 | Brauer et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0318789 A1 | 12/2009 | Fennell et al. |
| 2009/0318792 A1 | 12/2009 | Fennell et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |

| | | | |
|---|---|---|---|
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |

FOREIGN PATENT DOCUMENTS

| | | |
|---|---|---|
| EP | 1579690 | 11/1980 |
| EP | 0026995 | 4/1981 |
| EP | 0048090 | 3/1982 |
| EP | 0078636 | 5/1983 |
| EP | 0080304 | 6/1983 |
| EP | 0098592 | 1/1984 |
| EP | 0125139 | 11/1984 |
| EP | 0127958 | 12/1984 |
| EP | 0136362 | 4/1985 |
| EP | 0170375 | 2/1986 |
| EP | 0177743 | 4/1986 |
| EP | 0184909 | 6/1986 |
| EP | 0206218 | 12/1986 |
| EP | 0230472 | 8/1987 |
| EP | 0241309 | 10/1987 |
| EP | 0245073 | 11/1987 |
| EP | 0255291 | 2/1988 |
| EP | 0278647 | 8/1988 |
| EP | 0320109 | 6/1989 |
| EP | 0353328 | 2/1990 |
| EP | 0359831 | 3/1990 |
| EP | 0368209 | 5/1990 |
| EP | 0390390 | 10/1990 |
| EP | 0396788 | 11/1990 |
| EP | 0400918 | 12/1990 |
| EP | 0453283 | 10/1991 |
| EP | 0470290 | 2/1992 |
| EP | 0504835 | 9/1992 |
| EP | 0286118 | 1/1995 |
| EP | 0653718 | 5/1995 |
| EP | 0680727 | 11/1995 |
| EP | 0800082 | 10/1997 |
| EP | 0880936 | 12/1998 |
| EP | 0970655 | 1/2000 |
| EP | 1034734 | 9/2000 |
| EP | 1048264 | 11/2000 |
| EP | 1445746 | 8/2004 |
| EP | 1413245 | 6/2011 |
| GB | 1394171 | 5/1975 |
| GB | 1579690 | 11/1980 |
| GB | 1599241 | 9/1981 |
| GB | 2073891 | 10/1981 |
| GB | 2154003 | 8/1985 |
| GB | 2194892 | 3/1988 |
| GB | 2204408 | 11/1988 |
| GB | 2225637 | 6/1990 |
| GB | 2254436 | 10/1992 |
| SU | 1281988 | 1/1987 |
| WO | WO-85/05119 | 11/1985 |
| WO | WO-86/00513 | 1/1986 |
| WO | WO-87/00513 | 1/1987 |
| WO | WO-87/06040 | 10/1987 |
| WO | WO-89/02246 | 3/1989 |
| WO | WO-89/05119 | 6/1989 |
| WO | WO-89/08713 | 9/1989 |
| WO | WO-90/00367 | 1/1990 |
| WO | WO-90/05300 | 5/1990 |

| | | |
|---|---|---|
| WO | WO-90/05910 | 5/1990 |
| WO | WO-91/01680 | 2/1991 |
| WO | WO-91/04704 | 4/1991 |
| WO | WO-91/15993 | 10/1991 |
| WO | WO-92/01947 | 2/1992 |
| WO | WO-92/13271 | 8/1992 |
| WO | WO-94/20602 | 9/1994 |
| WO | WO-94/27140 | 11/1994 |
| WO | WO-95/28878 | 2/1995 |
| WO | WO-95/06240 | 3/1995 |
| WO | WO-96/07908 | 3/1996 |
| WO | WO-96/25089 | 8/1996 |
| WO | WO-96/30431 | 10/1996 |
| WO | WO-96/35370 | 11/1996 |
| WO | WO-97/02847 | 1/1997 |
| WO | WO-97/19344 | 5/1997 |
| WO | WO-97/20207 | 6/1997 |
| WO | WO-97/41421 | 11/1997 |
| WO | WO-97/42882 | 11/1997 |
| WO | WO-97/42883 | 11/1997 |
| WO | WO-97/42886 | 11/1997 |
| WO | WO-97/42888 | 11/1997 |
| WO | WO-97/43962 | 11/1997 |
| WO | WO-97/46868 | 12/1997 |
| WO | WO-98/09167 | 3/1998 |
| WO | WO-98/24366 | 6/1998 |
| WO | WO-98/35053 | 8/1998 |
| WO | WO-98/52045 | 11/1998 |
| WO | WO-98/52293 | 11/1998 |
| WO | WO-99/05966 | 2/1999 |
| WO | WO-99/32883 | 7/1999 |
| WO | WO-99/56613 | 11/1999 |
| WO | WO-00/13580 | 3/2000 |
| WO | WO-00/18294 | 4/2000 |
| WO | WO-00/19887 | 4/2000 |
| WO | WO-00/20626 | 4/2000 |
| WO | WO-00/33065 | 6/2000 |
| WO | WO-00/49940 | 8/2000 |
| WO | WO-00/59370 | 10/2000 |
| WO | WO-00/62664 | 10/2000 |
| WO | WO-00/62665 | 10/2000 |
| WO | WO-00/78210 | 12/2000 |
| WO | WO-00/78992 | 12/2000 |
| WO | WO-01/24038 | 4/2001 |
| WO | WO-01/33216 | 5/2001 |
| WO | WO-01/52727 | 7/2001 |
| WO | WO-01/52935 | 7/2001 |
| WO | WO-01/54753 | 8/2001 |
| WO | WO-01/57238 | 8/2001 |
| WO | WO-01/57239 | 8/2001 |
| WO | WO-01/67009 | 9/2001 |
| WO | WO-02/13686 | 2/2002 |
| WO | WO-02/16905 | 2/2002 |
| WO | WO-02/17210 | 2/2002 |
| WO | WO-02/058537 | 8/2002 |
| WO | WO-02/078512 | 10/2002 |
| WO | WO-03/036583 | 5/2003 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2004/098405 | 11/2004 |
| WO | WO-2005/041766 | 5/2005 |
| WO | WO-2005/089103 | 9/2005 |
| WO | WO-2006/024671 | 3/2006 |
| WO | WO-2006/037109 | 4/2006 |
| WO | WO-2006/079114 | 7/2006 |
| WO | WO-2006/118947 | 11/2006 |
| WO | WO-2006/119084 | 11/2006 |
| WO | WO-2007/002189 | 1/2007 |
| WO | WO-2007/016399 | 2/2007 |
| WO | WO-2007/027381 | 3/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/056638 | 5/2007 |
| WO | WO-2007/101223 | 9/2007 |
| WO | WO-2007/101260 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/003003 | 1/2008 |
| WO | WO-2008/005780 | 1/2008 |
| WO | WO-2008/021913 | 2/2008 |
| WO | WO-2008/042760 | 4/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2008/150428 | 12/2008 |
| WO | WO-2008/153825 | 12/2008 |
| WO | WO-2009/018058 | 2/2009 |
| WO | WO-2009/075697 | 6/2009 |
| WO | WO-2009/086216 | 7/2009 |
| WO | WO-2009/096992 | 8/2009 |
| WO | WO-2009/097594 | 8/2009 |

OTHER PUBLICATIONS

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.

Albery, W. J., et al., "Amperometric Enzyme Electrodes", *Philosophical Transactions of the Royal Society of London*, vol. 316, 1987, pp. 107-119.

Alcock, S. J., et al., "Continuous Analyte Monitoring to Aid Clinical Practice", *IEEE Engineering in Medicine and Biology Magazine*, 1994, pp. 319-325.

Anderson, L. B., et al., "Thin-Layer Electrochemistry: Steady-State Methods of Studying Rate Processes", *Journal of ElectroAnalytical Chemistry*, vol. 10, 1965, pp. 295-305.

Armour, J. C., et al., "Application of Chronic Intravascular Blood Glucose Sensor in Dogs", *Diabetes*, vol. 39, 1990, pp. 1519-1526.

Bartlett, P. N., et al., "Covalent Binding of Electron Relays to Glucose Oxidase", *Journal of the Chemical Society, Chemical Communications*, 1987, pp. 1603-1604.

Bartlett, P. N., et al., "Modification of Glucose Oxidase by Tetrathiafulvalene", *Journal of the Chemical Society, Chemical Communications*, 1990, pp. 1135-1136.

Bartlett, P. N., et al., "Strategies for the Development of Amperometric Enzyme Electrodes", *Biosensors*, vol. 3, 1987/1988, pp. 359-379.

Bennion, N., et al., "Alternate Site Glucose Testing: A Crossover Design", *Diabetes Technology & Therapeutics*, vol. 4, No. 1, 2002, pp. 25-33.

Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.

Blank, T. B., et al., "Clinical Results From a Non-Invasive Blood Glucose Monitor", *Optical Diagnostics and Sensing of Biological Fluids and Glucose and Cholesterol Monitoring II, Optical Proceedings of SPIE*, vol. 4624, 2002, pp. 1-10.

Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.

Boedeker Plastics, Inc., "Polyethylene Specifications", Web Page of Boedeker.com, 2007, pp. 1-3.

Brandt, J., et al., "Covalent Attachment of Proteins to Polysaccharide Carriers by Means of Benzoquinone", *Biochimica et Biophysica Acta*, vol. 386, 1975, pp. 196-202.

Brooks, S. L., et al., "Development of an On-Line Glucose Sensor for Fermentation Monitoring", *Biosensors*, vol. 3, 1987/1988, pp. 45-56.

Brownlee, M., et al., "A Glucose-Controlled Insulin-Delivery System: Semisynthetic Insulin Bound to Lectin", *Science*, vol. 206, 1979, 1190-1191.

Cass, A. E., et al., "Ferricinum Ion As an Electron Acceptor for Oxido-Reductases", *Journal of ElectroAnalytical Chemistry*, vol. 190, 1985, pp. 117-127.

Cass, A. E., et al., "Ferrocene-Medicated Enzyme Electrode for Amperometric Determination of Glucose", *Analytical Chemistry*, vol. 56, No. 4, 1984, 667-671.

Castner, J. F., et al., "Mass Transport and Reaction Kinetic Parameters Determined Electrochemically for Immobilized Glucose Oxidase", *Biochemistry*, vol. 23 No. 10, 1984, 2203-2210.

Claremont, D. J., et al., "Biosensors for Continuous in Vivo Glucose Monitoring", *Proceedings of the Annual International Conference of the IEEE Engineering in Medicine and Biology Society*, vol. 10, 1988.

Clark Jr., L. C., et al., "Differential Anodic Enzyme Polarography for the Measurement of Glucose", *Oxygen Transport to Tissue: Instrumentation, Methods, and Physiology*, 1973, pp. 127-133.

Clark Jr., L. C., et al., "Electrode Systems for Continuous Monitoring in Cardiovascular Surgery", *Annals New York Academy of Sciences*, 1962, pp. 29-45.

Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.

Csoregi, E., et al., "Design and Optimization of a Selective Subcutaneously Implantable Glucose Electrode on 'Wired' Glucose Oxidase", *Analytical Chemistry*, vol. 67, No. 7, 1995, pp. 1240-1244.

Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.

Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.

Dai, W. S., et al., "Hydrogel Membranes with Mesh Size Asymmetry Based on the Gradient Crosslinking of Poly(vinyl alcohol)," *Journal of Membrane Science*, vol. 156, 1999, pp. 67-79.

Davis, G., "Electrochemical Techniques for the Development of Amperometric Biosensors", *Biosensors*, vol. 1, 1985, pp. 161-178.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.

Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.

Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.

Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.

Ellis, C. D., et al., "Selectivity and Directed Charge Transfer through an Electroactive Metallopolymer Film", *Journal of the American Chemical Society*, vol. 103, No. 25, 1981, pp. 7480-7483.

Engstrom, R. C., "Electrochemical Pretreatment of Glassy Carbon Electrodes", *Analytical Chemistry*, vol. 54, No. 13, 1982, pp. 2310-2314.

Engstrom, R. C., et al., "Characterization of Electrochemically Pretreated Glassy Carbon Electrodes", *Analytical Chemistry*, vol. 56, No. 2, 1984, pp. 136-141.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.

Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.

Flentge, F., et al., "An Enzyme-Reactor for Electrochemical Monitoring of Choline and Acetylcholine: Applications in High-Performance Liquid Chromatography, Bran Tissue, Microdialysis and Cerebrospinal Fluid," *Analytical Biochemistry*, vol. 204, 1992, pp. 305-310.

Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.

Foulds, N. C., et al., "Immobilization of Glucose Oxidase in Ferrocene-Modified Pyrrole Polymers", *Analytical Chemistry*, vol. 60, No. 22, 1988, pp. 2473-2478.

Frew, J. E., et al., "Electron-Transfer Biosensors", *Philosophical Transactions of the Royal Society of London*, vol. 316, 1987, pp. 95-106.

Godsland, I. F., et al., "Maximizing the Success Rate of Minimal Model Insulin Sensitivity Measurement in Humans: The Importance of Basal Glucose Levels," *Clinical Science*, vol. 101, 2001, pp. 1-9.

Gorton, L., et al., "Selective Detection in Flow Analysis Based on the Combination of Immobilized Enzymes and Chemically Modified Electrodes", *Analytica Chimica Acta*, vol. 250, 1991, pp. 203-248.

Graham, N. B., "Poly(ethylene oxide) and Related Hydrogels," *Hydrogels in Medicine and Pharmacy*, vol. II: Polymers, Chapter 4, 1987, pp. 95-113.

Gregg, B. A., et al., "Cross-Linked Redox Gels Containing Glucose Oxidase for Amperometric Bionsensor Applications", *Analytical Chemistry*, vol. 62, No. 3, 1990, pp. 258-263.

Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.

Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.

Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.

Hawkridge, F. M., et al., "Indirect Coulometric Titration of Biological Electron Transport Components", *Analytical Chemistry*, vol. 45, No. 7, 1973, pp. 1021-1027.

Heller, A., "Electrical Connection Enzyme Redox Centers to Electrodes", *Journal of Physical Chemistry*, vol. 96, No. 9, 1990, pp. 3579-3587.

Heller, A., "Electrical Wiring of Redox Enzymes", *Accounts of Chemical Research* vol. 23, No. 5, 1990, 128-134.

Heller, A., et al., "Amperometric Biosensors Based on Three-Dimensional Hydrogel-Forming Epoxy Networks", *Sensors and Actuators B*, vol. 13-14, 1993, pp. 180-183.

Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.

Ianniello, R. M., et al , "Immobilized Enzyme Chemically Modified Electrode as an Amperometric Sensor", *Analytical Chemistry*, vol. 53, No. 13, 1981, pp. 2090-2095.

Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.

Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, J. M., et al., "Potential-Dependent Enzymatic Activity in an Enzyme Thin-Layer Cell", *Analytical Chemistry*, vol. 54, No. 8, 1982, pp. 1377-1383.

Johnson, K. W., "Reproducible Electrodeposition of Biomolecules for the Fabrication of Miniature Electroenzymatic Biosensors", *Sensors and Actuators B*, vol. 5, 1991, pp. 85-89.

Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.

Johnson, P. C., "Peripheral Circulation", *John Wiley & Sons*, 1978, pp. 198.

Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.

Josowicz, M., et al., "Electrochemical Pretreatment of Thin Film Platinum Electrodes", *Journal of the Electrochemical Society*, vol. 135 No. 1, 1988, pp. 112-115.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.

Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.

Kemp, G. J., "Theoretical Aspects of One-Point Calibration: Causes and Effects of Some Potential Errors, and Their Dependence on Concentration," *Clinical Chemistry*, vol. 30, No. 7, 1984, pp. 1163-1167.

Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine)$_2$Cl]$^{+/2+}$", *Journal of the Chemical Society, Faraday Transactions*, vol. 92, No. 20, 1996, pp. 4131-4136.

Kerner, W., et al., "The Function of a Hydrogen Peroxide-Detecting Electroenzymatic Glucose Electrode is Markedly Impaired in Human Subcutaneous Tissue and Plasma," *Biosensors & Bioelectronics*, vol. 8, 1993, pp. 473-482.

Korf, J., et al., "Monitoring of Glucose and Lactate Using Microdialysis: Applications in Neonates and Rat Brain," *Developmental Neuroscience*, vol. 15, 1993, pp. 240-246.

Koudelka, M., et al., "In-Vivo Behaviour of Hypodermically Implanted Microfabricated Glucose Sensors", *Biosensors & Bioelectronics*, vol. 6, 1991, pp. 31-36.

Kulys, J., et al., "Mediatorless Peroxidase Electrode and Preparation of Bienzyme Sensors", *Bioelectrochemistry and Bioenergetics*, vol. 24, 1990, pp. 305-311.

Lager, W., et al., "Implantable Electrocatalytic Glucose Sensor", *Hormone Metabolic Research*, vol. 26, 1994, pp. 526-530.

Laurell, T., "A Continuous Glucose Monitoring System Based on Microdialysis", *Journal of Medical Engineering & Technology*, vol. 16, No. 5, 1992, pp. 187-193.

Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Maidan, R., et al., "Elimination of Electrooxidizable Interferant-Produced Currents in Amperometric Biosensors", *Analytical Chemistry*, vol. 64, No. 23, 1992, pp. 2889-2896.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Marko-Varga, G., et al., "Enzyme-Based Biosensor as a Selective Detection Unit in Column Liquid Chromatography", *Journal of Chromatography A*, vol. 660, 1994, pp. 153-167.

Mastrototaro, J. J., et al., "An Electroenzymatic Glucose Sensor Fabricated on a Flexible Substrate", *Sensors and Actuators B*, vol. 5, 1991, pp. 139-144.

Mauras, N., et al., "Lack of Accuracy of Continuous Glucose Sensors in Healthy, Nondiabetic Children: Results of the Diabetes Research in Children Network (DirecNet) Accuracy Study," *Journal of Pediatrics*, 2004, pp. 770-775.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.

Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.

Moatti-Sirat, D., et al., "Evaluating in Vitro and in Vivo the Interference of Ascorbate and Acetaminophen on Glucose Detection by a Needle-Type Glucose Sensor", *Biosensors & Bioelectronics*, vol. 7, 1992, pp. 345-352.

Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.

Nagy, G., et al., "A New Type of Enzyme Electrode: The Ascorbic Acid Eliminator Electrode", *Life Sciences*, vol. 31, No. 23, 1982, pp. 2611-2616.

Nakamura, S., et al., "Effect of Periodate Oxidation on the Structure and Properties of Glucose Oxidase", *Biochimica et Biophysica Acta.*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

Ohara, T. J., "Osmium Bipyridyl Redox Polymers Used in Enzyme Electrodes", *Platinum Metals Review*, vol. 39, No. 2, 1995, pp. 54-62.

Ohara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

Ohara, T. J., et al., "Glucose Electrodes Based on Cross-Linked [Os(bpy)$_2$Cl]$^{+2}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for in Vivo Use", *Tibtech*, vol. 11, 1993, pp. 285-291.

Pickup, J., et al., "Implantable Glucose Sensors: Choosing the Appropriate Sensing Strategy", *Biosensors*, vol. 3, 1987/1988, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and in Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Reusch, W., "Other Topics: Organometallic Chemistry: Organometallic Compounds: Main Group Organometallic Compounds," *Virtual Textbook of Organic Chemistry*, 1999, Rev. 2007, 25 pages.

Roe, J. N., et al., "Bloodless Glucose Measurements", *Critical Review in Therapeutic Drug Carrier Systems*, vol. 15, Issue 3, 1998, pp. 199-241.

Sacks (Ed), "Guidelines Recommendations for Laboratory Analysis in the Diagnosis and Management of Diabetes Mellitus," *The National Academy of Clinical Biochemistry Presents Laboratory Medicine Practice Guidelines*, vol. 13, 2002, pp. 8-11, 21-23, 52-56, 63.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F. W., et al., "Second Generation Biosensors," *Biosensors & Bioelectronics*, vol. 6, 1991, pp. 245-253.

Scheller, F., et al., "Enzyme Electrodes and Their Application", *Philosophical Transaction of the Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Skoog, D. A., et al., "Evaluation of Analytical Data," *Fundamentals of Analytical Chemistry*, 1966, pp. 55.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modification to Produce a Lactate Biosensor Employing Microliter Volumes", *Electroanalysis*, vol. 8, No. 6, 1996, pp. 539-543.

Sternberg, F., et al., "Calibration Problems of Subcutaneous Glucosensors when Applied 'In-Situ' in Man", *Hormone and Metabolic Research*, vol. 26, 1994, pp. 523-526.

Sternberg, R., et al., "Covalent Enzyme Coupling on Cellulose Acetate Membranes for Glucose Sensor Development", *Analytical Chemistry*, vol. 60, No. 24, 1988, pp. 2781-2786.

Sternberg, R., et al., "Study and Development of Multilayer Needle-Type Enzyme-Based Glucose Microsensors", *Biosensors*, vol. 4, 1988, pp. 27-40.

Suekane, M , "Immobilization of Glucose Isomerase", *Zettschrift fur Allgemeine Mikrobiologie*, vol. 22, No. 8, 1982, pp. 565-576.

Tajima, S., et al., "Simultaneous Determination of Glucose and 1,5-Anydroglucitol", *Chemical Abstracts*, vol. 111, No. 25, 1989, pp. 394.

Takamura, A., et al., Drug release from Poly(vinyl alcohol) Gel Prepared by Freeze-Thaw Procedure, *Journal of Controlled Release*, vol. 20, 1992, pp. 21-27.

Tarasevich, M. R., "Bioelectrocatalysis", *Comprehensive Treatise of Electrochemistry*, vol. 10, 1985, pp. 231-295.

Tatsuma, T., et al., "Enzyme Monolayer- and Bilayer-Modified Tin Oxide Electrodes for the Determination of Hydrogen Peroxide and Glucose", *Analytical Chemistry*, vol. 61, No. 21, 1989, pp. 2352-2355.

Taylor, C., et al., "'Wiring' of Glucose Oxidase Within a Hydrogel Made with Polyvinyl Imidazole Complexed with [(Os-4,4'-dimethoxy-2,2'-bipyridine)Cl]$^{+2+}$", *Journal of ElectroAnalytical Chemistry*, vol. 396, 1995, pp. 511-515.

Thompson, M., et al., "In Vivo Probes: Problems and Perspectives", *Clinical Biochemistry*, vol. 19, 1986, pp. 255-261.

Travenol Laboratories, Inc., *An Introduction to "Eugly"*, Book 1, 1985, pp. 1-22.

Trojanowicz, M., et al., "Enzyme Entrapped Polypyrrole Modified Electrode for Flow-Injection Determination of Glucose", *Biosensors & Bioelectronics*, vol. 5, 1990, pp. 149-156.

Tsalikian, E., et al., "Accuracy of the GlucoWatch G2® Biographer and the Continuous Glucose Monitoring System During Hypoglycemia: Experience of the Diabetes Research in Children Network", *Diabetes Care*, vol. 27, No. 3, 2004, pp. 722-726.

Turner, A., et al., "Diabetes Mellitus: Biosensors for Research and Management", *Biosensors*, vol. 1, 1985, pp. 85-115.

Turner, R. F., et al., "A Biocompatible Enzyme Electrode for Continuous in vivo Glucose Monitoring in Whole Blood", *Sensors and Actuators B*, vol. 1, 1990, pp. 561-564.

Tuzhi, P., et al., "Constant Potential Pretreatment of Carbon Fiber Electrodes for in Vivo Electrochemistry", *Analytical Letters*, vol. 24 No. 6, 1991, pp. 935-945.

Umana, M., "Protein-Modified Electrochemically Active Biomaterial Surface", *U.S. Army Research Office, Analytical and Chemical Sciences Research Triangle Institute*, 1988, pp. 1-9.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Urban, G., et al., "Miniaturized Thin-Film Biosensors Using Covalently Immobilized Glucose Oxidase", *Biosensors & Bioelectronics*, vol. 6, 1991, pp. 555-562.

Velho, G., et al., "In Vitro and in Vivo Stability of Electrode Potentials in Needle-Type Glucose Sensors", *Diabetes*, vol. 38, No. 2, 1989, pp. 164-171.

Velho, G., et al., "Strategies for Calibrating a Subcutaneous Glucose Sensor", *Biochimica Acta*, vol. 48, 1989, pp. 957-964.

Von Woedtke, T., et al., "In Situ Calibration of Implanted Electrochemical Glucose Sensors", *Biomedica Biochimica Acta*, vol. 48, 1989, pp. 943-952.

Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.

Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64 No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.

Wang, J., et al., "Activation of Glassy Carbon Electrodes by Alternating Current Electrochemical Treatment", *Analytica Chimica Acta*, vol. 167, 1985, pp. 325-334.

Wang, J., et al., "Amperometric Biosensing of Organic Peroxides with Peroxidase-Modified Electrodes", *Analytica Chimica Acta*, vol. 254, 1991, pp. 81-88.

Wang, J., et al., "Screen-Printable Sol-Gel Enzyme-Containing Carbon Inks", *Analytical Chemistry*, vol. 68, No. 15, 1996, pp. 2705-2708.

Wang, J., et al., "Sol-Gel-Derived Metal-Dispersed Carbon Composite Amperometric Biosensors", *Electroanalysis*, vol. 9, No. 1, 1997, pp. 52-55.

Williams, D. L., et al., "Electrochemical-Enzymatic Analysis of Blood Glucose and Lactate", *Analytical Chemistry*, vol. 42, No. 1, 1970, pp. 118-121.

Wilson, G. S., et al., "Progress Toward the Development of an Implantable Sensor for Glucose", *Clinical Chemistry*, vol. 38, No. 9, 1992, pp. 1613-1617.

Yabuki, S., et al., "Electro-Conductive Enzyme Membrane", *Journal of the Chemical Society, Chemical Communications*, 1989, pp. 945-946.

Yang, C., et al., "A Comparison of Physical Properties and Fuel Cell Performance of Nafion and Zirconium Phosphate/Nafion Composite Membranes," *Journal of Membrane Science*, vol. 237, 2004, pp. 145-161.

Yang, L., et al., "Determination of Oxidase Enzyme Substrates Using Cross-Flow Thin-Layer Amperometry", *Electroanalysis*, vol. 8, No. 8-9, 1996, pp. 716-721.

Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.

Yao, T., "A Chemically-Modified Enzyme Membrane Electrode as an Amperometric Glucose Sensor", *Analytica Chimica Acta*, vol. 148, 1983, pp. 27-33.

Ye, L., et al., "High Current Density 'Wired' Quinoprotein Glucose Dehydrogenase Electrode", *Analytical Chemistry*, vol. 65, No. 3, 1993, pp. 238-241.

Yildiz, A., et al., "Evaluation of an Improved Thin-Layer Electrode", *Analytical Chemistry*, vol. 40, No. 7, 1968, pp. 1018-1024.

Zamzow, K., et al., "New Wearable Continuous Blood Glucose Monitor (BGM) and Artificial Pancreas (AP)", *Diabetes*, vol. 39, 1990, pp. 5A-20.

Zhang, Y., et al., "Application of Cell Culture Toxicity Tests to the Development of Implantable Biosensors", *Biosensors & Bioelectronics*, vol. 6, 1991, pp. 653-661.

Zhang, Y., et al., "Elimination of the Acetaminophen Interference in an Implantable Glucose Sensor", *Analytical Chemistry*, vol. 66, No. 7, 1994, pp. 1183-1188.

U.S. Appl. No. 12/117,665, Notice of Allowance mailed Feb. 23, 2011.
U.S. Appl. No. 12/117,665, Office Action mailed Jan. 20, 2011.
U.S. Appl. No. 12/117,665, Office Action mailed Jun. 28, 2010.
PCT Application No. PCT/US2008/063110, International Preliminary Report on Patentability and Written Opinion of the International Searching Authority mailed Nov. 26, 2009.
PCT Application No. PCT/US2008/063110, International Search Report and Written Opinion of the International Searching Authority mailed Nov. 21, 2008.
U.S. Appl. No. 12/117,677, Advisory Action mailed Jul. 27, 2011.
U.S. Appl. No. 12/117,677, Office Action mailed Apr. 14, 2011.
U.S. Appl. No. 12/117,677, Office Action mailed Jun. 9, 2010.
U.S. Appl. No. 12/117,677, Office Action mailed Mar. 9, 2012.
U.S. Appl. No. 12/117,677, Office Action mailed Nov. 4, 2010.
U.S. Appl. No. 12/117,677, Office Action mailed Oct. 14, 2011.
U.S. Appl. No. 12/117,681, Office Action mailed Apr. 5, 2010.
U.S. Appl. No. 12/117,681, Office Action mailed Mar. 5, 2012.
U.S. Appl. No. 12/117,681, Office Action mailed Sep. 14, 2010.
U.S. Appl. No. 12/117,685, Advisory Action mailed Jun. 7, 2010.
U.S. Appl. No. 12/117,685, Office Action mailed Apr. 8, 2011.
U.S. Appl. No. 12/117,685, Office Action mailed Aug. 16, 2010.
U.S. Appl. No. 12/117,685, Office Action mailed Mar. 22, 2010.
U.S. Appl. No. 12/117,685, Office Action mailed May 31, 2012.
U.S. Appl. No. 12/117,685, Office Action mailed Sep. 2, 2009.
U.S. Appl. No. 12/117,694, Office Action mailed Dec. 9, 2011.
U.S. Appl. No. 12/117,698, Office Action mailed Apr. 5, 2010.
U.S. Appl. No. 12/117,698, Office Action mailed Mar. 7, 2012.
U.S. Appl. No. 12/117,698, Office Action mailed Sep. 15, 2010.
U.S. Appl. No. 12/495,219, Office Action mailed Jun. 25, 2010.
U.S. Appl. No. 12/495,219, Office Action mailed Mar. 8, 2011.
U.S. Appl. No. 12/550,208, Office Action mailed Apr. 12, 2012.

U.S. Appl. No. 12/550,357, Notice of Allowance mailed Dec. 29, 2011.

U.S. Appl. No. 12/550,357, Office Action mailed Jan. 25, 2011.

U.S. Appl. No. 12/550,357, Office Action mailed Jul. 20, 2011.

ANALYTE MONITORING SYSTEM AND METHODS

RELATED APPLICATIONS

The present application is a continuation of U.S. patent application Ser. No. 12/117,665 filed May 8, 2008 now U.S. Pat. No. 7,928,850, which claims priority to U.S. provisional application No. 60/916,677 filed May 8, 2007, entitled "Analyte Monitoring System and Methods", the disclosures of each of which are incorporated herein by reference for all purposes.

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer. RF signals may be used to transmit the collected data. One aspect of certain analyte monitoring systems include a transcutaneous or subcutaneous analyte sensor configuration which is, for example, at least partially positioned through the skin layer of a subject whose analyte level is to be monitored. The sensor may use a two or three-electrode (work, reference and counter electrodes) configuration driven by a controlled potential (potentiostat) analog circuit connected through a contact system.

An analyte sensor may be configured so that a portion thereof is placed under the skin of the patient so as to contact analyte of the patient, and another portion or segment of the analyte sensor may be in communication with the transmitter unit. The transmitter unit may be configured to transmit the analyte levels detected by the sensor over a wireless communication link such as an RF (radio frequency) communication link to a receiver/monitor unit. The receiver/monitor unit may perform data analysis, among other functions, on the received analyte levels to generate information pertaining to the monitored analyte levels.

Transmission of control or command data over wireless communication link is often constrained to occur within a substantially short time duration. In turn, the time constraint in data communication imposes limits on the type and size of data that may be transmitted during the transmission time period.

In view of the foregoing, it would be desirable to have a method and apparatus for optimizing the RF communication link between two or more communication devices, for example, in a medical communication system.

SUMMARY

Devices and methods for analyte monitoring, e.g., glucose monitoring, are provided. Embodiments include transmitting information from a first location to a second, e.g., using a telemetry system such as RF telemetry. Systems herein include continuous analyte monitoring systems and discrete analyte monitoring system.

In one embodiment, a method including periodically receiving data including a count information related to an analyte sensor associated with the received data, and comparing the count information in each data periodically received, and when it is determined that the count information of the periodically received data is different, generating one or more signals related to the status of the analyte sensor, is disclosed, as well as devices and systems for the same.

These and other objects, features and advantages of the present invention will become more fully apparent from the following detailed description of the embodiments, the appended claims and the accompanying drawings.

DETAILED DESCRIPTION

As summarized above and as described in further detail below, in accordance with the various embodiments of the present invention, there is provided a method and system periodically receiving data including a count information related to an analyte sensor associated with the received data, and comparing the count information in each data periodically received, and when it is determined that the count information of the periodically received data is different, generating one or more signals related to the status of the analyte sensor.

Figure 1:
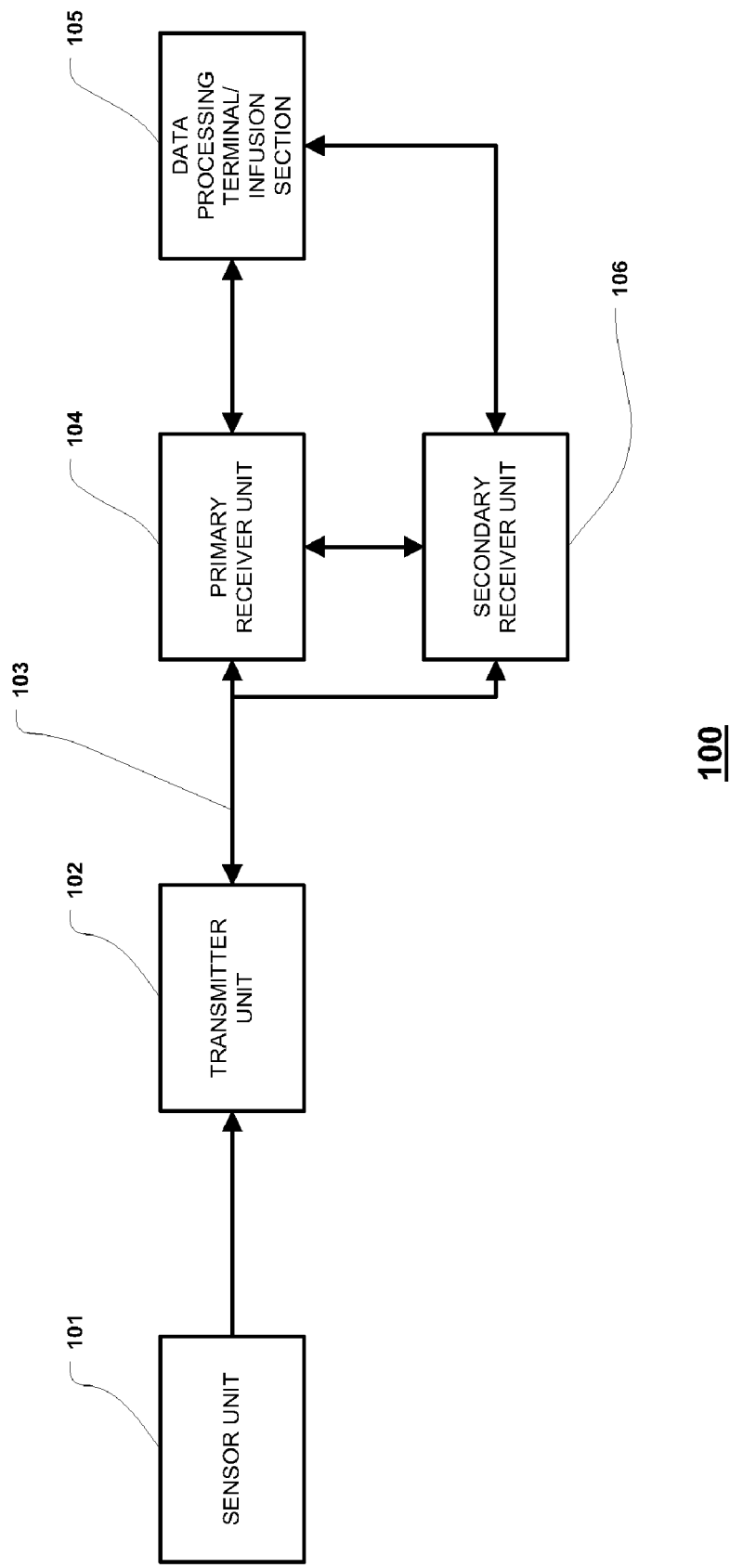
FIG. 1 illustrates a block diagram of a data monitoring and management system for practicing one or more embodiments of the present invention.

FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. More than one analyte may be monitored by a single system, e.g. a single analyte sensor.

The analyte monitoring system 100 includes a sensor unit 101, a transmitter unit 102 coupleable to the sensor unit 101, and a primary receiver unit 104 which is configured to communicate with the transmitter unit 102 via a bi-directional communication link 103. The primary receiver unit 104 may be further configured to transmit data to a data processing terminal 105 for evaluating the data received by the primary receiver unit 104. Moreover, the data processing terminal 105 in one embodiment may be configured to receive data directly from the transmitter unit 102 via a communication link which may optionally be configured for bi-directional communication. Accordingly, transmitter unit 102 and/or receiver unit 104 may include a transceiver.

Also shown in FIG. 1 is an optional secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each or one of the primary receiver unit 104 and the data processing terminal 105. As discussed in further detail below, in one embodiment of the present invention, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, pager, mobile phone, PDA, for example. Alternatively, the secondary receiver unit 106 may be configured with the same or substantially similar functionality as the primary receiver unit 104. The receiver unit may be configured to be used in conjunction with a docking cradle unit, for example for one or more of the following or other functions: placement by bedside, for re-charging, for data management, for night time monitoring, and/or bi-directional communication device.

In one aspect sensor unit 101 may include two or more sensors, each configured to communicate with transmitter unit 102. Furthermore, while only one transmitter unit 102, communication link 103, and data processing terminal 105 are shown in the embodiment of the analyte monitoring system 100 illustrated in FIG. 1, it will be appreciated by one of ordinary skill in the art that the analyte monitoring system 100 may include one or more sensors, multiple transmitter units 102, communication links 103, and data processing terminals 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor unit 101 is physically positioned in or on the body of a user whose analyte level is being monitored. The sensor unit 101 may be configured to continuously sample the analyte level of the user and convert the sampled analyte level into a corresponding data signal for transmission by the transmitter unit 102. In certain embodiments, the transmitter unit 102 may be physically coupled to the sensor unit 101 so that both devices are integrated in a single housing and positioned on the user's body. The transmitter unit 102 may perform data processing such as filtering and encoding on data signals and/or other functions, each of which corresponds to a sampled analyte level of the user, and in any event transmitter unit 102 transmits analyte information to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor unit 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 and/or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump (external or implantable) or the like, which may be configured to administer insulin to patients, and which may be configured to communicate with the receiver unit 104 for receiving, among others, the measured analyte level. Alternatively, the receiver unit 104 may be configured to integrate or otherwise couple to an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via the wireless communication link. More specifically, the data processing terminal 105 may in one embodiment be configured to receive data directly from the transmitter unit 102 via the communication link (not shown), where the communication link (not shown), as described above, may be configured for bi-directional communication.

In this embodiment, the data processing terminal 105 which may include an insulin pump, may be configured to receive the analyte signals from the transmitter unit 102, and thus, incorporate the functions of the receiver 104 including data processing for managing the patient's insulin therapy and analyte monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPAA requirements) while avoiding potential data collision and interference.

Figure 2:
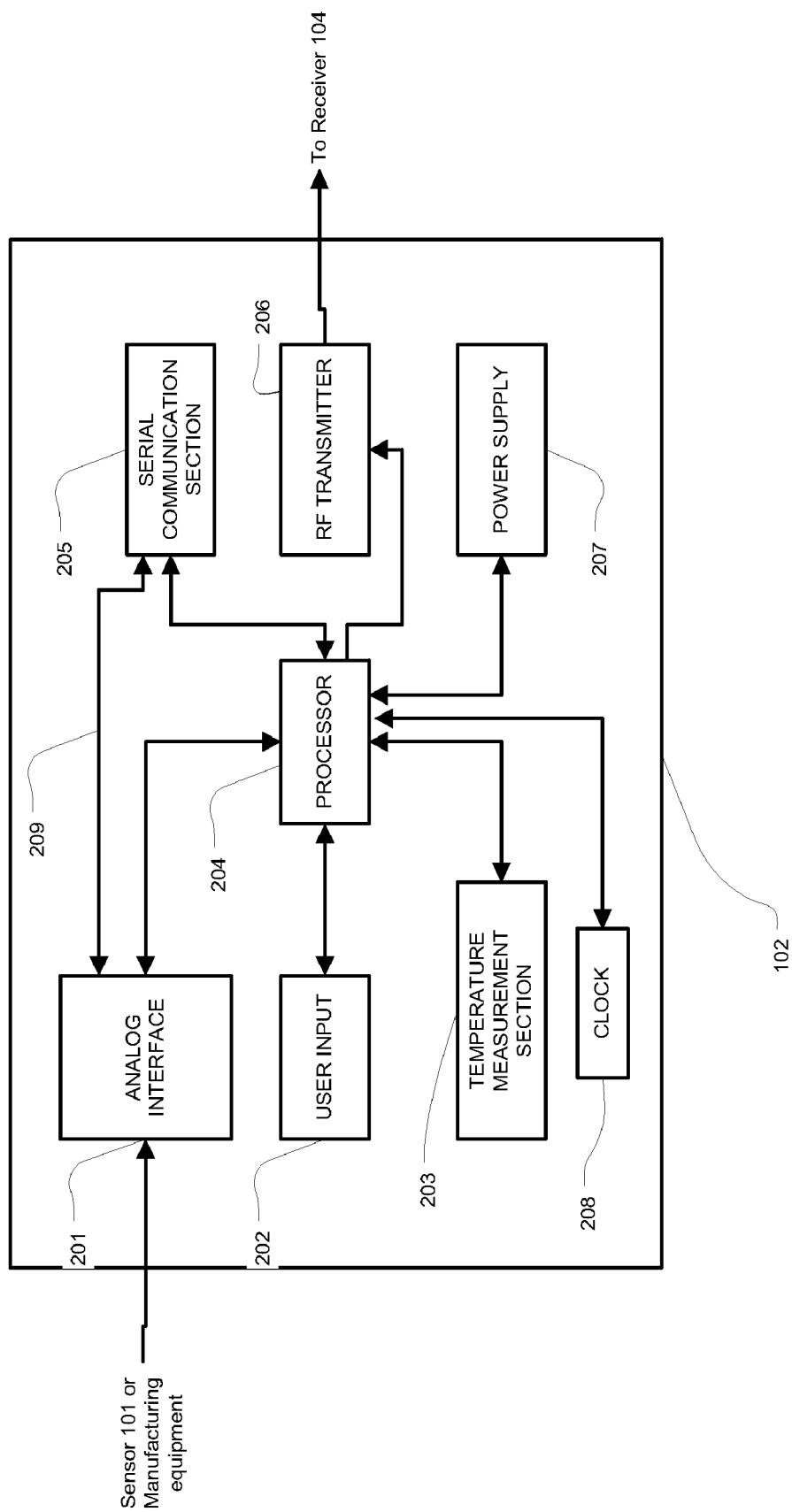
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor unit 101 (FIG. 1), a user input 202, and a temperature detection section 203, each of which is operatively coupled to a transmitter processor 204 such as a central processing unit (CPU). Although not shown in FIG. 2, there are provided four contacts, three of which are electrodes—work electrode, guard contact, reference electrode, and counter electrode, each operatively coupled to the analog interface 201 of the transmitter unit 102 for connection to the sensor unit 101 (FIG. 1). In one embodiment, each of the work electrode (not shown), guard contact (not shown), reference electrode (not shown), and counter electrode (not shown) may be made using a conductive material that is either printed or etched or ablated, for example, such as carbon which may be printed, or a metal such as a metal foil (e.g., gold) or the like, which may be etched or ablated or otherwise processed to provide one or more electrodes. Fewer or greater electrodes and/or contact may be provided in certain embodiments.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor unit 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor unit 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor unit 101. The stored information may be retrieved and processed for transmission to the primary receiver unit 104 under the control of the transmitter processor 204. Furthermore, the power supply 207 may include a commercially available battery, which may be a rechargeable battery.

In certain embodiments, the transmitter unit 102 is also configured such that the power supply section 207 is capable of providing power to the transmitter for a minimum of about three months of continuous operation, e.g., after having been stored for about eighteen months such as stored in a low-power (non-operating) mode. In one embodiment, this may be achieved by the transmitter processor 204 operating in low power modes in the non-operating state, for example, drawing no more than approximately 1 μA of current. Indeed, in one embodiment, a step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. In certain embodiments, the RF transmitter 206 of the transmitter unit 102 may be configured for operation in the frequency band of approximately 315 MHz to approximately 322 MHz, for example, in the United States. In certain embodiments, the RF transmitter 206 of the transmitter unit 102 may be configured for operation in the frequency band of approximately 400 MHz to approximately 470 MHz. Further, in one embodiment, the RF transmitter 206 is configured to modulate the carrier frequency by performing Frequency Shift Keying and Manchester encoding. In one embodiment, the data transmission rate is about 19,200 symbols per second, with a minimum transmission range for communication with the primary receiver unit 104.

Referring yet again to FIG. 2, also shown is a leak detection circuit 214 coupled to the guard electrode (G) 211 and the processor 204 in the transmitter unit 102 of the data monitoring and management system 100. The leak detection circuit 214 in accordance with one embodiment of the present invention may be configured to detect leakage current in the sensor unit 101 to determine whether the measured sensor data are corrupt or whether the measured data from the sensor 101 is accurate. Exemplary analyte systems that may be employed are described in, for example, U.S. Pat. Nos. 6,134,461, 6,175,752, 6,121,611, 6,560,471, 6,746,582, and elsewhere, the disclosure of each of which are incorporated by reference for all purposes.

Figure 3:
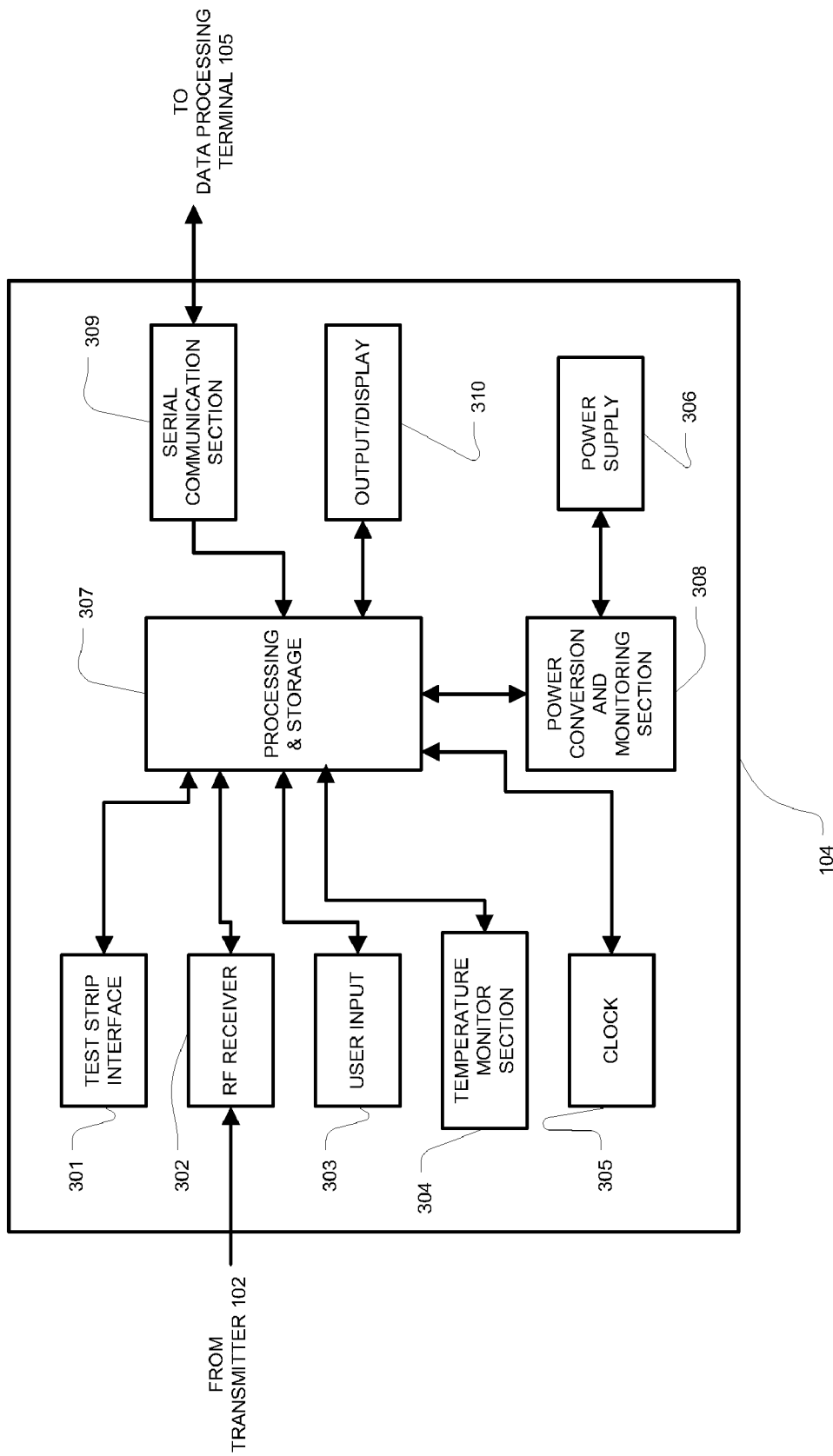
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the primary receiver unit 104 includes an analyte test strip, e.g., blood glucose test strip, interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose may be used to calibrate the sensor unit 101 or otherwise. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in suboptimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 104 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 may be configured to synchronize with a transmitter, e.g., using Manchester decoding or the like, as well as error detection and correction upon the encoded data signals received from the transmitter unit 102 via the communication link 103.

Additional description of the RF communication between the transmitter 102 and the primary receiver 104 (or with the secondary receiver 106) that may be employed in embodiments of the subject invention is disclosed in pending application Ser. No. 11/060,365 filed Feb. 16, 2005 entitled "Method and System for Providing Data Communication in Continuous Glucose Monitoring and Management System" the disclosure of which is incorporated herein by reference for all purposes.

Referring to the Figures, in one embodiment, the transmitter 102 (FIG. 1) may be configured to generate data packets for periodic transmission to one ore more of the receiver units 104, 106, where each data packet includes in one embodiment two categories of data—urgent data and non-urgent data. For example, urgent data such as for example glucose data from the sensor and/or temperature data associated with the sensor may be packed in each data packet in addition to non-urgent data, where the non-urgent data is rolled or varied with each data packet transmission.

That is, the non-urgent data is transmitted at a timed interval so as to maintain the integrity of the analyte monitoring system without being transmitted over the RF communication link with each data transmission packet from the transmitter 102. In this manner, the non-urgent data, for example that are not time sensitive, may be periodically transmitted (and not with each data packet transmission) or broken up into predetermined number of segments and sent or transmitted over multiple packets, while the urgent data is transmitted substantially in its entirety with each data transmission.

Referring again to the Figures, upon receiving the data packets from the transmitter 102, the one or more receiver units 104, 106 may be configured to parse the received the data packet to separate the urgent data from the non-urgent data, and also, may be configured to store the urgent data and the non-urgent data, e.g., in a hierarchical manner. In accordance with the particular configuration of the data packet or the data transmission protocol, more or less data may be transmitted as part of the urgent data, or the non-urgent rolling data. That is, within the scope of the present disclosure, the specific data packet implementation such as the number of bits per packet, and the like, may vary based on, among others, the communication protocol, data transmission time window, and so on.

In an exemplary embodiment, different types of data packets may be identified accordingly. For example, identification in certain exemplary embodiments may include—(1) single sensor, one minute of data, (2) two or multiple sensors, (3) dual sensor, alternate one minute data, and (4) response packet. For single sensor one minute data packet, in one embodiment, the transmitter 102 may be configured to generate the data packet in the manner, or similar to the manner, shown in Table 1 below.

TABLE 1

Single sensor, one minute of data

| Number of Bits | Data Field |
| --- | --- |
| 8 | Transmit Time |
| 14 | Sensor1 Current Data |
| 14 | Sensor1 Historic Data |
| 8 | Transmit Status |
| 12 | AUX Counter |
| 12 | AUX Thermistor 1 |
| 12 | AUX Thermistor 2 |
| 8 | Rolling-Data-1 |

As shown in Table 1 above, the transmitter data packet in one embodiment may include 8 bits of transmit time data, 14 bits of current sensor data, 14 bits of preceding sensor data, 8 bits of transmitter status data, 12 bits of auxiliary counter data, 12 bits of auxiliary thermistor 1 data, 12 bits of auxiliary thermistor 1 data and 8 bits of rolling data. In one embodiment of the present invention, the data packet generated by the transmitter for transmission over the RF communication link may include all or some of the data shown above in Table 1.

Referring back, the 14 bits of the current sensor data provides the real time or current sensor data associated with the detected analyte level, while the 14 bits of the sensor historic or preceding sensor data includes the sensor data associated with the detected analyte level one minute ago. In this manner, in the case where the receiver unit 104, 106 drops or fails to successfully receive the data packet from the transmitter 102 in the minute by minute transmission, the receiver unit 104, 106 may be able to capture the sensor data of a prior minute transmission from a subsequent minute transmission.

Referring again to Table 1, the Auxiliary data in one embodiment may include one or more of the patient's skin temperature data, a temperature gradient data, reference data, and counter electrode voltage. The transmitter status field may include status data that is configured to indicate corrupt data for the current transmission (for example, if shown as BAD status (as opposed to GOOD status which indicates that the data in the current transmission is not corrupt)). Furthermore, the rolling data field is configured to include the non-urgent data, and in one embodiment, may be associated with the time-hop sequence number. In addition, the Transmitter Time field in one embodiment includes a protocol value that is configured to start at zero and is incremented by one with each data packet. In one aspect, the transmitter time data may be used to synchronize the data transmission window with the receiver unit 104, 106, and also, provide an index for the Rolling data field.

In a further embodiment, the transmitter data packet may be configured to provide or transmit analyte sensor data from two or more independent analyte sensors. The sensors may relate to the same or different analyte or property. In such a case, the data packet from the transmitter 102 may be configured to include 14 bits of the current sensor data from both sensors in the embodiment in which 2 sensors are employed. In this case, the data packet does not include the immediately preceding sensor data in the current data packet transmission. Instead, a second analyte sensor data is transmitted with a first analyte sensor data.

TABLE 2

Dual sensor data

| Number of Bits | Data Field |
| --- | --- |
| 8 | Transmit Time |
| 14 | Sensor1 Current Data |
| 14 | Sensor2 Current Data |
| 8 | Transmit Status |
| 12 | AUX Counter |
| 12 | AUX Thermistor 1 |
| 12 | AUX Thermistor 2 |
| 8 | Rolling-Data-1 |

In a further embodiment, the transmitter data packet may be alternated with each transmission between two analyte sensors, for example, alternating between the data packet shown in Table 3 and Table 4 below.

TABLE 3

Sensor Data Packet Alternate 1

| Number of Bits | Data Field |
| --- | --- |
| 8 | Transmitter Time |
| 14 | Sensor1 Current Data |
| 14 | Sensor1 Historic Data |
| 8 | Transmit Status |
| 12 | AUX Counter |
| 12 | AUX Thermistor 1 |
| 12 | AUX Thermistor 2 |
| 8 | Rolling-Data-1 |

TABLE 4

Sensor Data Packet Alternate 2

| Number of Bits | Data Field |
| --- | --- |
| 8 | Transmitter Time |
| 14 | Sensor1 Current Data |
| 14 | Sensor2 Current Data |
| 8 | Transmit Status |
| 12 | AUX Counter |
| 12 | AUX Thermistor 1 |
| 12 | AUX Thermistor 2 |
| 8 | Rolling-Data-1 |

As shown above in reference to Tables 3 and 4, the minute by minute data packet transmission from the transmitter 102 (FIG. 1) in one embodiment may alternate between the data packet shown in Table 3 and the data packet shown in Table 4. More specifically, the transmitter 102 may be configured in one embodiment transmit the current sensor data of the first sensor and the preceding sensor data of the first sensor (Table 3), as well as the rolling data, and further, at the subsequent transmission, the transmitter 102 may be configured to transmit the current sensor data of the first and the second sensor in addition to the rolling data.

In one embodiment, the rolling data transmitted with each data packet may include a sequence of various predetermined types of data that are considered not-urgent or not time sensitive. That is, in one embodiment, the following list of data shown in Table 5 may be sequentially included in the 8 bits of transmitter data packet, and not transmitted with each data packet transmission of the transmitter (for example, with each 60 second data transmission from the transmitter 102).

TABLE 5

Rolling Data

| Time Slot | Bits | Rolling-Data |
| --- | --- | --- |
| 0 | 8 | Mode |
| 1 | 8 | Glucose1 Slope |
| 2 | 8 | Glucose2 Slope |
| 3 | 8 | Ref-R |
| 4 | 8 | Hobbs Counter, Ref-R |
| 5 | 8 | Hobbs Counter |
| 6 | 8 | Hobbs Counter |
| 7 | 8 | Sensor Count |

As can be seen from Table 5 above, in one embodiment, a sequence of rolling data are appended or added to the transmitter data packet with each data transmission time slot. In one embodiment, there may be 256 time slots for data transmission by the transmitter 102 (FIG. 1), and where, each time slot is separated by approximately 60 second interval. For example, referring to the Table 5 above, the data packet in transmission time slot 0 (zero) may include operational mode data (Mode) as the rolling data that is appended to the transmitted data packet. At the subsequent data transmission time slot (for example, approximately 60 seconds after the initial time slot (0), the transmitted data packet may include the analyte sensor 1 calibration factor information (Glucose1 slope) as the rolling data. In this manner, with each data transmission, the rolling data may be updated over the 256 time slot cycle.

Referring again to Table 5, each rolling data field is described in further detail for various embodiments. For example, the Mode data may include information related to the different operating modes such as, but not limited to, the data packet type, the type of battery used, diagnostic routines, single sensor or multiple sensor input, type of data transmission (rf communication link or other data link such as serial connection). Further, the Glucose1-slope data may include an 8-bit scaling factor or calibration data for first sensor (scaling factor for sensor 1 data), while Glucose2-slope data may include an 8-bit scaling factor or calibration data for the second analyte sensor (in the embodiment including more than one analyte sensors).

In addition, the Ref-R data may include 12 bits of on-board reference resistor used to calibrate our temperature measurement in the thermister circuit (where 8 bits are transmitted in time slot 3, and the remaining 4 bits are transmitted in time slot 4), and the 20-bit Hobbs counter data may be separately transmitted in three time slots (for example, in time slot 4, time slot 5 and time slot 6) to add up to 20 bits. In one embodiment, the Hobbs counter may be configured to count each occurrence of the data transmission (for example, a packet transmission at approximately 60 second intervals) and may be incremented by a count of one (1).

In one aspect, the Hobbs counter is stored in a nonvolatile memory of the transmitter unit 102 (FIG. 1) and may be used to ascertain the power supply status information such as, for example, the estimated battery life remaining in the transmitter unit 102. That is, with each sensor replacement, the Hobbs counter is not reset, but rather, continues the count with each replacement of the sensor unit 101 to establish contact with the transmitter unit 102 such that, over an extended usage time period of the transmitter unit 102, it may be possible to determine, based on the Hobbs count information, the amount of consumed battery life in the transmitter unit 102, and also, an estimated remaining life of the battery in the transmitter unit 102.

That is, in one embodiment, the 20 bit Hobbs counter is incremented by one each time the transmitter unit 102 transmits a data packet (for example, approximately each 60 seconds), and based on the count information in the Hobbs counter, in one aspect, the battery life of the transmitter unit 102 may be estimated. In this manner, in configurations of the transmitter unit 620 (see FIG. 6) where the power supply is not a replaceable component but rather, embedded within the housing the transmitter unit 620, it is possible to estimate the remaining life of the embedded battery within the transmitter unit 620. Moreover, the Hobbs counter is configured to remain persistent in the memory device of the transmitter unit 620 such that, even when the transmitter unit power is turned off or powered down (for example, during the periodic sensor unit replacement, RF transmission turned off period and the like), the Hobbs counter information is retained.

Referring to Table 5 above, the transmitted rolling data may also include 8 bits of sensor count information (for example, transmitted in time slot 7). The 8 bit sensor counter is incremented by one each time a new sensor unit is connected to the transmitter unit. The ASIC configuration of the transmitter unit (or a microprocessor based transmitter configuration or with discrete components) may be configured to store in a nonvolatile memory unit the sensor count information and transmit it to the primary receiver unit 104 (for example). In turn, the primary receiver unit 104 (and/or the secondary receiver unit 106) may be configured to determine whether it is receiving data from the transmitter unit that is associated with the same sensor unit (based on the sensor count information), or from a new or replaced sensor unit (which will have a sensor count incremented by one from the prior sensor count). In this manner, in one aspect, the receiver unit (primary or secondary) may be configured to prevent reuse of the same sensor unit by the user based on verifying the sensor count information associated with the data transmission received from the transmitter unit 102. In addition, in a further aspect, user notification may be associated with one or more of these parameters. Further, the receiver unit (primary or secondary) may be configured to detect when a new sensor has been inserted, and thus prevent erroneous application of one or more calibration parameters determined in conjunction with a prior sensor, that may potentially result in false or inaccurate analyte level determination based on the sensor data.

Figure 4:
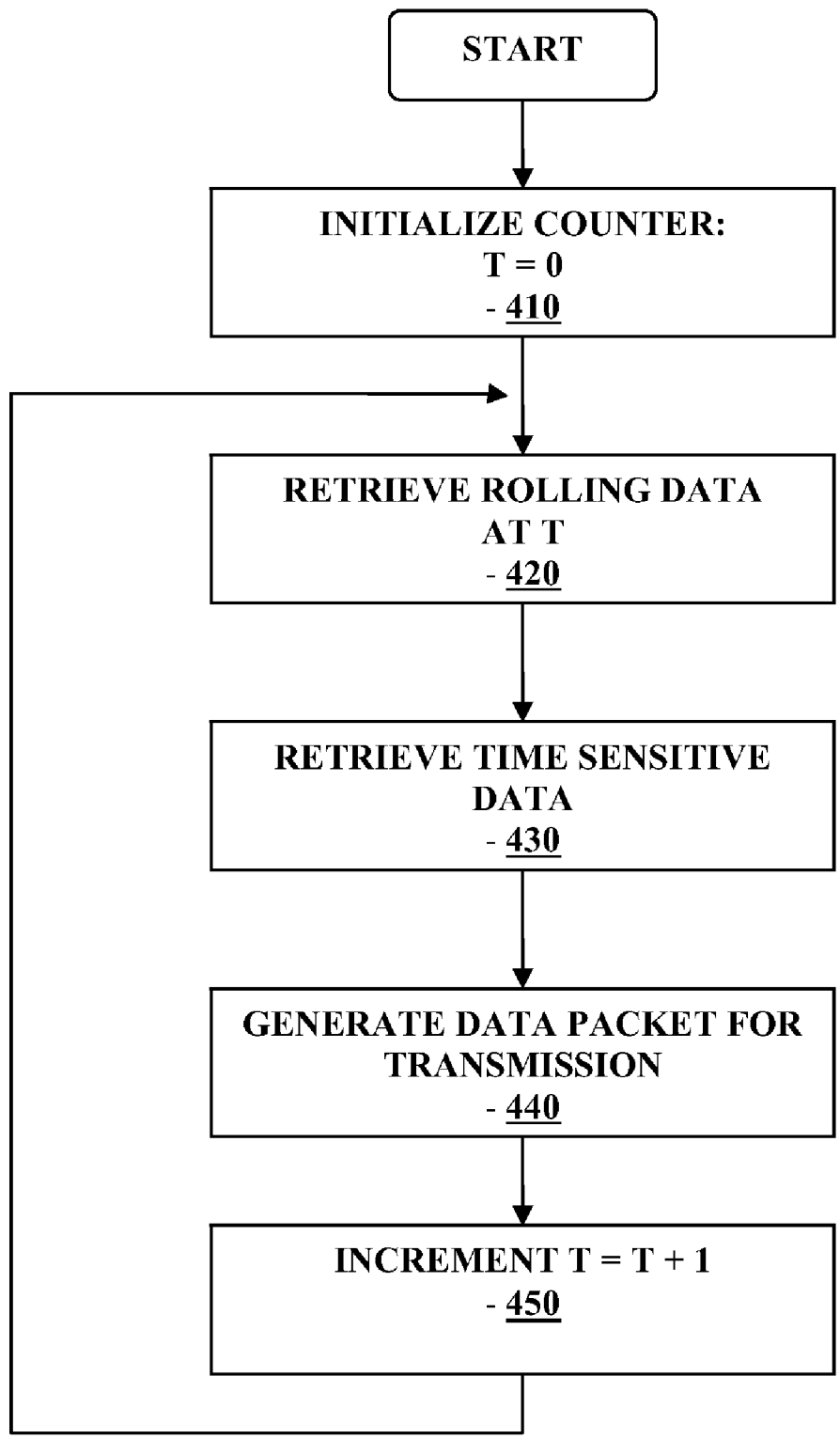
FIG. 4 is a flowchart illustrating data packet procedure including rolling data for transmission in accordance with one embodiment of the present invention.

FIG. 4 is a flowchart illustrating a data packet procedure including rolling data for transmission in accordance with one embodiment of the present invention. Referring to FIG. 4, in one embodiment, a counter is initialized (for example, to T=0) (410). Thereafter the associated rolling data is retrieved from memory device, for example (420), and also, the time sensitive or urgent data is retrieved (430). In one embodiment, the retrieval of the rolling data (420) and the retrieval of the time sensitive data (430) may be retrieved at substantially the same time.

Referring back to FIG. 4, with the rolling data and the time sensitive data, for example, the data packet for transmission is generated (440), an upon transmission, the counter is incremented by one and the routine returns to retrieval of the rolling data (420). In this manner, in one embodiment, the urgent time sensitive data as well as the non-urgent data may be incorporated in the same data packet and transmitted by the transmitter 102 (FIG. 1) to a remote device such as one or more of the receivers 104, 106. Furthermore, as discussed above, the rolling data may be updated at a predetermined time interval which is longer than the time interval for each data packet transmission from the transmitter 102 (FIG. 1).

Figure 5:
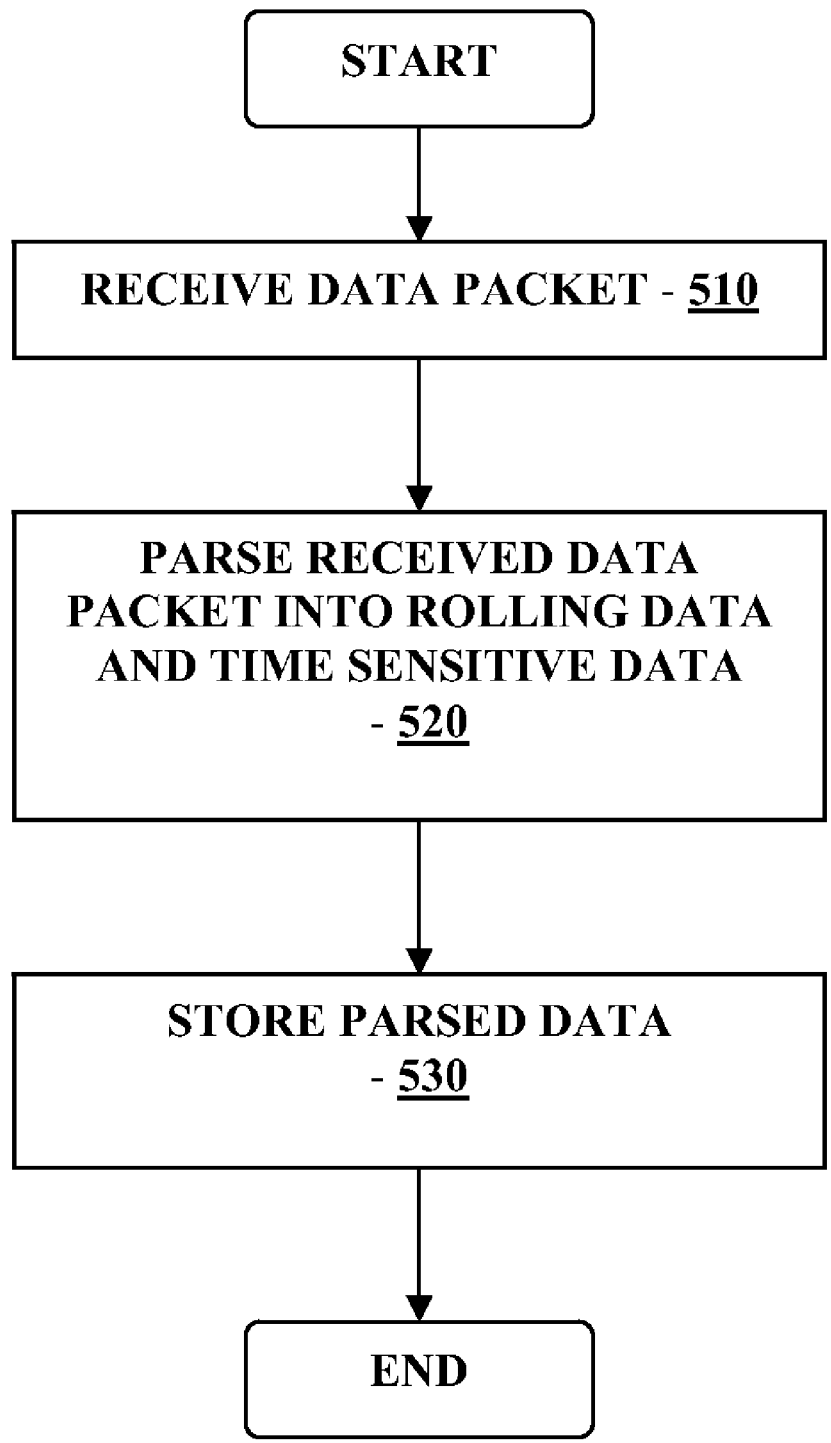
FIG. 5 is a flowchart illustrating data processing of the received data packet including the rolling data in accordance with one embodiment of the present invention.

FIG. 5 is a flowchart illustrating data processing of the received data packet including the rolling data in accordance with one embodiment of the present invention. Referring to FIG. 5, when the data packet is received (510) (for example, by one or more of the receivers 104, 106, in one embodiment, the received data packet is parsed so that the urgent data may be separated from the not-urgent data (stored in, for example, the rolling data field in the data packet). Thereafter the parsed data is suitably stored in an appropriate memory or storage device (530).

In the manner described above, in accordance with one embodiment of the present invention, there is provided method and apparatus for separating non-urgent type data (for example, data associated with calibration) from urgent type data (for example, monitored analyte related data) to be transmitted over the communication link to minimize the potential burden or constraint on the available transmission time. More specifically, in one embodiment, non-urgent data may be separated from data that is required by the communication system to be transmitted immediately, and transmitted over the communication link together while maintaining a minimum transmission time window. In one embodiment, the non-urgent data may be parsed or broken up in to a number of data segments, and transmitted over multiple data packets. The time sensitive immediate data (for example, the analyte sensor data, temperature data etc), may be transmitted over the communication link substantially in its entirety with each data packet or transmission.

Figure 6:
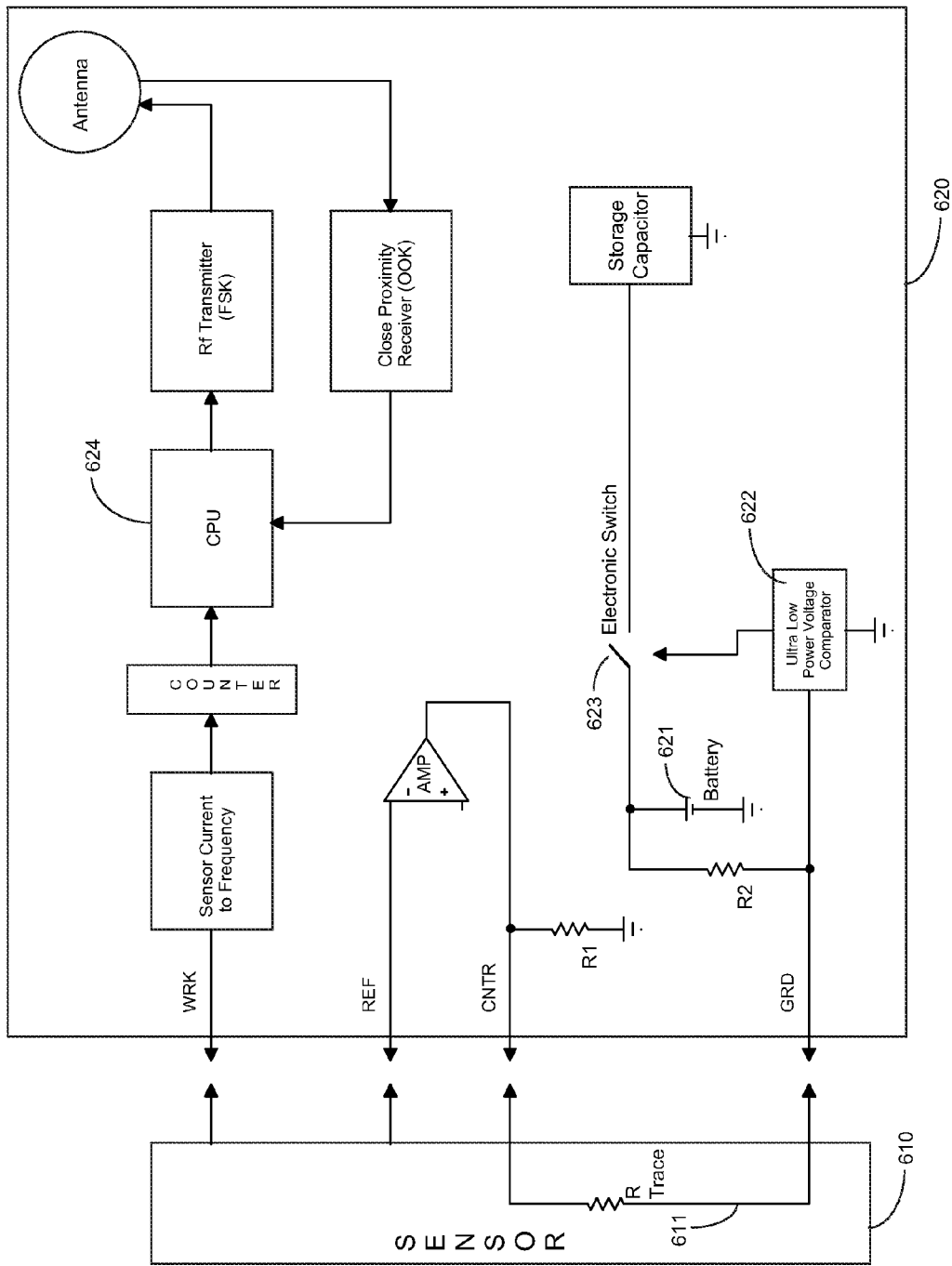
FIG. 6 is a block diagram illustrating the sensor unit and the transmitter unit of the data monitoring and management system of FIG. 1 in accordance with one embodiment of the present invention.

FIG. 6 is a block diagram illustrating the sensor unit and the transmitter unit of the data monitoring and management system of FIG. 1 in accordance with one embodiment of the present invention. Referring to FIG. 6, in one aspect, a transmitter unit 620 is provided in a substantially water tight and sealed housing. The transmitter unit 620 includes respective contacts (wrk, Ref, Cntr, and gnd) for respectively establishing electrical contact with one or more of the working electrode (not shown), the reference electrode (not shown), the counter electrode (not shown) and the ground terminal (or guard trace) (not shown) of the sensor unit 610. Also shown in FIG. 6 is a conductivity bar/trace 611 provided on the sensor unit 610. For example, in one embodiment, the conductivity bar/trace 611 may comprise a carbon trace on a substrate layer of the sensor unit 610. In this manner, in one embodiment, when the sensor unit 610 is coupled to the transmitter unit 610, electrical contact is established, for example, via the conductivity bar/trace 611 between the contact pads or points of the transmitter unit 620 (for example, at the counter electrode contact (cntr) and the ground terminal contact (gnd) such that the transmitter unit 620 may be powered for data communication.

That is, during manufacturing of the transmitter unit 620, in one aspect, the transmitter unit 620 is configured to include a power supply such as battery 621. Further, during the initial non-use period (e.g., post manufacturing sleep mode), the transmitter unit 620 is configured such that it is not used and thus drained by the components of the transmitter unit 620. During the sleep mode, and prior to establishing electrical contact with the sensor unit 610 via the conductivity bar/trace 611, the transmitter unit 620 is provided with a low power signal from, for example, a low power voltage comparator 622, via an electronic switch 623 to maintain the low power state of, for example, the transmitter unit 620 components. Thereafter, upon connection with the sensor unit 610, and establishing electrical contact via the conductivity bar/trace 611, the embedded power supply 621 of the transmitter unit 620 is activated or powered up so that some of all of the components of the transmitter unit 620 are configured to receive the necessary power signals for operations related to, for example, data communication, processing and/or storage.

In one aspect, since the transmitter unit 620 is configured to a sealed housing without a separate replaceable battery compartment, in this manner, the power supply of the battery 621 is preserved during the post manufacturing sleep mode prior to use.

In a further aspect, the transmitter unit 620 may be disposed or positioned on a separate on-body mounting unit that may include, for example, an adhesive layer (on its bottom surface) to firmly retain the mounting unit on the skin of the user, and which is configured to receive or firmly position the transmitter unit 620 on the mounting unit during use. In one aspect, the mounting unit may be configured to at least partially retain the position of the sensor unit 610 in a transcutaneous manner so that at least a portion of the sensor unit is in fluid contact with the analyte of the user. Example embodiments of the mounting or base unit and its cooperation or coupling with the transmitter unit are provided, for example, in U.S. Pat. No. 6,175,752, incorporated herein by reference for all purposes.

In such a configuration, the power supply for the transmitter unit 620 may be provided within the housing of the mounting unit such that, the transmitter unit 620 may be configured to be powered on or activated upon placement of the transmitter unit 620 on the mounting unit and in electrical contact with the sensor unit 610. For example, the sensor unit 610 may be provided pre-configured or integrated with the mounting unit and the insertion device such that, the user may position the sensor unit 610 on the skin layer of the user using the insertion device coupled to the mounting unit. Thereafter, upon transcutaneous positioning of the sensor unit 610, the insertion device may be discarded or removed from the mounting unit, leaving behind the transcutaneously positioned sensor unit 610 and the mounting unit on the skin surface of the user.

Thereafter, when the transmitter unit 620 is positioned on, over or within the mounting unit, the battery or power supply provided within the mounting unit is configured to electrically couple to the transmitter unit 620 and/or the sensor unit 610. Given that the sensor unit 610 and the mounting unit are provided as replaceable components for replacement every 3, 5, 7 days or other predetermined time periods, the user is conveniently not burdened with verifying the status of the power supply providing power to the transmitter unit 620 during use. That is, with the power supply or battery replaced with each replacement of the sensor unit 610, a new power supply or battery will be provided with the new mounting unit for use with the transmitter unit 620.

Referring to FIG. 6 again, in one aspect, when the sensor unit 610 is removed from the transmitter unit 620 (or vice versa), the electrical contact is broken and the conductivity bar/trace 611 returns to an open circuit. In this case, the transmitter unit 620 may be configured, to detect such condition and generate a last gasp transmission sent to the primary receiver unit 104 (and/or the secondary receiver unit 106) indicating that the sensor unit 610 is disconnected from the transmitter unit 620, and that the transmitter unit 620 is entering a powered down (or low power off) state. And the transmitter unit 620 is powered down into the sleep mode since the connection to the power supply (that is embedded within the transmitter unit 620 housing) is broken.

In this manner, in one aspect, the processor 624 of the transmitter unit 620 may be configured to generate the appropriate one or more data or signals associated with the detection of sensor unit 610 disconnection for transmission to the receiver unit 104 (FIG. 1), and also, to initiate the power down procedure of the transmitter unit 620. In one aspect, the components of the transmitter unit 620 may be configured to include application specific integrated circuit (ASIC) design with one or more state machines and one or more nonvolatile and/or volatile memory units such as, for example, EEPROMs and the like.

Referring again to FIGS. 1 and 6, in one embodiment, the communication between the transmitter unit 620 (or 102 of FIG. 1) and the primary receiver unit 104 (and/or the secondary receiver unit 106) may be based on close proximity communication where bi-directional (or uni-directional) wireless communication is established when the devices are physically located in close proximity to each other. That is, in one embodiment, the transmitter unit 620 may be configured to receive very short range commands from the primary receiver unit 104 (FIG. 1) and perform one or more specific operations based on the received commands from the receiver unit 104).

In one embodiment, to maintain secure communication between the transmitter unit and the data receiver unit, the transmitter unit ASIC may be configured to generate a unique close proximity key at power on or initialization. In one aspect, the 4 or 8 bit key may be generated based on, for example, the transmitter unit identification information, and which may be used to prevent undesirable or unintended communication. In a further aspect, the close proximity key may be generated by the receiver unit based on, for example, the transmitter identification information received by the transmitter unit during the initial synchronization or pairing procedure of the transmitter and the receiver units.

Referring again to FIGS. 1 and 6, in one embodiment, the transmitter unit ASIC configuration may include a 32 KHz oscillator and a counter which may be configured to drive the state machine in the transmitter unit ASIC. The transmitter ASIC configuration may include a plurality of close proximity communication commands including, for example, new sensor initiation, pairing with the receiver unit, and RF communication control, among others. For example, when a new sensor unit is positioned and coupled to the transmitter unit so that the transmitter unit is powered on, the transmitter unit is configured to detect or receive a command from the receiver unit positioned in close proximity to the transmitter unit. For example, the receiver unit may be positioned within a couple of inches from the on-body position of the transmitter unit, and when the user activates or initiates a command associated with the new sensor initiation from the receiver unit, the transmitter unit is configured to receive the command from the receiver and, in its response data packet, transmit, among others, its identification information back to the receiver unit.

In one embodiment, the initial sensor unit initiation command does not require the use of the close proximity key. However, other predefined or preconfigured close-proximity commands may be configured to require the use of the 8 bit key (or a key of a different number of bits). For example, in one embodiment, the receiver unit may be configured to transmit a RF on/off command to turn on/off the RF communication module or unit in the transmitter unit 102. Such RF on/off command in one embodiment includes the close proximity key as part of the transmitted command for reception by the transmitter unit.

During the period that the RF communication module or unit is turned off based on the received close proximity command, the transmitter unit does not transmit any data, including any glucose related data. In one embodiment, the glucose related data from the sensor unit which are not transmitted by the transmitter unit during the time period when the RF communication module or unit of the transmitter unit is turned off may be stored in a memory or storage unit of the transmitter unit for subsequent transmission to the receiver unit when the transmitter unit RF communication module or unit is turned back on based on the RF-on command from the receiver unit. In this manner, in one embodiment, the transmitter unit may be powered down (temporarily, for example, during air travel) without removing the transmitter unit from the on-body position.

Figure 7:
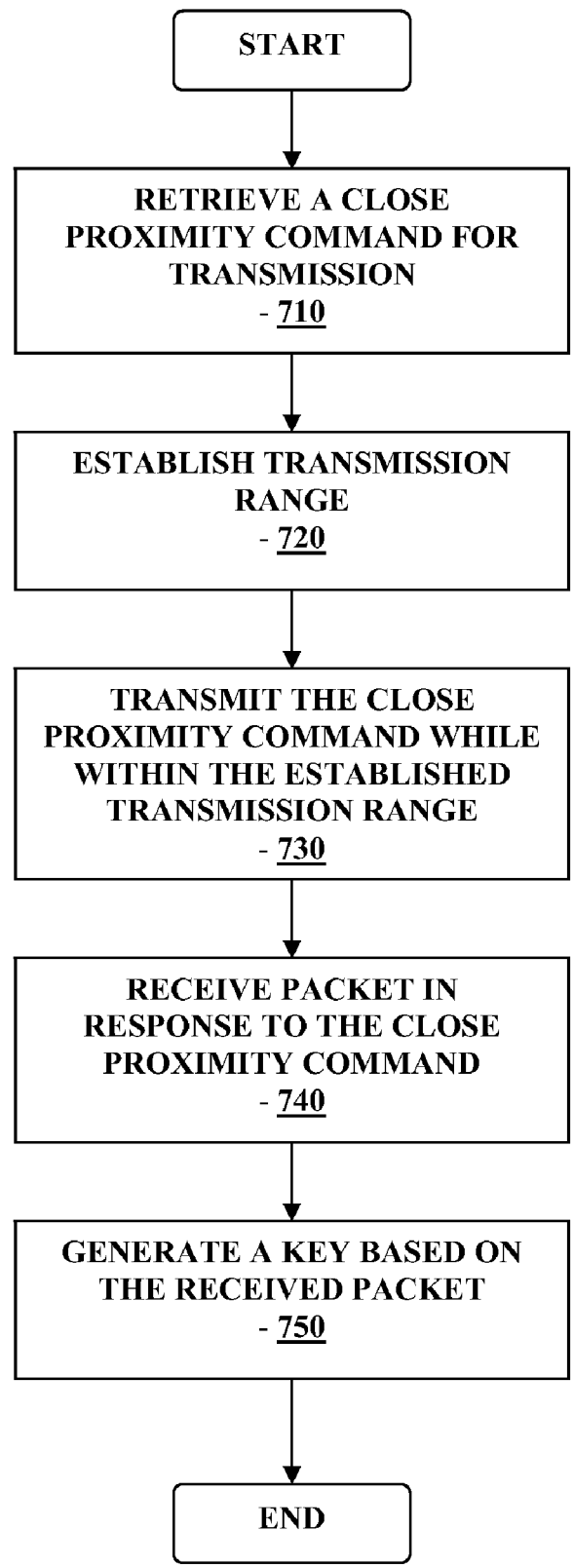
FIG. 7 is a flowchart illustrating data communication using close proximity commands in the data monitoring and management system of FIG. 1 in accordance with one embodiment of the present invention.

FIG. 7 is a flowchart illustrating data communication using close proximity commands in the data monitoring and management system of FIG. 1 in accordance with one embodiment of the present invention. Referring to FIG. 7, the primary receiver unit 104 (FIG. 1) in one aspect may be configured to retrieve or generate a close proximity command (710) for transmission to the transmitter unit 102. To establish the transmission range (720), the primary receiver unit 104 may be positioned physically close to (that is, within a predetermined distance from) the transmitter unit 102. For example, the transmission range for the close proximity communication may be established at approximately one foot distance or less between the transmitter unit 102 and the primary receiver unit 104. When the transmitter unit 102 and the primary receiver unit 104 are within the transmission range, the close proximity command, upon initiation from the receiver unit 104 may be transmitted to the transmitter unit 102 (730).

Referring back to FIG. 7, in response to the transmitted close proximity command, a response data packet or other responsive communication may be received (740). In one aspect, the response data packet or other responsive communication may include identification information of the transmitter unit 102 transmitting the response data packer or other response communication to the receiver unit 104. In one aspect, the receiver unit 104 may be configured to generate a key (for example, an 8 bit key or a key of a predetermined length) based on the transmitter identification information (750), and which may be used in subsequent close proximity communication between the transmitter unit 102 and the receiver unit 104.

In one aspect, the data communication including the generated key may allow the recipient of the data communication to recognize the sender of the data communication and confirm that the sender of the data communication is the intended data sending device, and thus, including data which is desired or anticipated by the recipient of the data communication. In this manner, in one embodiment, one or more close proximity commands may be configured to include the generated key as part of the transmitted data packet. Moreover, the generated key may be based on the transmitter ID or other suitable unique information so that the receiver unit 104 may use such information for purposes of generating the unique key for the bi-directional communication between the devices.

While the description above includes generating the key based on the transmitter unit 102 identification information, within the scope of the present disclosure, the key may be generated based on one or more other information associated with the transmitter unit 102, and/or the receiver unit combination. In a further embodiment, the key may be encrypted and stored in a memory unit or storage device in the transmitter unit 102 for transmission to the receiver unit 104.

Figure 8:
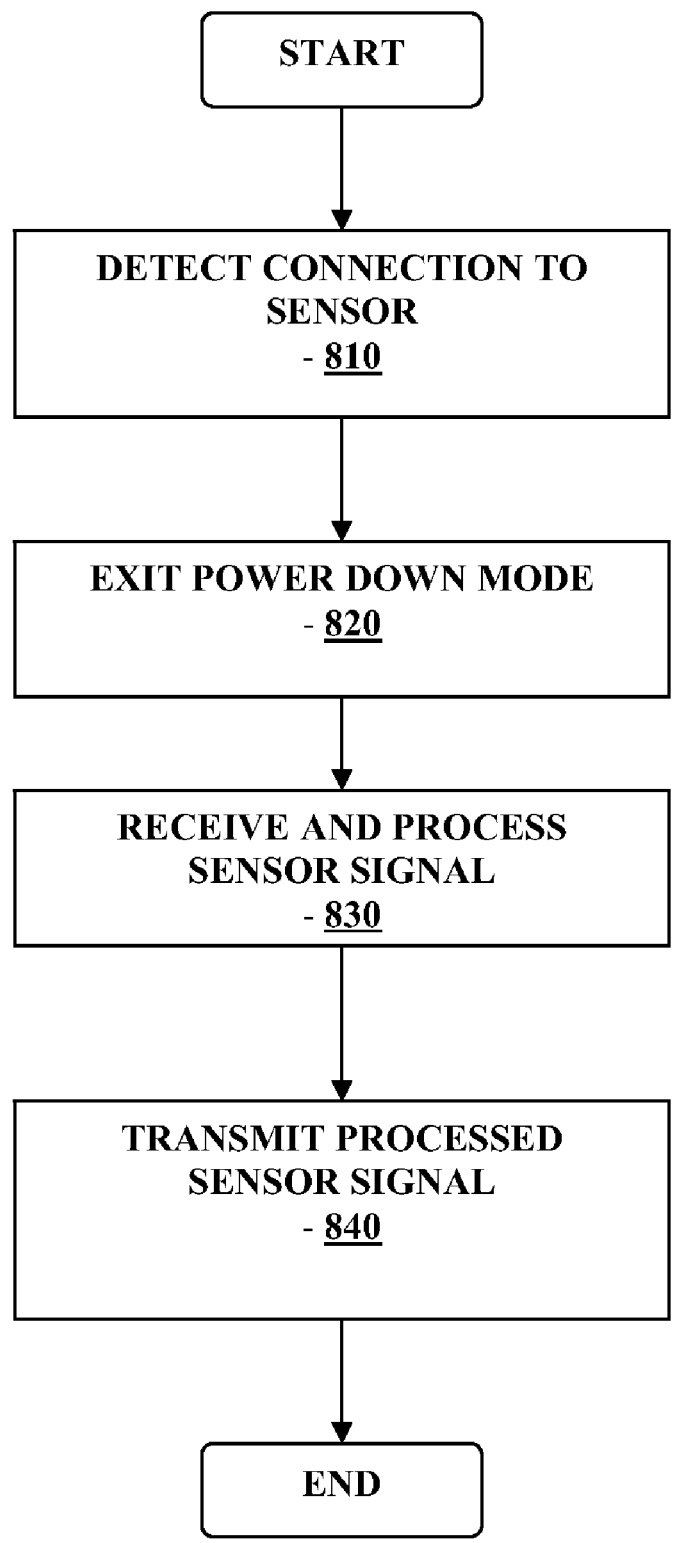
FIG. 8 is a flowchart illustrating sensor insertion detection routine in the data monitoring and management system of FIG. 1 in accordance with one embodiment of the present invention.

FIG. 8 is a flowchart illustrating sensor insertion detection routine in the data monitoring and management system of FIG. 1 in accordance with one embodiment of the present invention. Referring to FIG. 8, connection to an analyte sensor is detected (810), based on for example, a power up procedure where the sensor conduction trace 611 (FIG. 6) is configured to establish electrical contact with a predetermined one or more contact points on the transmitter unit 102. That is, when the sensor unit 101 (for example, the electrodes of the sensor) is correspondingly connected to the contact points on the transmitter unit 102, the transmitter unit 102 is configured to close the circuit connecting its power supply (for example, the battery 621 (FIG. 6)) to the components of the transmitter unit 102 and thereby exiting the power down or low power state into active or power up state.

In this manner, as discussed above, in one aspect, the transmitter unit 102 may be configured to include a power supply such as a battery 621 integrally provided within the sealed housing of the transmitter unit 102. When the transmitter unit 102 is connected or coupled to the respective electrodes of the analyte sensor that is positioned in a transcutaneous manner under the skin layer of the patient, the transmitter unit 102 is configured to wake up from its low power or sleep state (820), and power up the various components of the transmitter unit 102. In the active state, the transmitter unit 102 may be further configured to receive and process sensor signals received from the analyte sensor (FIG. 1) (830), and thereafter, transmit the processed sensor signals (840) to, for example, the receiver unit 104 (FIG. 1).

Accordingly, in one aspect, the sensor unit 610 (FIG. 6) may be provided with a conduction trace 611 which may be used to wake up or exit the transmitter unit from its post manufacturing sleep mode into an active state, by for example, establishing a closed circuit with the power supply provided within the transmitter unit 102.

Figure 9:
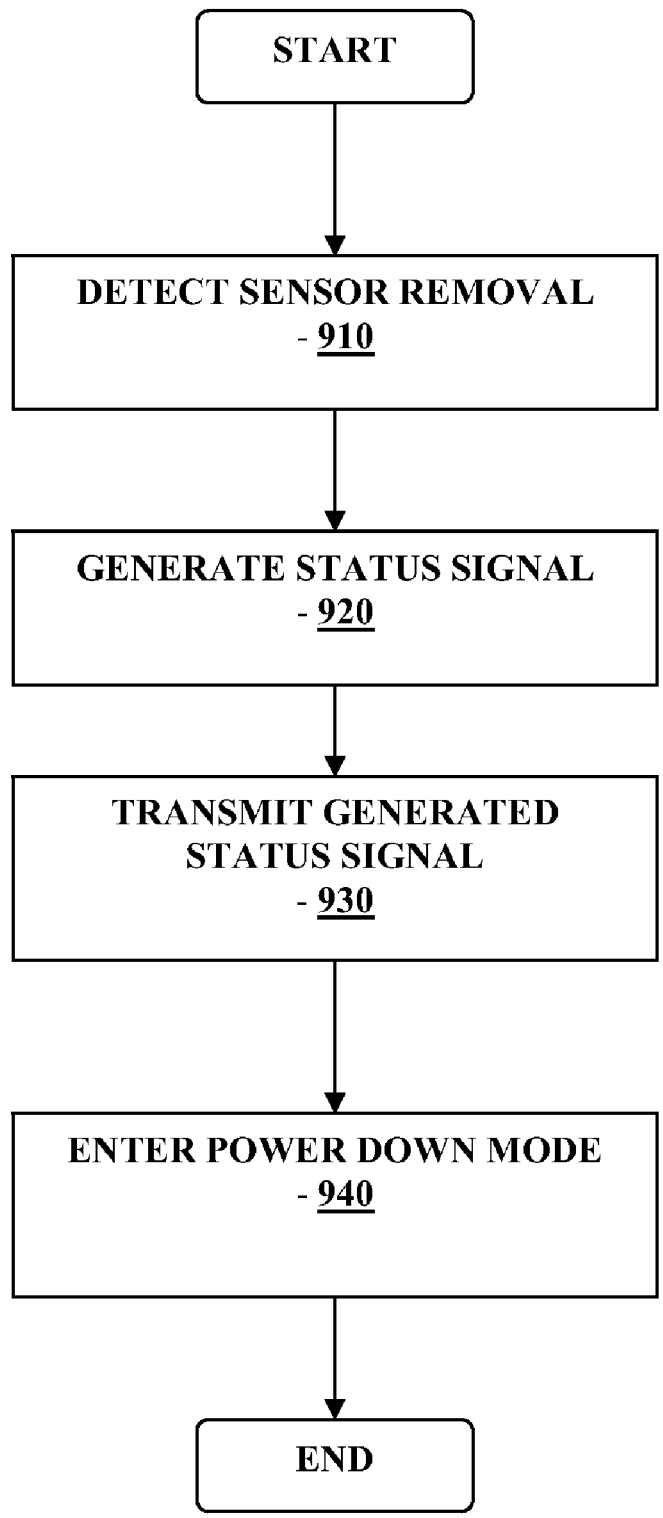
FIG. 9 is a flowchart illustrating sensor removal detection routine in the data monitoring and management system of FIG. 1 in accordance with one embodiment of the present invention.

FIG. 9 is a flowchart illustrating sensor removal detection routine in the data monitoring and management system of FIG. 1 in accordance with one embodiment of the present invention. Referring to FIG. 9, when the sensor removal is detected (910) for example, based on detaching or removing the transmitter unit 102 that was in contact with the sensor unit 101, one or more status signal is generated (920), that includes, for example, an indication that the sensor removal state has been detected, and/or an indication that the transmitter unit 102 will enter a sleep mode or a powered down status. Thereafter, the generated status signal in one aspect is transmitted, for example, to the receiver unit 104 (930), and the transmitter unit 102 is configured to enter the power down mode or low power sleep mode (940).

In this manner, in one aspect, when the transmitter unit 102 is disconnected with an active sensor unit 101, the transmitter unit 102 is configured to notify the receiver unit 104 that the sensor unit 101 has been disconnected or otherwise, signals from the sensor unit 101 is no longer received by the transmitter unit 102. After transmitting the one or more signals to notify the receiver unit 104, the transmitter unit 102 in one embodiment is configured to enter sleep mode or low power state during which no data related to the monitored analyte level is transmitted to the receiver unit 104.

Figure 10:
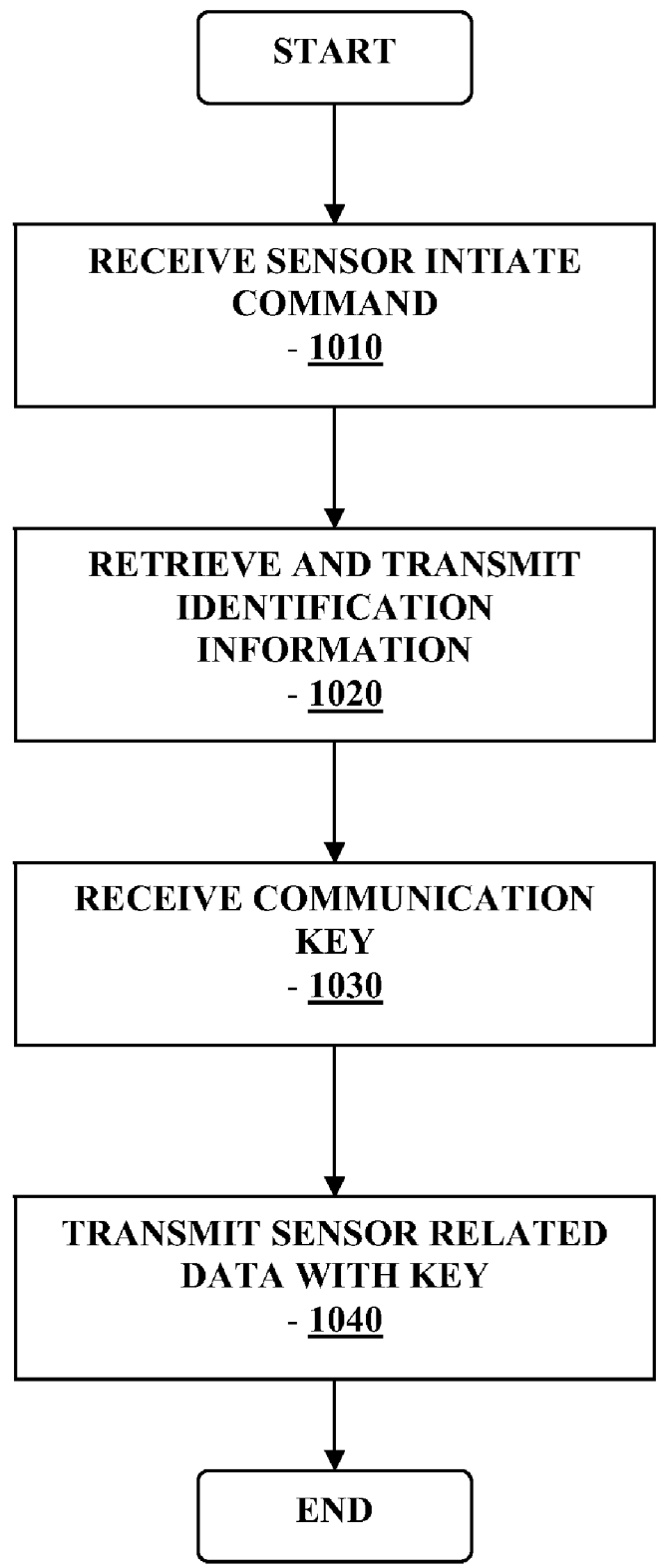
FIG. 10 is a flowchart illustrating the pairing or synchronization routine in the data monitoring and management system of FIG. 1 in accordance with one embodiment of the present invention.

FIG. 10 is a flowchart illustrating the pairing or synchronization routine in the data monitoring and management system of FIG. 1 in accordance with one embodiment of the present invention. Referring to FIG. 10, in one embodiment, the transmitter unit 102 may be configured to receive a sensor initiate close proximity command (1010) from the receiver unit 104 positioned within the close transmission range. Based on the received sensor initiate command, the transmitter unit identification information may be retrieved (for example, from a nonvolatile memory) and transmitted (1020) to the receiver unit 104 or the sender of the sensor initiate command.

Referring back to FIG. 10, a communication key (1030) optionally encrypted is received in one embodiment, and thereafter, sensor related data is transmitted with the communication key on a periodic basis such as, every 60 seconds, five minutes, or any suitable predetermined time intervals.

Figure 11:
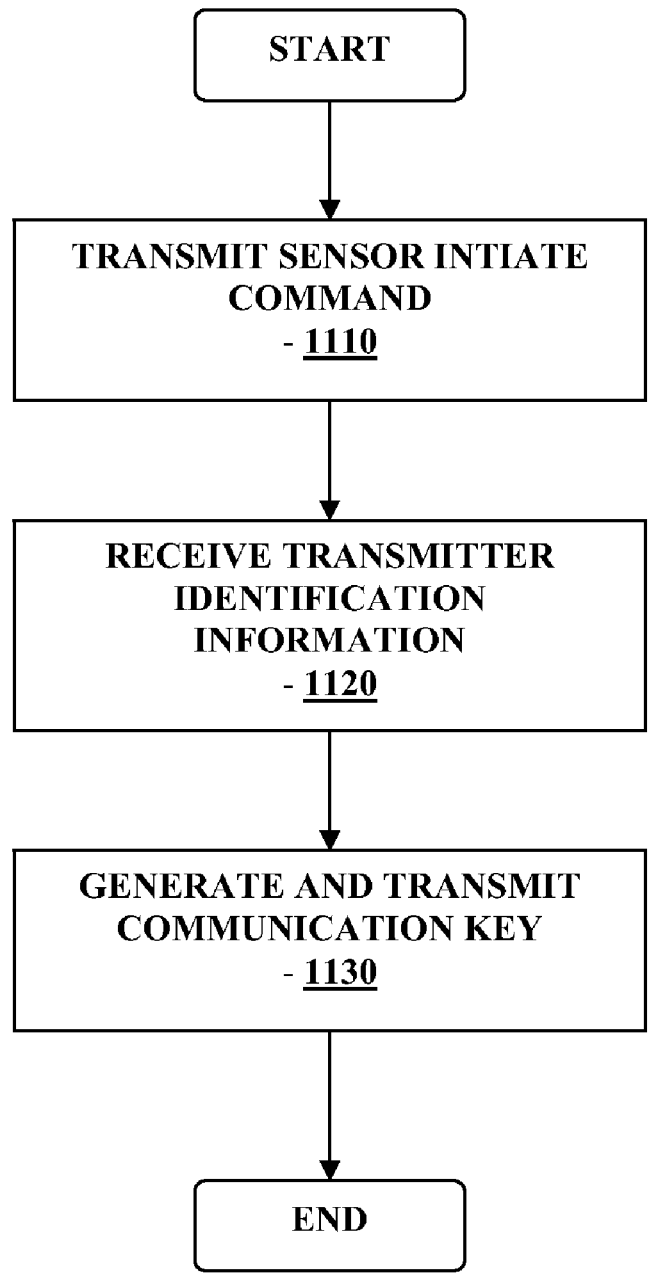
FIG. 11 is a flowchart illustrating the pairing or synchronization routine in the data monitoring and management system of FIG. 1 in accordance with another embodiment of the present invention.

Referring now to FIG. 11, a flowchart illustrating the pairing or synchronization routine in the data monitoring and management system of FIG. 1 in accordance with another embodiment of the present invention is shown. That is, in one aspect, FIG. 11 illustrates the pairing or synchronization routine from the receiver unit 104. Referring back to FIG. 11, the sensor initiate command is transmitted to the transmitter unit 102 (1110) when the receiver unit 104 is positioned within a close transmission range. Thereafter, in one aspect, the transmitter identification information is received (1120) for example, from the transmitter unit that received the sensor initiate command. Thereafter, a communication key (optionally encrypted) may be generated and transmitted (1130) to the transmitter unit.

In the manner described above, in one embodiment, a simplified pairing or synchronization between the transmitter unit 102 and the receiver unit 104 may be established using, for example, close proximity commands between the devices. As described above, in one aspect, upon pairing or synchronization, the transmitter unit 102 may be configured to periodically transmit analyte level information to the receiver unit for further processing.

Figure 12:
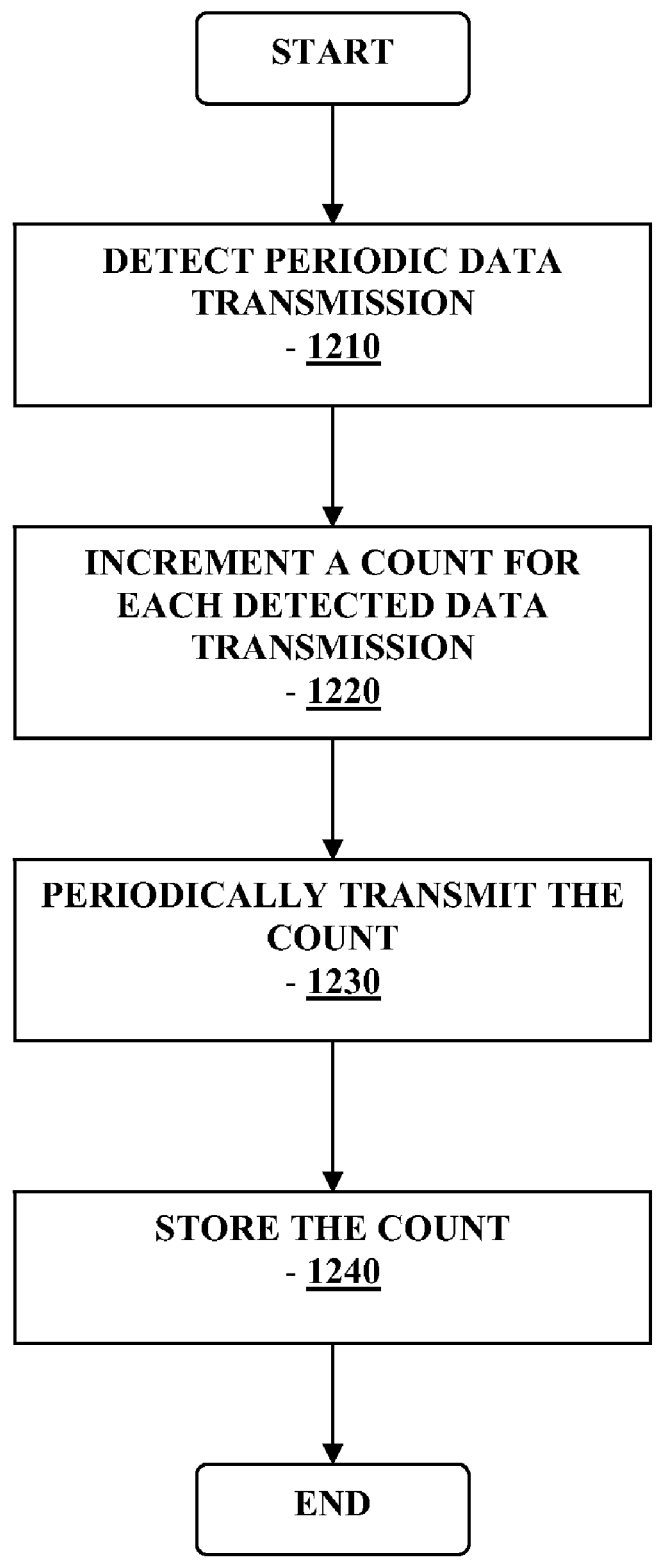
FIG. 12 is a flowchart illustrating the power supply determination in the data monitoring and management system of FIG. 1 in accordance with one embodiment of the present invention.

FIG. 12 is a flowchart illustrating the power supply determination in the data monitoring and management system of FIG. 1 in accordance with one embodiment of the present invention. That is, in one embodiment, using a counter, the receiver unit 104 may be configured to determine the power supply level of the transmitter unit 102 battery so as to determine a suitable time for replacement of the power supply or the transmitter unit 102 itself. Referring to FIG. 12, periodic data transmission is detected (1210), and a corresponding count in the counter is incremented for example, by one with each detected data transmission (1220). In particular, a Hobbs counter may be used in the rolling data configuration described above to provide a count that is associated with the transmitter unit data transmission occurrence.

Referring to FIG. 12, the updated or incremented count stored in the Hobbs counter is periodically transmitted in the data packet from the transmitter unit 102 to the receiver unit 104. Moreover, the incremented or updated count may be stored (1240) in a persistent nonvolatile memory unit of the transmitter unit 102. Accordingly, based on the number of data transmission occurrences, the battery power supply level may be estimated, and in turn, which may provide an indication as to when the battery (and thus the transmitter unit in the embodiment where the power supply is manufactured to be embedded within the transmitter unit housing) needs to be replaced.

Moreover, in one aspect, the incremented count in the Hobbs counter is stored in a persistent nonvolatile memory such that, the counter is not reset or otherwise restarted with each sensor unit replacement.

Figure 13:
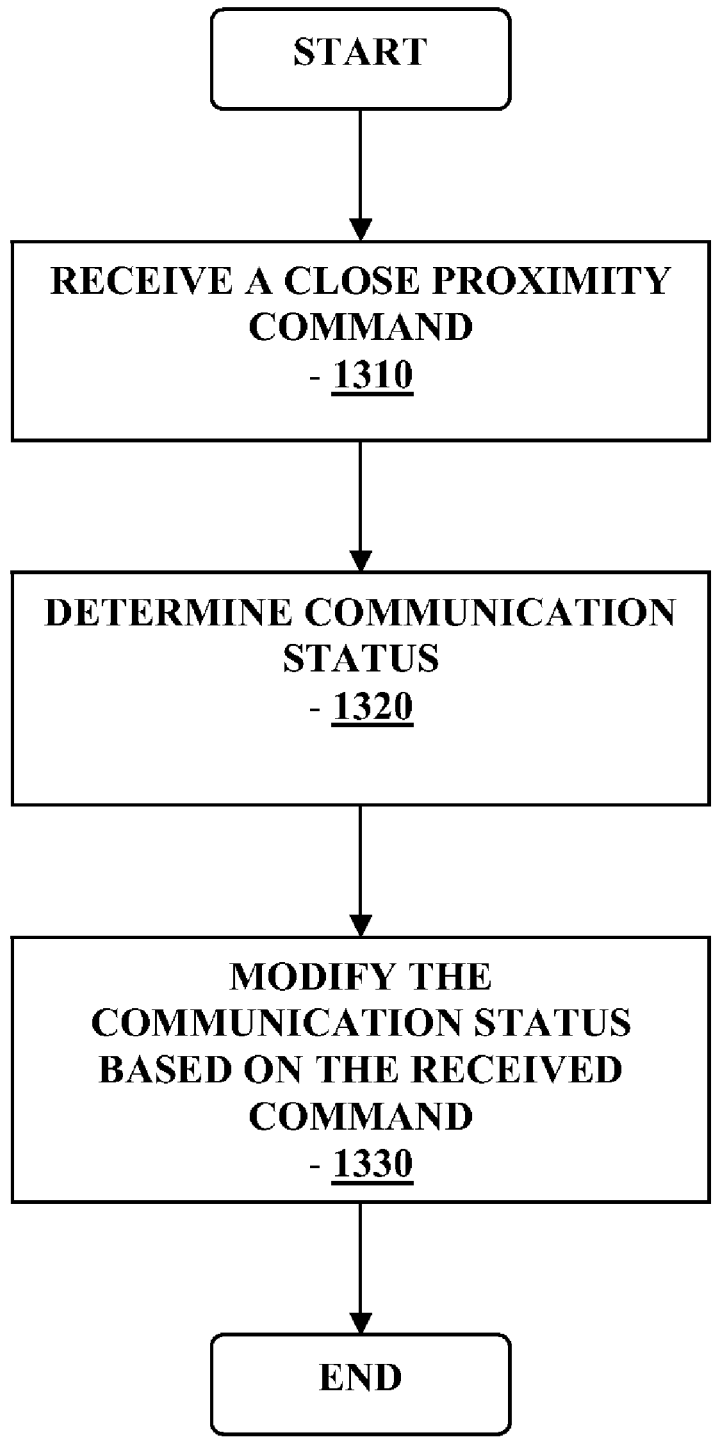
FIG. 13 is a flowchart illustrating close proximity command for RF communication control in the data monitoring and management system of FIG. 1 in accordance with one embodiment of the present invention.

FIG. 13 is a flowchart illustrating close proximity command for RF communication control in the data monitoring and management system of FIG. 1 in accordance with one embodiment of the present invention. Referring to FIG. 13, a close proximity command associated with communication status, for example is received (1310). In one aspect, the command associated with the communication status may include, for example, a communication module turn on or turn off command for, for example, turning on or turning off the associated RF communication device of the transmitter unit 102. Referring to FIG. 13, the communication status is determined (1320), and thereafter, modified based on the received command (1330).

That is, in one aspect, using one or more close proximity commands, the receiver unit 104 may be configured to control the RF communication of the transmitter unit 102 to, for example, disable or turn off the RF communication functionality for a predetermined time period. This may be particularly useful when used in air travel or other locations such as hospital settings, where RF communication devices need to be disabled. In one aspect, the close proximity command may be used to either turn on or turn off the RF communication module of the transmitter unit 102, such that, when the receiver unit 104 is positioned in close proximity to the transmitter unit 102, and the RF command is transmitted, the transmitter unit 102 is configured, in one embodiment, to either turn off or turn on the RF communication capability of the transmitter unit 102.

Figure 14:
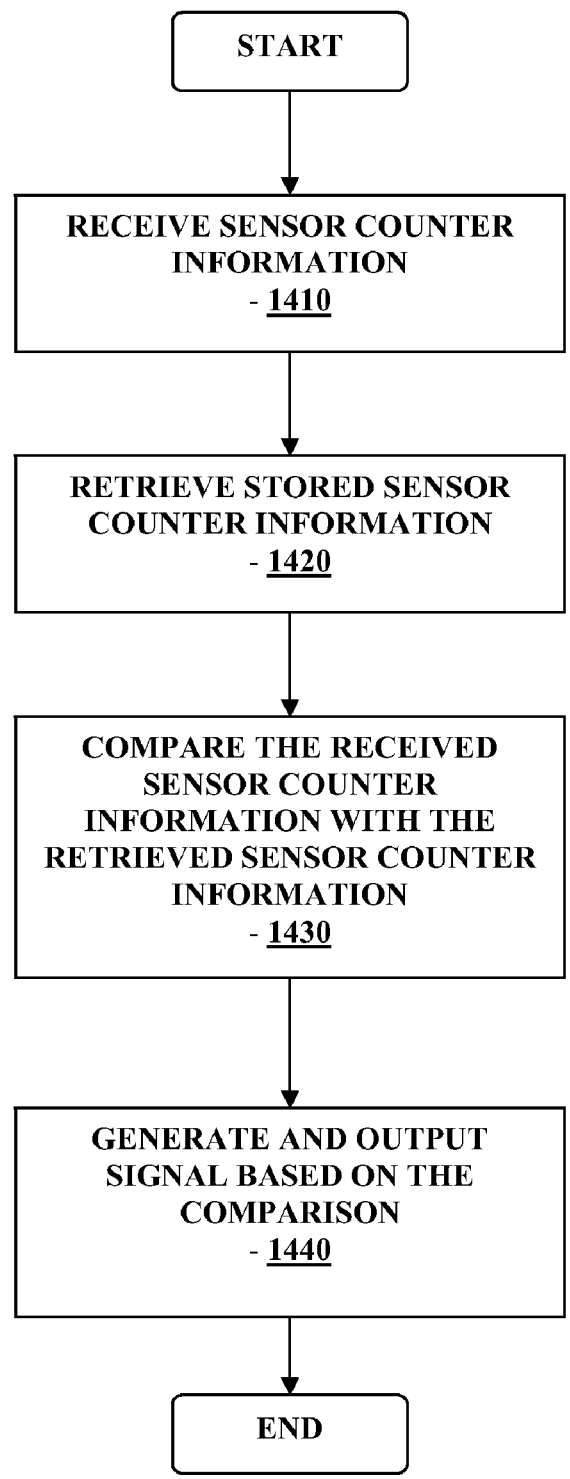
FIG. 14 is a flowchart illustrating analyte sensor identification routine in accordance with one embodiment of the present invention.

FIG. 14 is a flowchart illustrating analyte sensor identification routine in accordance with one embodiment of the present invention. Referring to FIG. 14, periodically, sensor counter information is received (1410), for example included as rolling data discussed above. The received sensor counter information may be stored in one or more storage units such as a memory unit. When the sensor counter information is received, a stored sensor counter information is retrieved (1420), and the retrieved sensor counter information is compared with the received sensor counter information (1430). Based on the comparison between the retrieved sensor counter information and the received sensor counter information, one or more signal is generated and output (1440).

That is, in one aspect, the sensor counter in the transmitter unit 102 may be configured to increment by one with each new sensor replacement. Thus, in one aspect, the sensor counter information may be associated with a particular sensor from which monitored analyte level information is generated and transmitted to the receiver unit 104. Accordingly, in one embodiment, based on the sensor counter information, the receiver unit 104 may be configured to ensure that the analyte related data is generated and received from the correct analyte sensor transmitted from the transmitter unit 102.

An analyte monitoring device in one embodiment includes a counter, and a data processing section coupled to the counter, the data processing section configured to increment a count stored in the counter based on a detection of an analyte sensor.

The counter may include a nonvolatile memory unit.

The data processing section may include a communication module to transmit data related to the count.

A control device for communicating with an analyte monitoring unit in one embodiment includes a data communication section configured to periodically receive data including a count information related to an analyte sensor associated with the received data, and a processing unit coupled to the data communication section to process the received data, the processing unit further configured to compare the count information in each data periodically received, and when it is determined that the count information of the periodically received data is different, the processing unit is configured to generate one or more signals related to the status of the analyte sensor.

In one aspect, the one or more signals generated may include a command to disable the data communication section.

The one or more signals generated may be provided to a user.

The device in a further aspect may include a display unit and where the one or more signals generated is displayed on the display unit.

In yet another aspect, the one or more signals output may include one or more of a visual indicator, an audible indicator or a vibratory indicator.

A method in accordance with yet another embodiment includes detecting an analyte sensor, updating a count associated with the detected analyte sensor, and transmitting the updated count.

The method may include storing the updated count.

Additionally, the method may include detecting a further analyte sensor, further updating the count associated with the detected further analyte sensor, and transmitting the further updated count.

A method in accordance with still another embodiment includes periodically receiving data including a count information related to an analyte sensor associated with the received data, and comparing the count information in each data periodically received, and when it is determined that the count information of the periodically received data is different, generating one or more signals related to the status of the analyte sensor.

The one or more signals generated may include a command to disable data communication.

The method may also include providing the one or more signals generated to a user, and also, include outputting the one or more signals generated.

In still a further aspect, the method may include storing the count information.

The status of the analyte sensor may include a new analyte sensor detection.

Additionally, the method may include prompting a user to replace the analyte sensor.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An analyte monitoring device, comprising:
a data storage unit; and
one or more processors operatively coupled to the data storage unit and configured to retrieve instructions stored in the data storage unit to establish a communication path with a remote device when the remote device is placed within a predetermined distance from the analyte monitoring device, to determine when a transcutaneously positioned analyte sensor is initialized, to increment a count based on the determination, and to associate the incremented count with the transcutaneously positioned analyte sensor; and
a communication module operatively coupled to the one or more processors and configured to transmit the incremented count to the remote device when the remote device is placed within the predetermined distance, wherein the identity of a new transcutaneously positioned analyte sensor is based on the incremented count.

2. The device of claim 1 wherein the data storage unit includes a nonvolatile memory unit.

3. The device of claim 1 wherein the predetermined distance is approximately one foot or less.

4. A control device for communicating with an analyte monitoring unit, comprising:
a data communication section configured to establish a communication range with the analyte monitoring unit when the control device is placed within a predetermined distance from the analyte monitoring unit, the data communication section further configured to receive data, including a sensor information associated with a transcutaneously positioned analyte sensor, when the control device is placed within the established communication range; and
a processing unit coupled to the data communication section to process the received data, the processing unit further configured to compare the sensor information in the received data with a stored sensor information to verify the identity of the transcutaneously positioned analyte sensor, and when it is determined that the received sensor information is different than the stored sensor information, the processing unit is configured to determine the identity of the transcutaneously positioned analyte sensor, and to generate one or more signals based at least in part on processing the received data.

5. The device of claim 4 wherein the generated one or more signals include a command to disable the data communication section.

6. The device of claim 4 wherein the generated one or more signals is output to a user.

7. The device of claim 6 including a display unit to display the generated one or more signals.

8. The device of claim 6 wherein the one or more signals output includes one or more of a visual indicator, an audible indicator or a vibratory indicator.

9. The device of claim 6 wherein the one or more signals output includes a directional arrow indicator.

10. The device of claim 6 wherein the one or more signals output includes monitored analyte level information and a monitored analyte level trend indicator.

11. A method, comprising:
establishing data communication between an analyte monitoring device and a remote device when the remote device is positioned within a predetermined distance from the analyte monitoring device;
communicating a count associated with a transcutaneously positioned analyte sensor to the remote device, wherein the identity of the transcutaneously positioned analyte sensor is verified based at least in part on the count;
detecting replacement of the transcutaneously positioned analyte sensor;
updating the count based on the detected replacement and communicating data from the analyte sensor to the remote device; and
generating one or more signals based on the data from the analyte sensor.

12. The method of claim 11 including:
detecting a further replacement of the transcutaneously positioned analyte sensor; and
further updating the count associated with the detected further replacement of the transcutaneously positioned analyte sensor.

13. The method of claim 11 wherein the generated one or more signals includes a command to disable data communication.

14. The method of claim 11 including providing the generated one or more signals to a user.

15. The method of claim 14 including outputting the generated one or more signals.

16. The method of claim 11 including storing the received count information when it is determined that the received count information is different than the stored count information.

17. The method of claim 11 wherein detecting replacement of the transcutaneously positioned analyte sensor includes a new transcutaneously positioned analyte sensor detection.

18. The method of claim 11 wherein the generated one or more signals includes prompting a user to replace the transcutaneously positioned analyte sensor.

* * * * *